US011746153B2

(12) United States Patent
Vousden et al.

(10) Patent No.: US 11,746,153 B2
(45) Date of Patent: Sep. 5, 2023

(54) BINDING MOLECULES SPECIFIC FOR FCγRIIA AND USES THEREOF

(71) Applicant: VIELA BIO, INC., Deerfield, IL (US)

(72) Inventors: Katherine Ann Vousden, Cambridgeshire (GB); Bo Chen, Frederick, MD (US); Gary Patrick Sims, Potomac, MD (US)

(73) Assignee: Viela Bio, Inc., Deerfield, IL (US)

( * ) Notice: Subject to any disclaimer, the term of this patent is extended or adjusted under 35 U.S.C. 154(b) by 0 days.

(21) Appl. No.: 17/684,018

(22) Filed: Mar. 1, 2022

(65) Prior Publication Data

US 2022/0380458 A1 Dec. 1, 2022

Related U.S. Application Data

(63) Continuation of application No. 16/097,573, filed as application No. PCT/EP2017/060188 on Apr. 28, 2017, now Pat. No. 11,306,145.

(60) Provisional application No. 62/329,627, filed on Apr. 29, 2016, provisional application No. 62/349,804, filed on Jun. 14, 2016.

(51) Int. Cl.

| | |
|---|---|
| ***C12Q 1/68*** | (2018.01) |
| ***C07K 16/28*** | (2006.01) |
| ***A61P 7/00*** | (2006.01) |

(52) U.S. Cl.

CPC .............. *C07K 16/283* (2013.01); *A61P 7/00* (2018.01); *C07K 2317/24* (2013.01); *C07K 2317/33* (2013.01); *C07K 2317/565* (2013.01); *C07K 2317/76* (2013.01); *C07K 2317/77* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 11,306,145 | B2 | 4/2022 | Vousden et al. |
| 2015/0322152 | A1 | 11/2015 | Bruhns et al. |
| 2016/0347838 | A1 | 12/2016 | Francis et al. |
| 2020/0002415 | A1 | 1/2020 | Vousden et al. |

FOREIGN PATENT DOCUMENTS

| | | | |
|---|---|---|---|
| CN | 103492565 | A | 1/2014 |
| WO | WO2014/083379 | A1 | 6/2014 |
| WO | WO2016/086175 | A1 | 6/2016 |

OTHER PUBLICATIONS

Decision to Grant for Japanese Application No. 2018-556351, dated Jan. 4, 2022, 5 pages.

European Search Report for Application No. 17722712.1, dated Mar. 30, 2022, 9 pages.

Office Action for Application No. U.S. Appl. No. 16/097,573, dated Oct. 8, 2020, 9 pages.

Final Office Action for Application No. U.S. Appl. No. 16/097,573 dated May 24, 2021, 5 pages.

International Search Report and Written Opinion issued in International Application No. PCT/EP2017/060188 dated Nov. 2, 2017, 16 pages.

Casset et al., "A peptide mimetic of an anti-CD4 monoclonal antibody by rational design," (2003) BBRC 307, 198-205.

Chen et al., "Selection and Analysis of an Optimized Anti-VEGF Antibody: Crystal Structure of an Affinity-matured Fab in complex with Antigen," J. Mol. Bio. (1999) 293, 865-881.

Dall'Acqua et al., "Properties of Human IgG1s Engineered for Enhanced Binding to the Neonatal Fc Receptor (FcRn)," J. Biol. Chem., Aug. 2006, 281(33): 23514-23524.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology (2002) 169, 3076-3084.

Holm et al., "Functional mapping and single chain construction of the anti-cytokeratin 8 monoclonal antibody TS1," (2007) 44, 1075-1084.

Looney et al., "Human monocytes and U937 cells bear two distinct Fe receptors for IgG," The Journal of Immunologv, 1986, vol. 136, pp. 1641-1647.

MacCallum et al. "Antibody-antigen Interactions: Contact Analysis and Binding Site Topography," J. Mol. Biol. (1996) 262,732-745.

Meyer, T. et al., "CD32a antibodies induce thrombocytopenia and type II hypersensitivity reactions in FCGR2A mice", Blood, vol. 126, No. 19, Nov. 5, 2015, pp. 2230-2238.

New Jaa Yien et al., "Heparin-Induced Thrombocytopenia and Thrombosis: Therapeutic Strategy Using a Single-Chain Variable Fragment (scFv) Antibody", Blood, vol. 120, No. 21, Nov. 30, 2012, p. 3346.

Oganesyan et al., "Structural characterization of a human Fe fragment engineered for lack of effector functions," Acta Crystallographica Section D Biological Crystallography, 2008, D64, 700-704.

Rudikoff et al., "Single amino acid substitution altering antigen-binding specificity", Proc. Natl. Acad. Sci. USA, Mar. 1982, vol. 79, pp. 1979-1983.

Vajdos et al., "Comprehensive Functional Maps of the Antigen-binding Site of an Anti-ErbB2 Antibody Obtained with Shotgun Scanning Mutagenesis," J. Mo. Biol., (2002) 320, 415-428.

Wei et al., "Significance of FcyRIIa and related inflammatory molecules in ANCA associated vasculitis," Modern Preventive Medicine, Nov. 25, 2014, vol. 41, Issue 22, pp. 4184-4185 (English translation of Abstract provided).

Wu et al., "Humanization of a Murine Monoclonal Antibody by Simultaneous Optimization of Framework and CDR Residues," J. Mol. Biol. (1999) 294, 151-162.

*Primary Examiner* — Jennifer E Graser

(74) *Attorney, Agent, or Firm* — COOLEY LLP

(57) ABSTRACT

The disclosure provides FcγRIIA-binding molecules, for example, humanized monoclonal antibodies capable of inhibiting FcγRIIA activity, and methods of using the FcγRIIA binding molecules, for example, in treating or preventing inflammatory, immune-mediated, or autoimmune diseases or disorders.

9 Claims, 17 Drawing Sheets

Specification includes a Sequence Listing.

FIG. 1A

MTMETQMSQNVCPGNLWLLQPLTVLLLLASADSQTAAPPKAVLKLEPPWINVLREDSVTL
TCGGAHSPDSDSTQWFHNGNLIPTHTQPSYRFKANNNDSGEYRCQTGRTSLSDPVHLTVL
SEWLALQTTHLEFREGETIMLRCHSWKDKPLIKVAFFQNGISKKFSHMNPNFSIPQANHS
HSGDYHCTGNIGYTPYSSKPVTITVQVPSVGSSSPMGIIVAVVTGIAVAAVVAAVVALIY
CRKKRISANSTDPVKAARNEPLGRQTIALRKRQLEETNNDYETADGGYMTLNPRAPTDDD
RNIYMTLSPNDYDNSNN (SEQ ID NO: 1)

FIG. 1B

Sequences: 2. Scoring matrix: BLOSUM 62

Sequence View: Similarity Format, Color behind non-matches

```
hFCGR2a      1 mtmetqmsqnvcprnlwllqpltvllllasadsqaaappkavlkleppwinvlqedsvtl
cyFCGR2a     1 mtmetqmsqnvcpgnlwllqpltvllllasadsqtaappkavlkleppwinvlredsvtl

hFCGR2a     61 tcqgarspesdsiqwfhngnlipthtqpsyrfkannndsgeytcqtgqtslsdpvhltvl
cyFCGR2a    61 tcggahspdsdstqwfhngnlipthtqpsyrfkannndsgeyrcqtgrtslsdpvhltvl

hFCGR2a    121 sewlvlqtphlefqegetimlrchswkdkplvkvtffqngksqkfshldptfsipqanhs
cyFCGR2a   121 sewlalqtthlefregetimlrchswkdkplikvaffqngiskkfshmnpnfsipqanhs

hFCGR2a    181 hsgdyhctgnigytlfsskpvtitvqvpsmgssspmgiivavviatavaaivaavvaliy
cyFCGR2a   181 hsgdyhctgnigytpyssk pvtitvqvpsvgssspmgiivavvtgiavaavvaavvaliy

hFCGR2a    241 crkkrisanstdpvkaaqfeppgrqmiairkrqleetnndyetadggymtlnpraptddd
cyFCGR2a   241 crkkrisanstdpvkaarneplgrqtialrkrqleetnndyetadggymtlnpraptddd

hFCGR2a    301 kniyltlppndhvnsnn (SEQ ID NO: 2)
cyFCGR2a   301 rniymtlspndydnsnn (SEQ ID NO: 3)
```

FIG. 1C

ATGACTATGGAGACCCAAATGTCTCAGAATGTATGTCCCGGCAACCTGTGGCTGCTTCAA
CCATTGACAGTTTTGCTGCTGCTGGCTTCTGCAGACAGTCAAACTGCAGCTCCCCCAAAG
GCTGTGCTGAAACTCGAGCCCCCGTGGATCAACGTGCTCCGGGAGGACTCTGTGACTCTG
ACGTGCGGGGGCGCTCACAGCCCTGACAGCGACTCCACTCAGTGGTTCCACAATGGGAAT
CTCATCCCCACCCACACGCAGCCCAGCTACAGGTTCAAGGCCAACAACAATGATAGCGGG
GAGTACAGGTGCCAGACTGGCCGGACCAGCCTCAGCGACCCTGTTCATCTGACTGTGCTT
TCTGAGTGGCTGGCGCTTCAGACCACTCACCTGGAGTTCCGGGAGGGAGAAACCATCATG
CTGAGGTGCCACAGCTGGAAGGACAAGCCTCTGATCAAGGTCGCATTCTTCCAGAATGGA
ATATCCAAGAAATTTTCCCATATGAATCCCAACTTCTCCATCCCACAAGCAAACCACAGT
CACAGTGGTGATTACCACTGCACAGGAAACATAGGCTACACGCCATACTCATCCAAACCT
GTGACCATCACTGTCCAAGTGCCCAGCGTGGGCAGCTCTTCACCGATGGGGATCATTGTG
GCTGTGGTCACTGGGATTGCTGTAGCGGCCGTTGTTGCTGCTGTAGTGGCCTTGATCTAC
TGCAGGAAAAAGCGGATTTCAGCCAATTCCACTGATCCTGTGAAGGCTGCCCGAAATGAG
CCACTTGGACGTCAAACGATTGCCCTCAGAAAGAGACAACTTGAAGAAACCAACAATGAC
TATGAAACAGCCGACGGCGGCTACATGACTCTGAACCCCAGGGCACCTACTGATGATGAT
AGAAACATCTACATGACTCTTTCTCCCAACGACTATGACAACAGTAATAACTAA
(SEQ ID NO: 4)

FIG. 4A Epitope Competiton - HuCD32a 131H
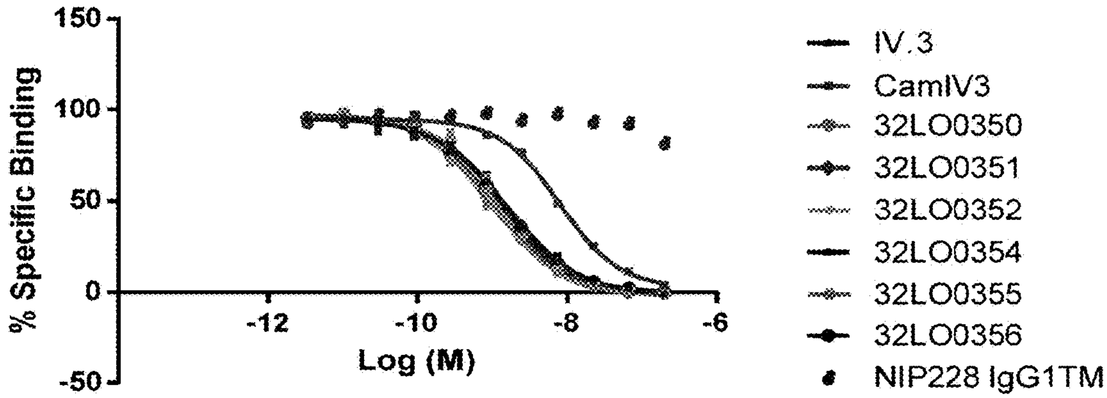
FIG. 4B Epitope Competiton - HuCD32a 131R
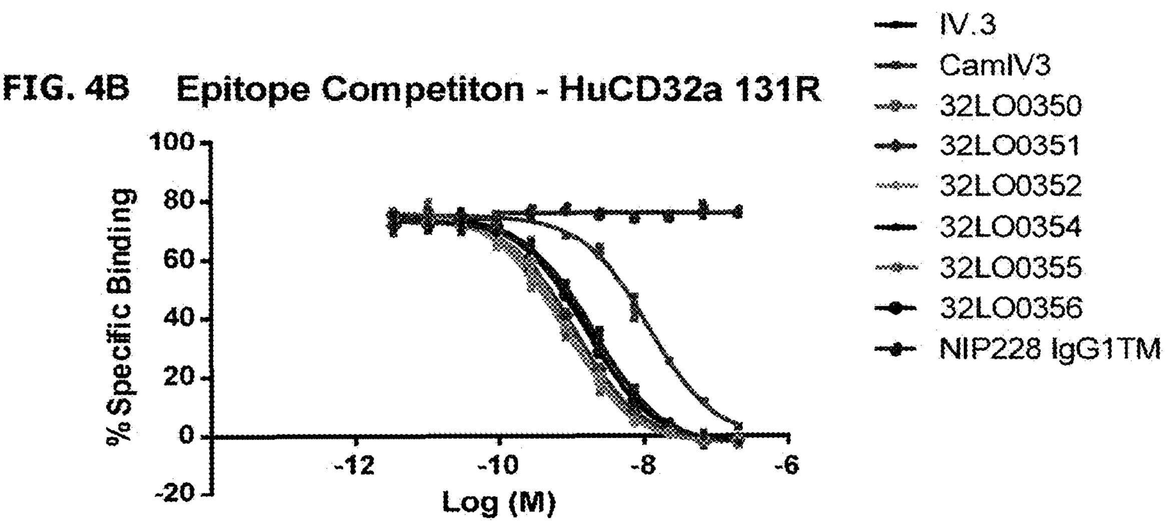

| | MEDI9600 | MEDI9600 +IVIG |
|---|---|---|
| EC50 | 0.02927 | 3.347 |

| | IV.3 chimeric | Cam IV.3 | 32LO0350 | 32LO0351 | 32LO0352 | 32LO0354 | 32LO0355 | 32LO0356 |
|---|---|---|---|---|---|---|---|---|
| IC50 | 0.1907 | 0.2408 | 0.06918 | 0.05237 | 0.08086 | 0.04171 | 0.09145 | 0.04396 |

| | IV.3 chimeric | Cam IV.3 | 32LO0350 | 32LO0351 | 32LO0352 | 32LO0354 | 32LO0355 | 32LO0356 |
|---|---|---|---|---|---|---|---|---|
| IC50 | 0.1975 | 0.3070 | 0.05365 | 0.05594 | 0.05931 | 0.03904 | 0.06441 | 0.04306 |

| | IV.3 chimeric | Cam IV.3 | 32LO0350 | 32LO0351 | 32LO0352 | 32LO0354 | 32LO0355 | 32LO0356 |
|---|---|---|---|---|---|---|---|---|
| IC50 | 7.824 | 10.49 | 1.198 | 16.39 | 1.088 | 5.141 | 1.015 | 3.778 |

| | IV.3 | Cam IV.3 | 32LO0350 | 32LO0351 | 32LO 0352 | 32IO0355 |
|---|---|---|---|---|---|---|
| IC50 | 0.5194 | 2.047 | 0.3165 | 0.2567 | 0.4811 | 0.7076 |

| | IV.3 | Cam IV.3 | 32LO0350 | 32LO0351 | 32LO 0352 | 32IO0355 |
|---|---|---|---|---|---|---|
| IC50 | 0.7911 | 3.880 | 0.7134 | 0.3094 | 0.3467 | 0.5615 |

| | IV.3 | Cam IV.3 | 32LO0350 | 32LO0351 | 32LO 0352 | 32IO0355 |
|---|---|---|---|---|---|---|
| IC50 | 13.16 | 38.15 | 6.108 | 19.87 | 4.478 | 8.042 |

SEQUENCE LISTING

```
<160> NUMBER OF SEQ ID NOS: 45

<210> SEQ ID NO 1
<211> LENGTH: 317
<212> TYPE: PRT
<213> ORGANISM: Macaca fascicularis

<400> SEQUENCE: 1

Met Thr Met Glu Thr Gln Met Ser Gln Asn Val Cys Pro Gly Asn Leu
1               5                   10                  15

Trp Leu Leu Gln Pro Leu Thr Val Leu Leu Leu Leu Ala Ser Ala Asp
            20                  25                  30

Ser Gln Thr Ala Ala Pro Pro Lys Ala Val Leu Lys Leu Glu Pro Pro
        35                  40                  45

Trp Ile Asn Val Leu Arg Glu Asp Ser Val Thr Leu Thr Cys Gly Gly
    50                  55                  60
```

Ala His Ser Pro Asp Ser Asp Ser Thr Gln Trp Phe His Asn Gly Asn
65 70 75 80

Leu Ile Pro Thr His Thr Gln Pro Ser Tyr Arg Phe Lys Ala Asn Asn
85 90 95

Asn Asp Ser Gly Glu Tyr Arg Cys Gln Thr Gly Arg Thr Ser Leu Ser
100 105 110

Asp Pro Val His Leu Thr Val Leu Ser Glu Trp Leu Ala Leu Gln Thr
115 120 125

Thr His Leu Glu Phe Arg Glu Gly Glu Thr Ile Met Leu Arg Cys His
130 135 140

Ser Trp Lys Asp Lys Pro Leu Ile Lys Val Ala Phe Phe Gln Asn Gly
145 150 155 160

Ile Ser Lys Lys Phe Ser His Met Asn Pro Asn Phe Ser Ile Pro Gln
165 170 175

Ala Asn His Ser His Ser Gly Asp Tyr His Cys Thr Gly Asn Ile Gly
180 185 190

Tyr Thr Pro Tyr Ser Ser Lys Pro Val Thr Ile Thr Val Gln Val Pro
195 200 205

Ser Val Gly Ser Ser Ser Pro Met Gly Ile Ile Val Ala Val Val Thr
210 215 220

Gly Ile Ala Val Ala Ala Val Val Ala Ala Val Val Ala Leu Ile Tyr
225 230 235 240

Cys Arg Lys Lys Arg Ile Ser Ala Asn Ser Thr Asp Pro Val Lys Ala
245 250 255

Ala Arg Asn Glu Pro Leu Gly Arg Gln Thr Ile Ala Leu Arg Lys Arg
260 265 270

Gln Leu Glu Glu Thr Asn Asn Asp Tyr Glu Thr Ala Asp Gly Gly Tyr
275 280 285

Met Thr Leu Asn Pro Arg Ala Pro Thr Asp Asp Asp Arg Asn Ile Tyr
290 295 300

Met Thr Leu Ser Pro Asn Asp Tyr Asp Asn Ser Asn Asn
305 310 315

<210> SEQ ID NO 2
<211> LENGTH: 317
<212> TYPE: PRT
<213> ORGANISM: Homo sapiens

<400> SEQUENCE: 2

Met Thr Met Glu Thr Gln Met Ser Gln Asn Val Cys Pro Arg Asn Leu
1 5 10 15

Trp Leu Leu Gln Pro Leu Thr Val Leu Leu Leu Leu Ala Ser Ala Asp
20 25 30

Ser Gln Ala Ala Ala Pro Pro Lys Ala Val Leu Lys Leu Glu Pro Pro
35 40 45

Trp Ile Asn Val Leu Gln Glu Asp Ser Val Thr Leu Thr Cys Gln Gly
50 55 60

Ala Arg Ser Pro Glu Ser Asp Ser Ile Gln Trp Phe His Asn Gly Asn
65 70 75 80

Leu Ile Pro Thr His Thr Gln Pro Ser Tyr Arg Phe Lys Ala Asn Asn
85 90 95

Asn Asp Ser Gly Glu Tyr Thr Cys Gln Thr Gly Gln Thr Ser Leu Ser
100 105 110

Asp Pro Val His Leu Thr Val Leu Ser Glu Trp Leu Val Leu Gln Thr

```
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Asp Lys Asn Ile Tyr
    290                 295                 300

Leu Thr Leu Pro Pro Asn Asp His Val Asn Ser Asn Asn
305                 310                 315


<210> SEQ ID NO 3
<211> LENGTH: 317
<212> TYPE: PRT
<213> ORGANISM: Macaca fascicularis

<400> SEQUENCE: 3

Met Thr Met Glu Thr Gln Met Ser Gln Asn Val Cys Pro Gly Asn Leu
1               5                   10                  15

Trp Leu Leu Gln Pro Leu Thr Val Leu Leu Leu Leu Ala Ser Ala Asp
            20                  25                  30

Ser Gln Thr Ala Ala Pro Pro Lys Ala Val Leu Lys Leu Glu Pro Pro
        35                  40                  45

Trp Ile Asn Val Leu Arg Glu Asp Ser Val Thr Leu Thr Cys Gly Gly
    50                  55                  60

Ala His Ser Pro Asp Ser Asp Ser Thr Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Arg Cys Gln Thr Gly Arg Thr Ser Leu Ser
            100                 105                 110

Asp Pro Val His Leu Thr Val Leu Ser Glu Trp Leu Ala Leu Gln Thr
        115                 120                 125

Thr His Leu Glu Phe Arg Glu Gly Glu Thr Ile Met Leu Arg Cys His
    130                 135                 140

Ser Trp Lys Asp Lys Pro Leu Ile Lys Val Ala Phe Phe Gln Asn Gly
145                 150                 155                 160

Ile Ser Lys Lys Phe Ser His Met Asn Pro Asn Phe Ser Ile Pro Gln
                165                 170                 175
```

```
Ala Asn His Ser His Ser Gly Asp Tyr His Cys Thr Gly Asn Ile Gly
            180                 185                 190

Tyr Thr Pro Tyr Ser Ser Lys Pro Val Thr Ile Thr Val Gln Val Pro
        195                 200                 205

Ser Val Gly Ser Ser Ser Pro Met Gly Ile Ile Val Ala Val Val Thr
    210                 215                 220

Gly Ile Ala Val Ala Ala Val Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Arg Asn Glu Pro Leu Gly Arg Gln Thr Ile Ala Leu Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Asp Arg Asn Ile Tyr
    290                 295                 300

Met Thr Leu Ser Pro Asn Asp Tyr Asp Asn Ser Asn Asn
305                 310                 315


<210> SEQ ID NO 4
<211> LENGTH: 954
<212> TYPE: DNA
<213> ORGANISM: Macaca fascicularis

<400> SEQUENCE: 4

atgactatgg agacccaaat gtctcagaat gtatgtcccg gcaacctgtg gctgcttcaa     60

ccattgacag ttttgctgct gctggcttct gcagacagtc aaactgcagc tcccccaaag    120

gctgtgctga aactcgagcc cccgtggatc aacgtgctcc gggaggactc tgtgactctg    180

acgtgcgggg gcgctcacag ccctgacagc gactccactc agtggttcca caatgggaat    240

ctcatcccca cccacacgca gcccagctac aggttcaagg ccaacaacaa tgatagcggg    300

gagtacaggt gccagactgg ccggaccagc ctcagcgacc ctgttcatct gactgtgctt    360

tctgagtggc tggcgcttca gaccactcac ctggagttcc gggagggaga aaccatcatg    420

ctgaggtgcc acagctggaa ggacaagcct ctgatcaagg tcgcattctt ccagaatgga    480

atatccaaga aattttccca tatgaatccc aacttctcca tcccacaagc aaaccacagt    540

cacagtggtg attaccactg cacaggaaac ataggctaca cgccatactc atccaaacct    600

gtgaccatca ctgtccaagt gcccagcgtg ggcagctctt caccgatggg gatcattgtg    660

gctgtggtca ctgggattgc tgtagcggcc gttgttgctg ctgtagtggc cttgatctac    720

tgcaggaaaa agcggatttc agccaattcc actgatcctg tgaaggctgc ccgaaatgag    780

ccacttggac gtcaaacgat tgccctcaga aagagacaac ttgaagaaac caacaatgac    840

tatgaaacag ccgacggcgg ctacatgact ctgaacccca gggcacctac tgatgatgat    900

agaaacatct acatgactct ttctcccaac gactatgaca acagtaataa ctaa          954


<210> SEQ ID NO 5
<211> LENGTH: 120
<212> TYPE: PRT
<213> ORGANISM: Artificial sequence
<220> FEATURE:
<223> OTHER INFORMATION: Mouse IV.3 VH domain

<400> SEQUENCE: 5

Gln Ile Gln Leu Val Gln Ser Gly Pro Glu Leu Lys Lys Pro Gly Glu
1               5                   10                  15
```

```
Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser
        115                 120


<210> SEQ ID NO 6
<211> LENGTH: 120
<212> TYPE: PRT
<213> ORGANISM: Artificial Sequence
<220> FEATURE:
<223> OTHER INFORMATION: Cam IV.3 VH domain

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Arg Leu Glu Trp Met
        35                  40                  45

Gly Trp Leu Asn Thr Tyr Thr Gly Glu Ser Ile Tyr Pro Asp Asp Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Gly Tyr Asp Asp Pro Leu Asp Tyr Trp Gly Gln
            100                 105                 110

Gly Thr Leu Val Thr Val Ser Ser
        115                 120


<210> SEQ ID NO 7
<211> LENGTH: 109
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Trp Gly Gln Gly Thr Leu Val Thr Val Ser Ser
            100                 105


<210> SEQ ID NO 8
<211> LENGTH: 112
<212> TYPE: PRT
<213> ORGANISM: Artificial Sequence
<220> FEATURE:
<223> OTHER INFORMATION: Mouse IV.3 VL domain

<400> SEQUENCE: 8

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Thr
            20                  25                  30

Asn Gly Asn Thr Tyr Leu His Trp Phe Leu Gln Arg Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Ala Phe Thr Leu Ser Ile
65                  70                  75                  80

Ser Arg Val Glu Ala Glu Asp Val Gly Val Phe Tyr Cys Met Gln His
                85                  90                  95

Leu Glu Tyr Pro Leu Thr Phe Gly Ala Gly Thr Lys Leu Glu Leu Lys
            100                 105                 110


<210> SEQ ID NO 9
<211> LENGTH: 112
<212> TYPE: PRT
<213> ORGANISM: Artificial Sequence
<220> FEATURE:
<223> OTHER INFORMATION: Cam IV.3 VL domain

<400> SEQUENCE: 9

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Leu Gly Asn Thr Tyr Leu His Trp Phe Leu Gln Lys Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110


<210> SEQ ID NO 10
<211> LENGTH: 110
<212> TYPE: PRT
<213> ORGANISM: Homo sapiens

<400> SEQUENCE: 10

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Gly Gln Gly Thr Lys Leu Glu Ile Lys
            100                 105                 110


<210> SEQ ID NO 11
<211> LENGTH: 199
<212> TYPE: PRT
<213> ORGANISM: Homo sapiens

<400> SEQUENCE: 11

Gln Ala Ala Ala Pro Pro Lys Ala Val Leu Lys Leu Glu Pro Pro Trp
1               5                   10                  15

Ile Asn Val Leu Gln Glu Asp Ser Val Thr Leu Thr Cys Gln Gly Ala
            20                  25                  30

Arg Ser Pro Glu Ser Asp Ser Ile Gln Trp Phe His Asn Gly Asn Leu
        35                  40                  45

Ile Pro Thr His Thr Gln Pro Ser Tyr Arg Phe Lys Ala Asn Asn Asn
    50                  55                  60

Asp Ser Gly Glu Tyr Thr Cys Gln Thr Gly Gln Thr Ser Leu Ser Asp
65                  70                  75                  80

Pro Val His Leu Thr Val Leu Ser Glu Trp Leu Val Leu Gln Thr Pro
                85                  90                  95

His Leu Glu Phe Gln Glu Gly Glu Thr Ile Met Leu Arg Cys His Ser
            100                 105                 110

Trp Lys Asp Lys Pro Leu Val Lys Val Thr Phe Phe Gln Asn Gly Lys
        115                 120                 125

Ser Gln Lys Phe Ser His Leu Asp Pro Thr Phe Ser Ile Pro Gln Ala
    130                 135                 140

Asn His Ser His Ser Gly Asp Tyr His Cys Thr Gly Asn Ile Gly Tyr
145                 150                 155                 160

Thr Leu Phe Ser Ser Lys Pro Val Thr Ile Thr Val Gln Val Pro Ser
                165                 170                 175

Met Gly Ser Ser Ser Pro Met Gly Ala His His His His His His Asp
            180                 185                 190

Tyr Lys Asp Asp Asp Asp Lys
        195


<210> SEQ ID NO 12
<211> LENGTH: 199
<212> TYPE: PRT
<213> ORGANISM: Homo sapiens

<400> SEQUENCE: 12

Gln Ala Ala Ala Pro Pro Lys Ala Val Leu Lys Leu Glu Pro Pro Trp
1               5                   10                  15

Ile Asn Val Leu Gln Glu Asp Ser Val Thr Leu Thr Cys Gln Gly Ala
            20                  25                  30
```

```
Arg Ser Pro Glu Ser Asp Ser Ile Gln Trp Phe His Asn Gly Asn Leu
        35                  40                  45

Ile Pro Thr His Thr Gln Pro Ser Tyr Arg Phe Lys Ala Asn Asn Asn
    50                  55                  60

Asp Ser Gly Glu Tyr Thr Cys Gln Thr Gly Gln Thr Ser Leu Ser Asp
65                  70                  75                  80

Pro Val His Leu Thr Val Leu Ser Glu Trp Leu Val Leu Gln Thr Pro
                85                  90                  95

His Leu Glu Phe Gln Glu Gly Glu Thr Ile Met Leu Arg Cys His Ser
            100                 105                 110

Trp Lys Asp Lys Pro Leu Val Lys Val Thr Phe Phe Gln Asn Gly Lys
        115                 120                 125

Ser Gln Lys Phe Ser Arg Leu Asp Pro Thr Phe Ser Ile Pro Gln Ala
    130                 135                 140

Asn His Ser His Ser Gly Asp Tyr His Cys Thr Gly Asn Ile Gly Tyr
145                 150                 155                 160

Thr Leu Phe Ser Ser Lys Pro Val Thr Ile Thr Val Gln Val Pro Ser
                165                 170                 175

Met Gly Ser Ser Ser Pro Met Gly Ala His His His His His His Asp
            180                 185                 190

Tyr Lys Asp Asp Asp Asp Lys
        195
```

<210> SEQ ID NO 13
<211> LENGTH: 197
<212> TYPE: PRT
<213> ORGANISM: Homo sapiens

<400> SEQUENCE: 13

```
Thr Pro Ala Ala Pro Pro Lys Ala Val Leu Lys Leu Glu Pro Gln Trp
1               5                   10                  15

Ile Asn Val Leu Gln Glu Asp Ser Val Thr Leu Thr Cys Arg Gly Thr
            20                  25                  30

His Ser Pro Glu Ser Asp Ser Ile Gln Trp Phe His Asn Gly Asn Leu
        35                  40                  45

Ile Pro Thr His Thr Gln Pro Ser Tyr Arg Phe Lys Ala Asn Asn Asn
    50                  55                  60

Asp Ser Gly Glu Tyr Thr Cys Gln Thr Gly Gln Thr Ser Leu Ser Asp
65                  70                  75                  80

Pro Val His Leu Thr Val Leu Ser Glu Trp Leu Val Leu Gln Thr Pro
                85                  90                  95

His Leu Glu Phe Gln Glu Gly Glu Thr Ile Val Leu Arg Cys His Ser
            100                 105                 110

Trp Lys Asp Lys Pro Leu Val Lys Val Thr Phe Phe Gln Asn Gly Lys
        115                 120                 125

Ser Lys Lys Phe Ser Arg Ser Asp Pro Asn Phe Ser Ile Pro Gln Ala
    130                 135                 140

Asn His Ser His Ser Gly Asp Tyr His Cys Thr Gly Asn Ile Gly Tyr
145                 150                 155                 160

Thr Leu Tyr Ser Ser Lys Pro Val Thr Ile Thr Val Gln Ala Pro Ser
                165                 170                 175

Ser Ser Pro Met Gly Gly Ala His His His His His His Asp Tyr Lys
            180                 185                 190

Asp Asp Asp Asp Lys
        195
```

<210> SEQ ID NO 14
<211> LENGTH: 189
<212> TYPE: PRT
<213> ORGANISM: Macaca fascicularis

<400> SEQUENCE: 14

```
Gln Thr Ala Pro Pro Lys Ala Val Leu Lys Leu Glu Pro Pro Trp Ile
1               5                   10                  15

Asn Val Leu Arg Glu Asp Ser Val Thr Leu Thr Cys Gly Gly Ala His
            20                  25                  30

Ser Pro Asp Ser Asp Ser Thr Gln Trp Phe His Asn Gly Asn Arg Ile
        35                  40                  45

Pro Thr His Thr Gln Pro Ser Tyr Arg Phe Lys Ala Asn Asn Asn Asp
    50                  55                  60

Ser Gly Glu Tyr Arg Cys Gln Thr Gly Arg Thr Ser Leu Ser Asp Pro
65                  70                  75                  80

Val His Leu Thr Val Leu Ser Glu Trp Leu Ala Leu Gln Thr Pro His
                85                  90                  95

Leu Glu Phe Arg Glu Gly Glu Thr Ile Met Leu Arg Cys His Ser Trp
            100                 105                 110

Lys Asp Lys Pro Leu Ile Lys Val Thr Phe Phe Gln Asn Gly Ile Ala
        115                 120                 125

Lys Lys Phe Ser His Met Asn Pro Asn Phe Ser Ile Pro Gln Ala Asn
    130                 135                 140

His Ser His Ser Gly Asp Tyr His Cys Thr Gly Asn Ile Gly Tyr Thr
145                 150                 155                 160

Pro Tyr Ser Ser Lys Pro Val Thr Ile Thr Val Gln Val Pro Ser Val
                165                 170                 175

Gly Ser Ser Ser Pro Met Gly His His His His His His
            180                 185
```

<210> SEQ ID NO 15
<211> LENGTH: 189
<212> TYPE: PRT
<213> ORGANISM: Macaca fascicularis

<400> SEQUENCE: 15

```
Gln Thr Ala Pro Pro Lys Ala Val Leu Lys Leu Glu Pro Pro Trp Ile
1               5                   10                  15

Asn Val Leu Arg Glu Asp Ser Val Thr Leu Thr Cys Gly Gly Ala His
            20                  25                  30

Ser Pro Asp Ser Asp Ser Thr Gln Trp Phe His Asn Gly Asn Arg Ile
        35                  40                  45

Pro Thr His Thr Gln Pro Ser Tyr Arg Phe Lys Ala Asn Asn Asn Asp
    50                  55                  60

Ser Gly Glu Tyr Arg Cys Gln Thr Gly Arg Thr Ser Leu Ser Asp Pro
65                  70                  75                  80

Val His Leu Thr Val Leu Ser Glu Trp Leu Ala Leu Gln Thr Pro His
                85                  90                  95

Leu Glu Phe Arg Glu Gly Glu Thr Ile Met Leu Arg Cys His Ser Trp
            100                 105                 110

Lys Asp Lys Pro Leu Ile Lys Val Thr Phe Phe Gln Asn Gly Ile Ala
        115                 120                 125

Lys Lys Phe Ser Pro Met Asn Pro Asn Phe Ser Ile Pro Gln Ala Asn
    130                 135                 140
```

```
His Ser His Ser Gly Asp Tyr His Cys Thr Gly Asn Ile Gly Tyr Thr
145                 150                 155                 160

Pro Tyr Ser Ser Lys Pro Val Thr Ile Thr Val Gln Val Pro Ser Val
                165                 170                 175

Gly Ser Ser Ser Pro Met Gly His His His His His His
            180                 185


<210> SEQ ID NO 16
<211> LENGTH: 189
<212> TYPE: PRT
<213> ORGANISM: Macaca fascicularis

<400> SEQUENCE: 16

Gln Thr Ala Pro Pro Lys Ala Val Leu Lys Leu Glu Pro Pro Trp Ile
1               5                   10                  15

Asn Val Leu Arg Glu Asp Ser Val Thr Leu Thr Cys Gly Gly Ala His
            20                  25                  30

Ser Pro Asp Ser Asp Ser Thr Gln Trp Phe His Asn Gly Asn Arg Ile
        35                  40                  45

Pro Thr His Thr Gln Pro Ser Tyr Arg Phe Lys Ala Asn Asn Asn Asp
    50                  55                  60

Ser Gly Glu Tyr Arg Cys Gln Thr Gly Arg Thr Ser Leu Ser Asp Pro
65                  70                  75                  80

Val His Leu Thr Val Leu Ser Glu Trp Leu Ala Leu Gln Thr Pro His
                85                  90                  95

Leu Glu Phe Arg Glu Gly Glu Thr Ile Met Leu Arg Cys His Ser Trp
            100                 105                 110

Lys Asp Lys Pro Leu Ile Lys Val Thr Phe Phe Gln Asn Gly Ile Ala
        115                 120                 125

Lys Lys Phe Ser His Met Asp Pro Asn Phe Ser Ile Pro Gln Ala Asn
    130                 135                 140

His Ser His Ser Gly Asp Tyr His Cys Thr Gly Asn Ile Gly Tyr Thr
145                 150                 155                 160

Pro Tyr Ser Ser Lys Pro Val Thr Ile Thr Val Gln Val Pro Ser Val
                165                 170                 175

Gly Ser Ser Ser Pro Met Gly His His His His His His
            180                 185


<210> SEQ ID NO 17
<211> LENGTH: 188
<212> TYPE: PRT
<213> ORGANISM: Macaca fascicularis

<400> SEQUENCE: 17

Thr Pro Ala Ala Pro Pro Lys Ala Val Leu Lys Leu Glu Pro Pro Trp
1               5                   10                  15

Ile Asn Val Leu Arg Glu Asp Ser Val Thr Leu Thr Cys Gly Gly Ala
            20                  25                  30

His Ser Pro Asp Ser Asp Ser Thr Gln Trp Phe His Asn Gly Asn Leu
        35                  40                  45

Ile Pro Thr His Thr Gln Pro Ser Tyr Arg Phe Lys Ala Asn Asn Asn
    50                  55                  60

Asp Ser Gly Glu Tyr Arg Cys Gln Thr Gly Arg Thr Ser Leu Ser Asp
65                  70                  75                  80

Pro Val His Leu Thr Val Leu Ser Glu Trp Leu Ala Leu Gln Thr Pro
                85                  90                  95
```

```
His Leu Glu Phe Arg Glu Gly Glu Thr Ile Met Leu Arg Cys His Ser
            100                 105                 110

Trp Lys Asp Lys Pro Leu Ile Lys Val Thr Phe Phe Gln Asn Gly Ile
        115                 120                 125

Ser Lys Lys Phe Ser His Met Asn Pro Asn Phe Ser Ile Pro Gln Ala
    130                 135                 140

Asn His Ser His Ser Gly Asp Tyr His Cys Thr Gly Asn Ile Gly Tyr
145                 150                 155                 160

Thr Pro Tyr Ser Ser Lys Pro Val Thr Ile Thr Val Gln Val Pro Ser
                165                 170                 175

Met Gly Ser Ser Ser Pro His His His His His His
            180                 185


<210> SEQ ID NO 18
<211> LENGTH: 14
<212> TYPE: PRT
<213> ORGANISM: Artificial Sequence
<220> FEATURE:
<223> OTHER INFORMATION: His-Flag tag

<400> SEQUENCE: 18

His His His His His His Asp Tyr Lys Asp Asp Asp Asp Lys
1               5                   10


<210> SEQ ID NO 19
<211> LENGTH: 17
<212> TYPE: PRT
<213> ORGANISM: Artificial Sequence
<220> FEATURE:
<223> OTHER INFORMATION: HCDR2 for clones 32L00352, 32L00350 and
      32L00355

<400> SEQUENCE: 19

Trp Leu Asn Thr Tyr Thr Gly Glu Ser Trp Tyr Pro Asp Asp Phe Lys
1               5                   10                  15

Gly


<210> SEQ ID NO 20
<211> LENGTH: 17
<212> TYPE: PRT
<213> ORGANISM: Artificial Sequence
<220> FEATURE:
<223> OTHER INFORMATION: HCDR2 for clones 32L00351, 32L00354 and
      32L00356

<400> SEQUENCE: 20

Trp Leu Asn Thr Tyr Thr Gly Glu Ser Tyr Tyr Pro Asp Asp Phe Lys
1               5                   10                  15

Gly


<210> SEQ ID NO 21
<211> LENGTH: 17
<212> TYPE: PRT
<213> ORGANISM: Artificial Sequence
<220> FEATURE:
<223> OTHER INFORMATION: HCDR2 for IV.3 and Cam IV.3

<400> SEQUENCE: 21

Trp Leu Asn Thr Tyr Thr Gly Glu Ser Ile Tyr Pro Asp Asp Phe Lys
1               5                   10                  15

Gly
```

<210> SEQ ID NO 22
<211> LENGTH: 16
<212> TYPE: PRT
<213> ORGANISM: Artificial Sequence
<220> FEATURE:
<223> OTHER INFORMATION: LCDR1 for clone 32LO0352

<400> SEQUENCE: 22

```
Arg Ser Ser Lys Ser Leu Leu His Thr Asn Gln Asn Thr Tyr Leu His
1               5                   10                  15
```

<210> SEQ ID NO 23
<211> LENGTH: 16
<212> TYPE: PRT
<213> ORGANISM: Artificial Sequence
<220> FEATURE:
<223> OTHER INFORMATION: LCDR1 for clones 32LO0350 and 32LO0354

<400> SEQUENCE: 23

```
Arg Ser Ser Lys Ser Leu Leu His Thr Asn Arg Asn Thr Tyr Leu His
1               5                   10                  15
```

<210> SEQ ID NO 24
<211> LENGTH: 16
<212> TYPE: PRT
<213> ORGANISM: Artificial Sequence
<220> FEATURE:
<223> OTHER INFORMATION: LCDR1 for clone 32LO0355

<400> SEQUENCE: 24

```
Arg Ser Ser Lys Ser Leu Leu His Thr Asn Lys Asn Thr Tyr Leu His
1               5                   10                  15
```

<210> SEQ ID NO 25
<211> LENGTH: 16
<212> TYPE: PRT
<213> ORGANISM: Artificial Sequence
<220> FEATURE:
<223> OTHER INFORMATION: LCDR1 for clone 32LO0351

<400> SEQUENCE: 25

```
Arg Ser Ser Lys Ser Leu Leu His Thr Tyr Gly Asn Thr Tyr Leu His
1               5                   10                  15
```

<210> SEQ ID NO 26
<211> LENGTH: 16
<212> TYPE: PRT
<213> ORGANISM: Artificial Sequence
<220> FEATURE:
<223> OTHER INFORMATION: LCDR1 for clone 32LO0356

<400> SEQUENCE: 26

```
Arg Ser Ser Lys Ser Leu Leu His Thr Asn Phe Asn Thr Tyr Leu His
1               5                   10                  15
```

<210> SEQ ID NO 27
<211> LENGTH: 16
<212> TYPE: PRT
<213> ORGANISM: Artificial Sequence
<220> FEATURE:
<223> OTHER INFORMATION: LCDR1 for Cam IV.3

<400> SEQUENCE: 27

```
Arg Ser Ser Lys Ser Leu Leu His Thr Leu Gly Asn Thr Tyr Leu His
1               5                   10                  15
```

<210> SEQ ID NO 28
<211> LENGTH: 16
<212> TYPE: PRT
<213> ORGANISM: Artificial Sequence
<220> FEATURE:
<223> OTHER INFORMATION: LCDR1 for IV.3

<400> SEQUENCE: 28

Arg Ser Ser Lys Ser Leu Leu His Thr Asn Gly Asn Thr Tyr Leu His
1               5                   10                  15

<210> SEQ ID NO 29
<211> LENGTH: 5
<212> TYPE: PRT
<213> ORGANISM: Artificial Sequence
<220> FEATURE:
<223> OTHER INFORMATION: HCDR1 for IV. 3, Cam IV.3, and clones 32LO0352, 32LO0350, 32LO0355, 32LO0351, 32LO0354 and 32LO0356

<400> SEQUENCE: 29

Asn Tyr Gly Met Asn
1               5

<210> SEQ ID NO 30
<211> LENGTH: 10
<212> TYPE: PRT
<213> ORGANISM: Artificial Sequence
<220> FEATURE:
<223> OTHER INFORMATION: HCDR3 for IV. 3, Cam IV.3, and clones 32LO0352, 32LO0350, 32LO0355, 32LO0351, 32LO0354 and 32LO0356

<400> SEQUENCE: 30

Asp Tyr Gly Tyr Asp Asp Pro Leu Asp Tyr
1               5                   10

<210> SEQ ID NO 31
<211> LENGTH: 7
<212> TYPE: PRT
<213> ORGANISM: Artificial Sequence
<220> FEATURE:
<223> OTHER INFORMATION: LCDR2 for IV. 3, Cam IV.3, and clones 32LO0352, 32LO0350, 32LO0355, 32LO0351, 32LO0354 and 32LO0356

<400> SEQUENCE: 31

Arg Met Ser Val Leu Ala Ser
1               5

<210> SEQ ID NO 32
<211> LENGTH: 9
<212> TYPE: PRT
<213> ORGANISM: Artificial Sequence
<220> FEATURE:
<223> OTHER INFORMATION: LCDR3 for IV. 3, Cam IV.3, and clones 32LO0352, 32LO0350, 32LO0355, 32LO0351, 32LO0354 and 32LO0356

<400> SEQUENCE: 32

Met Gln His Leu Glu Tyr Pro Leu Thr
1               5

<210> SEQ ID NO 33
<211> LENGTH: 120
<212> TYPE: PRT
<213> ORGANISM: Artificial Sequence
<220> FEATURE:
<223> OTHER INFORMATION: VH domain for clone 32LO0352

<400> SEQUENCE: 33

Gln Val Gln Leu Val Gln Ser Gly Ala Glu Val Lys Lys Pro Gly Ala

```
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Arg Leu Glu Trp Met
        35                  40                  45

Gly Trp Leu Asn Thr Tyr Thr Gly Glu Ser Trp Tyr Pro Asp Asp Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Gly Tyr Asp Asp Pro Leu Asp Tyr Trp Gly Gln
            100                 105                 110

Gly Thr Leu Val Thr Val Ser Ser
        115                 120


<210> SEQ ID NO 34
<211> LENGTH: 112
<212> TYPE: PRT
<213> ORGANISM: Artificial Sequence
<220> FEATURE:
<223> OTHER INFORMATION: VL domian for 32LO0352

<400> SEQUENCE: 34

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Asn Gln Asn Thr Tyr Leu His Trp Phe Leu Gln Lys Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110


<210> SEQ ID NO 35
<211> LENGTH: 120
<212> TYPE: PRT
<213> ORGANISM: Artificial Sequence
<220> FEATURE:
<223> OTHER INFORMATION: VH domain for clone 32LO0350

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Arg Leu Glu Trp Met
        35                  40                  45

Gly Trp Leu Asn Thr Tyr Thr Gly Glu Ser Trp Tyr Pro Asp Asp Phe
    50                  55                  60

Lys Gly Arg Val Thr Ile Thr Arg Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Asp Tyr Gly Tyr Asp Asp Pro Leu Asp Tyr Trp Gly Gln
            100                 105                 110

Gly Thr Leu Val Thr Val Ser Ser
        115                 120
```

<210> SEQ ID NO 36
<211> LENGTH: 112
<212> TYPE: PRT
<213> ORGANISM: Artificial Sequence
<220> FEATURE:
<223> OTHER INFORMATION: VL domain for clone 32LO0350

<400> SEQUENCE: 36

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Asn Arg Asn Thr Tyr Leu His Trp Phe Leu Gln Lys Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110
```

<210> SEQ ID NO 37
<211> LENGTH: 120
<212> TYPE: PRT
<213> ORGANISM: Artificial Sequence
<220> FEATURE:
<223> OTHER INFORMATION: VH domain for clone 32LO0355

<400> SEQUENCE: 37

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Arg Leu Glu Trp Met
        35                  40                  45

Gly Trp Leu Asn Thr Tyr Thr Gly Glu Ser Trp Tyr Pro Asp Asp Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Gly Tyr Asp Asp Pro Leu Asp Tyr Trp Gly Gln
            100                 105                 110

Gly Thr Leu Val Thr Val Ser Ser
        115                 120
```

<210> SEQ ID NO 38
<211> LENGTH: 112
<212> TYPE: PRT
<213> ORGANISM: Artificial Sequence
<220> FEATURE:
<223> OTHER INFORMATION: VL domain for 32L00355

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Asn Lys Asn Thr Tyr Leu His Trp Phe Leu Gln Lys Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

<210> SEQ ID NO 39
<211> LENGTH: 120
<212> TYPE: PRT
<213> ORGANISM: Artificial Sequence
<220> FEATURE:
<223> OTHER INFORMATION: VH domain for clone 32L00351

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Arg Leu Glu Trp Met
        35                  40                  45

Gly Trp Leu Asn Thr Tyr Thr Gly Glu Ser Tyr Tyr Pro Asp Asp Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Gly Tyr Asp Asp Pro Leu Asp Tyr Trp Gly Gln
            100                 105                 110

Gly Thr Leu Val Thr Val Ser Ser
        115                 120

<210> SEQ ID NO 40
<211> LENGTH: 112
<212> TYPE: PRT
<213> ORGANISM: Artificial Sequence
<220> FEATURE:
<223> OTHER INFORMATION: VL domain for clone 32L00351

<400> SEQUENCE: 40

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Tyr Gly Asn Thr Tyr Leu His Trp Phe Leu Gln Lys Pro Gly Gln Ser
        35                  40                  45

-continued

```
Pro Gln Leu Leu Ile Tyr Arg Met Ser Val Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110


<210> SEQ ID NO 41
<211> LENGTH: 120
<212> TYPE: PRT
<213> ORGANISM: Artificial Sequence
<220> FEATURE:
<223> OTHER INFORMATION: VH domain for clone 32LO0354

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Arg Leu Glu Trp Met
        35                  40                  45

Gly Trp Leu Asn Thr Tyr Thr Gly Glu Ser Tyr Tyr Pro Asp Asp Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Gly Tyr Asp Asp Pro Leu Asp Tyr Trp Gly Gln
            100                 105                 110

Gly Thr Leu Val Thr Val Ser Ser
        115                 120


<210> SEQ ID NO 42
<211> LENGTH: 112
<212> TYPE: PRT
<213> ORGANISM: Artificial Sequence
<220> FEATURE:
<223> OTHER INFORMATION: VL domain for clone 32LO0354

<400> SEQUENCE: 42

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Asn Arg Asn Thr Tyr Leu His Trp Phe Leu Gln Lys Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110


<210> SEQ ID NO 43
```

-continued

<211> LENGTH: 120
<212> TYPE: PRT
<213> ORGANISM: Artificial Sequence
<220> FEATURE:
<223> OTHER INFORMATION: VH domain for clone 32LO0356

<400> SEQUENCE: 43

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Gly Met Asn Trp Val Arg Gln Ala Pro Gly Gln Arg Leu Glu Trp Met
35 40 45

Gly Trp Leu Asn Thr Tyr Thr Gly Glu Ser Tyr Tyr Pro Asp Asp Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Gly Asp Tyr Gly Tyr Asp Asp Pro Leu Asp Tyr Trp Gly Gln
100 105 110

Gly Thr Leu Val Thr Val Ser Ser
115 120

<210> SEQ ID NO 44
<211> LENGTH: 112
<212> TYPE: PRT
<213> ORGANISM: Artificial Sequence
<220> FEATURE:
<223> OTHER INFORMATION: VL domain for clone 32LO0356

<400> SEQUENCE: 44

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Thr
20 25 30

Asn Phe Asn Thr Tyr Leu His Trp Phe Leu Gln Lys Pro Gly Gln Ser
35 40 45

Pro Gln Leu Leu Ile Tyr Arg Met Ser Val Leu Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln His
85 90 95

Leu Glu Tyr Pro Leu Thr Phe Gly Gln Gly Thr Lys Leu Glu Ile Lys
100 105 110

<210> SEQ ID NO 45
<211> LENGTH: 11
<212> TYPE: PRT
<213> ORGANISM: Artificial Sequence
<220> FEATURE:
<223> OTHER INFORMATION: HCDR3 for IV. 3, Cam IV.3, and clones 32LO0352,
32LO0350, 32LO0355, 32LO0351, 32LO0354 and 32LO0356

<400> SEQUENCE: 45

Gly Asp Tyr Gly Tyr Asp Asp Pro Leu Asp Tyr
1 5 10

BINDING MOLECULES SPECIFIC FOR FCγRIIA AND USES THEREOF

CROSS-REFERENCE TO RELATED APPLICATIONS

This application is a Continuation of U.S. patent application Ser. No. 16/097,573, now U.S. Pat. No. 11,306,145, filed Oct. 29, 2018, which is the U.S. National Stage of International Patent Application No. PCT/EP2017/060188, filed Apr. 28, 2017, which claims the benefit of priority to U.S. Provisional Application No. 62/349,804, filed Jun. 14, 2016 and U.S. Provisional Application No. 62/329,627, filed Apr. 29, 2016, the contents of which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: HOPA-017_03US_SeqList_ST25.txt, date recorded: Mar. 1, 2022, file size 45 kilobytes).

BACKGROUND

FcγRs are a family of cell surface receptors that bind to the Fc portion of antibodies of the immunoglobulin G (IgG) subclasses. Human Fc gamma receptors (FcγRs) differ in function, binding affinity, and in their cellular distribution[1].

In humans, there are five FcγRs: the high-affinity receptor FcγRI (CD64), which can bind monomeric IgG; and the low-affinity receptors FcγRIIA (CD32A), FcγRIIB (CD32B), FcγRIIIA (CD16A), and FcγRIIIB (CD16B), which bind weakly to monomeric IgG, but avidly to immune complexes of IgG. FcγRI, FcγRIIA, FcγRIIIA, and FcγRIIIB are considered to have activating properties, whereas FcγRIIB is predominately inhibitory. FcγRIIA and FcγRIIB are the most closely related receptors. The extracellular regions of these receptors, which are responsible for interactions with IgG, share greater than 90% sequence identity. Sequence differences in the intracellular signaling regions of FcγRIIA and FcγRIIB mediate the alternative cellular responses.

FcγRs mediate several cellular processes, including antigen or pathogen uptake, degranulation, antigen presentation, and antibody-dependent cellular cytotoxicity (ADCC). In addition, FcγRs can interact with other receptors to influence the production of specific cytokines. Failure of the immune system to appropriately limit the reactivity of FcγRs can play a role in the development of inflammatory, immune-mediated, or autoimmune diseases or disorders[3].

Systemic lupus erythematosus (SLE) is a heterogeneous autoantibody driven immune-complex mediated autoimmune disease. A hallmark of SLE patients is the presence of autoantibodies directed against nuclear antigens, including dsDNA, ssDNA, and nucleic acid associated proteins (e.g., RNP, histones, Smith, Ro). Disease manifestations in the skin, lung, and kidney are associated with deposition of immune complexes[4]. Immune-complex-mediated activation of FcγRIIA has been implicated to play a role in the pathogenesis of SLE[5]. Approximately 60% of SLE patients have a type I interfereon (IFN) gene signature which is most prevalent in patients with severe disease activity. Importantly, immune complexes containing DNA and RNA induce plasmacytoid dendritic cells to produce type I IFNα in an FcγRIIA-dependent manner[5,6,7].

Anti-neutrophil cytoplasmic antibody (ANCA)-associated vasculitis (AAV) refers to a heterogeneous group of inflammatory diseases of blood vessels with multisystem manifestations[8]. AAV comprises granulomatosis with polyangiitis (GPA), microscopic polyangiitis (MPA), necrotizing crescentic glomerulonephritis (NCGN), and eosinophilic granulomatosis (EGPA). A hallmark of AAV patients is the presence of autoantibodies directly against neutrophil cytoplasmic antigens. The target antigens of ANCA include myeloperoxidase (MPO), proteinase 3 (PR3), lactoferrin, and others. GPA is primarily associated with antibodies to PR3, whereas MPA and EGPA are both associated with antibodies to MPO. ANCAs not only serve as a diagnostic marker, but they also play a direct pathogenic role in the disease. ANCAs can induce the direct activation of neutrophils via FcγRIIA, which can drive vascular injury[9]. Moreover, ANCAs may also trigger FcγRIIA-dependent induction of neutrophil extracellular traps (NETs), cytokines, and chemokines, which may contribute to inflammation and the autoimmune response[10]. Therefore, FcγRIIA appears to play a central role in the development and pathology of AAV.

Immune thrombocytopenia (ITP) is an autoimmune bleeding disorder characterized by the production of autoreactive antibodies directed against platelet antigens. Autoantibodies coating the surface of platelets promote their clearance by phagocytic macrophages of the reticuloendothelial system. The repertoire and cellular expression of FcγRs differ between mouse and human, and although FcγRII is the most broadly expressed FcγR in humans, it is absent in mice. Using mice, transgenic for human FcγRIIA and deficient for the murine activating FcγRs, it was demonstrated that passively administered anti-platelet antibodies triggered immune thrombocytopenia in an FcγRIIA-dependent manner[11]. In addition, significantly higher FcγRIIA/B ratio was observed on monocytes in patients with primary ITP; high-dose dexamethasone treatment, which is used as a first-line therapy for ITP patients, decreased the FcγRIIA/B ratio[12]. These in vitro and in vivo data indicate that human FcγRIIA plays a significant role in the pathogenesis of ITP.

The formation of neutrophil extracellular traps (NETs) are believed to be important in host defense against bacterial infections[17]. Conversely, formation of NETs is also associated with detrimental effects such as thrombosis, inflammation and endothelial dysfunction[18,19,20]. In addition to their pathogenic role in ANCA-associated vasculitis, there is evidence to indicate that NETs may contribute to sepsis, thrombosis, acute kidney injury, acute lung injury, chronic obstructive pulmonary disease, glomerulonephritis, toxic liver injury, stroke, atherogenesis and Type I diabetes[21,22]. Since FcγRIIA plays a crucial role in the formation of NETs[10], blocking FcγRIIA may have a beneficial role in the treatment of NET-associated disorders.

Anti-drug antibodies (ADAs) can be elicited in vivo in response to a therapeutic antibody. In addition to the impact of ADAs on therapeutic exposure, the formation of immune complexes between the drug and ADAs can elicit potential harmful FcR-mediated hypersensitivity reactions[23]. Since FcγRIIA is the predominant activating FcγR that is responsible for immune complex-mediated effector functions, blocking FcγRIIA may be able to inhibit ADA-mediated adverse effects.

This disclosure provides compositions that specifically bind to FcγRIIA, and methods for the use of such compositions, such as for the treatment or prevention of an inflammatory, immune-mediated, or autoimmune disease or disorder.

SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

The disclosure provides FcγRIIA-binding molecules, for example, humanized monoclonal antibodies capable of inhibiting FcγRIIA activity, and methods of using the FcγRIIA binding molecules, for example, in treating or preventing inflammatory, immune-mediated, or autoimmune diseases or disorders.

In one aspect, the invention provides an isolated binding molecule that specifically binds to FcγRIIA, wherein the binding molecule comprises an immunoglobulin variable heavy chain complementarity determining region 2 (VH-CDR2) comprising an amino acid sequence selected from the group consisting of SEQ ID NO: 19 and SEQ ID NO: 20. In one aspect, the invention provides an isolated binding molecule that specifically binds to FcγRIIA, wherein the binding molecule comprises an immunoglobulin variable light chain complementarity determining region 1 (VL-CDR1) comprising an amino acid sequence selected from the group consisting of SEQ ID NO: 22, SEQ ID NO: 23, SEQ ID NO: 24, SEQ ID NO: 25, and SEQ ID NO: 26. In a particular aspect, a binding molecule of the invention comprises a VH-CDR2 and a VL-CDR1 comprising amino acid sequences: (i) SEQ ID NO: 19 and SEQ ID NO: 22; (ii) SEQ ID NO: 19 and SEQ ID NO: 23; (iii) SEQ ID NO: 19 and SEQ ID NO: 24; (iv) SEQ ID NO: 20 and SEQ ID NO: 25; (v) SEQ ID NO: 20 and SEQ ID NO: 23; or (vi) SEQ ID NO: 20 and SEQ ID NO: 26, respectively.

The invention provides an isolated binding molecule that specifically binds to FcγRIIA, wherein the binding molecule comprises: (a) an immunoglobulin variable heavy chain complementarity determining region 2 (VH-CDR2) and an immunoglobulin variable light chain complementarity determining region 1 (VL-CDR1) comprising amino acid sequences: (i) SEQ ID NO: 19 and SEQ ID NO: 22; (ii) SEQ ID NO: 19 and SEQ ID NO: 23; (iii) SEQ ID NO: 19 and SEQ ID NO: 24; (iv) SEQ ID NO: 20 and SEQ ID NO: 25; (v) SEQ ID NO: 20 and SEQ ID NO: 23; or (vi) SEQ ID NO: 20 and SEQ ID NO: 26, respectively; (b) an immunoglobulin variable heavy chain complementarity determining region 1 (VH-CDR1) comprising SEQ ID NO: 29; (c) an immunoglobulin variable heavy chain complementarity determining region 3 (VH-CDR3) comprising SEQ ID NO: 30 or SEQ ID NO: 45; (d) an immunoglobulin variable light chain complementarity determining region 2 (VL-CDR2) comprising SEQ ID NO: 31; and (e) an immunoglobulin variable light chain complementarity determining region 3 (VL-CDR3) comprising SEQ ID NO: 32. In one embodiment, the binding molecule comprises SEQ ID NO: 19 and SEQ ID NO: 22.

In one embodiment, the binding molecule comprises a heavy chain variable (VH) region and a light chain variable (VL) region, comprising amino acid sequences selected from the group consisting of: (i) SEQ ID NO: 33 and SEQ ID NO: 34, (ii) SEQ ID NO: 35 and SEQ ID NO: 36, (iii) SEQ ID NO: 37 and SEQ ID NO: 38, (iv) SEQ ID NO: 39 and SEQ ID NO: 40, (v) SEQ ID NO: 41 and SEQ ID NO: 42, and (vi) SEQ ID NO: 43 and SEQ ID NO: 44, respectively. In one embodiment, the binding molecule comprises SEQ ID NO: 33 and SEQ ID NO: 34.

In another aspect, the invention provides an isolated binding molecule that competes or cross-competes with one or more of the binding molecules described above.

In some embodiments, the binding molecule of the invention is selected from a murine antibody, a human antibody, a humanized antibody, a chimeric antibody, monoclonal antibody, a polyclonal antibody, a recombinant antibody, a bi-specific antibody, a multi-specific antibody, and an antigen-binding fragment thereof.

In some embodiments, the binding molecule of the invention is selected from an Fv, an Fab, an F(ab')2, an Fab', a dsFv fragment, a single chain Fv (scFV), an sc(Fv)2, a disulfide-linked (dsFv), a diabody, a triabody, a tetrabody, a minibody, or a single chain antibody.

The binding molecule of the invention can comprise an immunoglobulin (Ig) heavy chain constant region. In one aspect, the constant region is a human IgG constant region.

In a particular embodiment, the constant region comprises amino acid substitutions at Kabat positions 234, 235, and 331, wherein: the amino acid at Kabat position 234 is substituted with Phenylalanine (F), the amino acid at Kabat position 235 is substituted with Glutamic acid (E), and the amino acid at Kabat position 331 is substituted with Serine (S).

In some embodiments, the constant region comprises one or more substitutions of amino acid residues at positions 251-257, 285-290, 308-314, 385-389, and 428-436, relative to a wild-type human IgG constant region, wherein the amino acid position numbering is according to the EU index as set forth in Kabat. In a particular embodiment, the constant region comprises amino acid substitutions at Kabat positions 252, 254, and 256, wherein: the amino acid at Kabat position 252 is substituted with Tyrosine (Y), the amino acid at Kabat position 254 is substituted with Threonine (T), and the amino acid at Kabat position 256 is substituted with Glutamic acid (E).

The binding molecule of the invention can comprise an immunoglobulin light chain constant region. In some embodiments, the light chain constant region is a human kappa constant region.

In one aspect, the binding molecule of the invention specifically binds human FcγRIIA 131R with an affinity characterized by a dissociation constant ($K_D$) of about 0.16 nM, as measured by a BIAcore assay. In another aspect, the binding molecule of the invention specifically binds human FcγRIIA 131H with an affinity characterized by a dissociation constant ($K_D$) of about 0.13 nM, as measured by a BIAcore assay. Preferably, the binding molecule does not specifically bind to FcγRI, FcγRIIB, or FcγRIII.

The binding molecule of the invention can be conjugated to an agent, for example, an agent selected from the group consisting of an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a polyethylene glycol (PEG), a toxin, and a combination of two or more of any said agents.

The invention further provides a composition comprising a binding molecule of the invention. In one embodiment, the composition is a diagnostic reagent.

In further embodiments, the invention provides a method for inhibiting ribonucleoprotein-immune complex (RNP-IC)-mediated type I IFNα in a peripheral blood mononuclear cell (PBMC), the method comprising contacting the PBMC with a binding molecule of the invention. Also provided is a method for inhibiting anti-neutrophil cytoplasmic antibody (ANCA)-induced neutrophil activation, the method comprising contacting a neutrophil with a binding molecule of the invention.

In some aspects, the invention provides a method of treating or preventing an inflammatory, immune-mediated, or autoimmune disease or disorder in a subject, the method comprising administering to a subject in need of treatment or to a subject susceptible to the disease or disorder an effective amount of a binding molecule or composition of the invention. The disease or disorder is preferably selected from ANCA-associated vasculitis (AAV), systemic lupus erythematosus (SLE), lupus nephritis, membranous nephritis, immune thrombocytopenia (ITP), rheumatoid arthritis, polymyositis, dermatomyositis, pemphigus, hemolytic anemia, mixed connective tissue disease, Sjögren's syndrome, scleroderma, sepsis, thrombosis, acute kidney injury, acute lung injury, chronic obstructive pulmonary disease, glomerulonephritis, toxic liver injury, stroke, atherogenesis and Type I diabetes, an autoantibody disorder, and an immune-complex-mediated disorder. In some embodiments, the method comprises administering a second active agent.

Further provided is a method for detecting FcγRIIA in a sample, the method comprising (a) contacting the sample with a binding molecule of the invention, and (b) detecting binding of the binding molecule to FcγRIIA, thereby detecting FcγRIIA in the sample. In some instances, the method is a diagnostic method.

In additional embodiments, the invention provides an isolated nucleic acid molecule comprising a nucleotide sequence encoding a binding molecule of the invention, optionally linked to a regulatory sequence; a host cell transformed with the nucleic acid molecule, preferably a mammalian host cell; and a vector comprising the nucleic acid molecule. Also provided is a composition comprising the nucleic acid molecule, host cell, or vector of the invention.

The invention provides a method of making a binding molecule that specifically binds FcγRIIA, the method comprising culturing the host cell of the invention under suitable conditions for producing the binding molecule. In some aspects, the method further comprises isolating the binding molecule.

In one embodiment, the invention provides a kit comprising a binding molecule or a nucleic acid molecule of the invention.

BRIEF DESCRIPTION OF THE DRAWINGS

FIGS. 1A-1C show consensus FcγRIIA cynomolgus sequences and alignments to human FcγRIIA. FIG. 1A shows the consensus amino acid sequence of cynomolgus FcγRIIA (SEQ ID NO: 1). Single nucleotide polymorphism (SNP) variants among cynomolgus populations are shown in bold type. Minor alleles corresponding to the major human allele are underlined. Shaded residues indicate minor allele frequency (MAF) of >20%. FIG. 1B shows alignment of human FcγRIIA (P12318; as 1-317; SEQ ID NO: 2) and cynomolgus FcγRIIA (SEQ ID NO: 3). Cyno amino acids that are non-homologous to human are shaded. Variations where the minor cyno allele corresponds to human are underlined. FIG. 1C shows the consensus FcγRIIA full-length cynomolgus transcript (SEQ ID NO: 4).

FIGS. 4A-4B show epitope competition assay data for a panel of humanized IV.3 antibodies. FIG. 4A shows binding to human FcγRIIA 131H. FIG. 4B shows binding to human FcγRIIA 131R.

FIG. 5A shows binding data for human FcγRIIA. FIG. 5B shows binding data for FcγRIIB FIG. 5C shows binding data for human FcγRI. FIG. 5D shows binding data for human FcγRIIIA-158F allotype. FIG. 5E shows binding data for human FcγRIIIA-158V allotype.

FIG. 13A shows the serum concentration of MEDI9600 in cynomolgus monkeys at various time points after a single dose. Flow cytometry analysis of blood cells from cynomolgus monkeys shows that MEDI9600 induced a dose-response reduction of FcγRIIA fluorescence intensity on monocytes (FIG. 13B) and granulocytes (FIG. 13C).

DETAILED DESCRIPTION OF THE INVENTION

Figure 2:
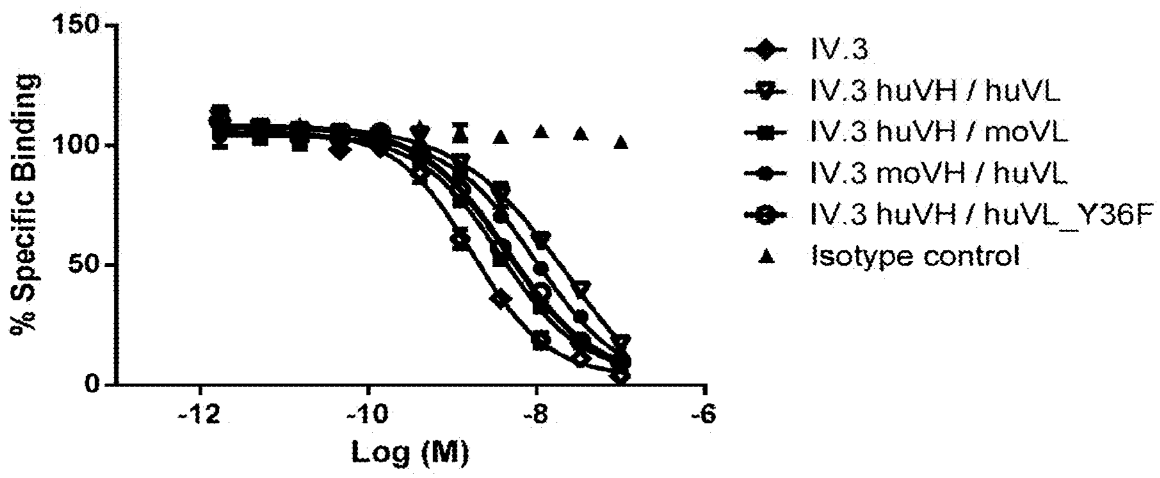
FIG. 2 shows epitope competition assay data for humanization of IV.3.

The present invention provides molecules that bind to FcγRIIA. In some embodiments, such molecules are antibodies or antigen-binding fragments thereof, which specifically bind to FcγRIIA. Related polynucleotides, compositions comprising the anti-FcγRIIA binding molecules, and methods of making the anti-FcγRIIA binding molecules are also provided. Methods of using the novel anti-FcγRIIA antibodies, such as diagnostic methods and methods of treating inflammatory, immune-mediated, or autoimmune disease or disorders are further provided.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Ausubel et al. eds. (2015) *Current Protocols in Molecular Biology* (John Wiley and Sons); Greenfield, ed. (2013) *Antibodies: A Laboratory Manual* (2nd ed., Cold Spring Harbor Press); Green and Sambrook, eds. (2012), *Molecular Cloning: A Laboratory Manual* (4th ed., Cold Spring Harbor Laboratory Press); Krebs et al., eds. (2012) *Lewin's Genes XI* (11th ed., Jones & Bartlett Learning); Freshney (2010) *Culture Of Animal Cells* (6th ed., Wiley); Weir and Blackwell, eds., (1996) *Handbook Of Experimental Immunology*, Volumes I-IV (5th ed., Wiley-Blackwell); Borrebaeck, ed. (1995) *Antibody Engineering* (2nd ed., Oxford Univ. Press); Glover and Hames, eds., (1995) *DNA Cloning: A Practical Approach*, Volumes I and II (2nd ed., IRL Press); Rees et al., eds. (1993) *Protein Engineering: A Practical Approach* (1st ed., IRL Press); Mayer and Walker, eds. (1987) *Immunochemical Methods In Cell And Molecular Biology* (Academic Press, London); Nisonoff (1984) *Introduction to Molecular Immunology* (2nd ed., Sinauer Associates, Inc.); and Steward (1984) *Antibodies: Their Structure and Function* (1st ed., Springer Netherlands).

In order that the present invention can be more readily understood, certain terms are first defined. Additional definitions are set forth throughout the disclosure. Unless defined otherwise, all technical and scientific terms used herein have the same meaning as commonly understood by one of ordinary skill in the art to which this invention is related. For example, *The Dictionary of Cell and Molecular Biology* (5th ed. J. M. Lackie ed., 2013), the *Oxford Dictionary of Biochemistry and Molecular Biology* (2d ed. R. Cammack et al. eds., 2008), and *The Concise Dictionary of Biomedicine and Molecular Biology* (2d ed. P-S. Juo, 2002) can provide one of skill with general definitions of some terms used herein.

I. Definitions

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation, and nucleic acid sequences are written left to right in 5' to 3' orientation. The headings provided herein are not limitations of the various aspects or embodiments of the invention, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are included.

Amino acids are referred to herein by their commonly known three-letter symbols or by the one-letter symbols recommended by the IUPAC-IUB Biochemical Nomenclature Commission. Nucleotides, likewise, are referred to by their commonly accepted single-letter codes.

"FcγRIIA" refers to Fc receptor-gamma IIA. The full-length amino acid and nucleotide sequences for human and cynomolgus monkey (*Macaca fascicular*i) FcγRIIA are known in the art. (See, e.g., FIG. 1.) The terms "FcγRIIA" and "CD32A" are used interchangeably throughout this disclosure. The terms "FcγRIIB" and "CD32B" are also used interchangeably throughout this disclosure, as are the terms "FcγRIIIA" and "CD16A," and "FcγRIIIB" and "CD16B," and "FcγRI" and "CD64," respectively.

The term "antibody" refers to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses polyclonal antibodies; monoclonal antibodies; multispecific antibodies, such as bispecific antibodies generated from at least two intact antibodies; humanized antibodies; human antibodies; chimeric antibodies; fusion proteins comprising an antigen-determination portion of an antibody; and any other modified immunoglobulin molecule comprising an antigen recognition site, so long as the antibodies exhibit the desired biological activity. Antibodies can be of any the five major classes of immunoglobulins: IgA, IgD, IgE, IgG and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu respectively. The different classes of immunoglobulins have different and well-known subunit structures and three-dimensional configurations. There are two classes of mammalian light chains, lambda and kappa. Antibodies can be naked or conjugated to other molecules such as toxins, radioisotopes, etc.

The term "antigen-binding fragment" refers to a portion of an intact antibody comprising the complementarity determining variable regions of the antibody. Fragments of a full-length antibody can be an antigen-binding fragment of an antibody. Examples of antibody fragments include, but are not limited to Fab, Fab', F(ab')2, and Fv fragments, linear antibodies, single chain antibodies (e.g., ScFvs), and multispecific antibodies formed from antibody fragments.

A "monoclonal antibody" (mAb) refers to a homogeneous antibody population that is involved in the highly specific recognition and binding of a single antigenic determinant, or epitope. This is in contrast to polyclonal antibodies, which typically include different antibodies directed against different antigenic determinants The term "monoclonal" can apply to both intact and full-length monoclonal antibodies, as well as to antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, *Nature,* 321:522-525; Riechmann et al., 1988, *Nature,* 332:323-327; Verhoeyen et al., 1988, *Science,* 239:1534-1536). In some instances, the Fv framework region (FW) residues of a human immunoglobulin are replaced with the corresponding residues in an antibody from a non-human species that has the desired specificity, affinity, and capability.

Humanized antibodies can be further modified by the substitution of additional residues either in the Fv framework region and/or within the replaced non-human residues to refine and optimize antibody specificity, affinity, and/or capability. In general, humanized antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641.

The term "human antibody" means an antibody produced by a human or an antibody having an amino acid sequence corresponding to an antibody produced by a human made using any technique known in the art. The definition of a human antibody includes intact or full-length antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

A "blocking" antibody or an "antagonist" antibody is one that inhibits or reduces biological activity of the antigen it binds, such as FcγRIIA. In certain aspects, blocking antibodies or antagonist antibodies substantially or completely inhibit the biological activity of the antigen. Desirably, the biological activity is reduced by 10%, 20%, 30%, 40%, 50%, 60%, 70%, 80%, 90%, 95%, or even 100%.

The term "germlining" means that amino acids at specific positions in an antibody are mutated back to those in the germ line.

The "IgG1 triple mutant" or "IgG1-TM" antibody format is a human IgG1 isotype containing three single amino acid substitutions, L234F/L235E/P331S, within the lower hinge and CH2 domain (Oganesyan et al., *Acta Crystallogr. D Biol. Crystallogr.* 64:700-704, 2008). The TM causes a profound decrease in binding to human FcγRI, FcγRII, FcγRIII, and C1q, resulting in a human isotype with very low effector function.

The terms "YTE" or "YTE mutant" refer to a mutation in IgG1 Fc that results in an increase in the binding to human FcRn and improves the serum half-life of the antibody having the mutation. A YTE mutant comprises a combination of three mutations, M252Y/S254T/T256E (EU numbering Kabat et al. (1991) Sequences of Proteins of Immunological Interest, U.S. Public Health Service, National Institutes of Health, Washington, D.C.), introduced into the heavy chain of an IgG1. See U.S. Pat. No. 7,658,921, which is incorporated by reference herein. The YTE mutant has been shown to increase the serum half-life of antibodies approximately four-times as compared to wild-type versions of the same antibody (Dall'Acqua et al., *J. Biol. Chem.* 281:23514-24 (2006); Robbie et al., *Antimicrob. Agents Chemother.* 57, 6147-6153 (2013)). See also U.S. Pat. No. 7,083,784, which is hereby incorporated by reference in its entirety.

The terms "antibody" or "immunoglobulin" are used interchangeably herein. A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region (CL). The light chain constant region is comprised of one domain, Cl. The variable regions of the heavy and light chains contain a binding domain that interacts with an antigen. The constant regions of the antibodies can mediate the binding of the immunoglobulin to host tissues or factors, including various cells of the immune system (e.g. effector cells) and the first component (C1q) of the classical complement system.

The VH and VL regions can be further subdivided into regions of hypervariability, termed complementarity-determining regions (CDRs), interspersed with regions that are more conserved, termed framework (FW) regions. The CDRs in each chain are held together in close proximity by the FW regions and, with the CDRs from the other chain, contribute to the formation of the antigen-binding site of antibodies. Each VH and VL is composed of three CDRs and four FWs, arranged from amino-terminus to carboxy-terminus in the following order: FW1, CDR1, FW2, CDR2, FW3, CDR3, FW4.

There are at least two techniques for determining CDRs: (1) an approach based on cross-species sequence variability (Kabat et al., *Sequences of Proteins of Immunological Interest,* 5th Ed. Public Health Service, National Institutes of Health, Bethesda, Md. (1991)); and (2) an approach based on crystallographic studies of antigen-antibody complexes (Al-lazikani et al., *J. Molec. Biol.* 273:927-948 (1997)). In addition, combinations of these two approaches are sometimes used in the art to determine CDRs.

The amino acid position numbering as in Kabat, refers to the numbering system used for heavy chain variable domains or light chain variable domains (approximately residues 1-107 of the light chain and residues 1-113 of the heavy chain). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a, according to Kabat) after residue 52 of H2 and inserted residues (e.g., residues 82a, 82b, and 82c, etc., according to Kabat) after heavy chain FW residue 82.

TABLE 1

| Loop | Kabat | AbM | Chothia |
| --- | --- | --- | --- |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. See Table 1.

IMGT (ImMunoGeneTics) also provides a numbering system for the immunoglobulin variable regions, including the CDRs. See, e.g., Lefranc, M. P. et al., *Dev. Comp. Immunol.* 27: 55-77 (2003). The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

As used throughout the specification the VH CDRs sequences described correspond to the classical Kabat numbering locations, namely Kabat VH-CDR1 is at positions 31-35, VH-CDR2 is a positions 50-65, and VH-CDR3 is at positions 95-102. VL-CDR1, VL-CDR2 and VL-CDR3 also correspond to classical Kabat numbering locations, namely positions 24-34, 50-56 and 89-97, respectively.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer.

The affinity or avidity of an antibody for an antigen can be determined experimentally using any suitable method known in the art, e.g., flow cytometry, enzyme-linked immunosorbent assay (ELISA), or radioimmunoassay (MA), or kinetics (e.g., KINEXA® or BIACORE™ analysis). Direct binding assays as well as competitive binding assay formats can be readily employed. (See, e.g., Berzofsky et al., "Antibody-Antigen Interactions," In *Fundamental Immunology*, Paul, W. E., ed., Raven Press: New York, N.Y. (1984); Kuby, *Immunology*, W. H. Freeman and Company: New York, N.Y. (1992)) The measured affinity of a particular antibody-antigen interaction can vary if measured under different conditions (e.g., salt concentration, pH, temperature). Thus, measurements of affinity and other antigen-binding parameters (e.g., $K_D$ or Kd, $K_{on}$, $K_{off}$) are made with standardized solutions of antibody and antigen, and a standardized buffer, as known in the art.

"Potency" is normally expressed as an $IC_{50}$ value, in nM or pM, unless otherwise stated. $IC_{50}$ is the median inhibitory concentration of an antibody molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by any number of means known in the art.

The fold improvement in potency for the antibodies or polypeptides of the invention as compared to a reference antibody can be at least about 2-fold, at least about 4-fold, at least about 6-fold, at least about 8-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

The terms "inhibit," "block," and "suppress" are used interchangeably and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity. Accordingly, when the terms "inhibition" or "suppression" are applied to describe, e.g., an effect on the FcγRIIA signal transduction pathway, the terms refer to the ability of an FcγRIIA binding molecule to statistically significantly decrease FcγRIIA-induced cell activation or signal transduction relative to an untreated (control) cell. The cell that expresses FcγRIIA can be a naturally occurring cell or cell line, (e.g., macrophage, neutrophil, eosinophil, platelet) or can be recombinantly produced by introducing a nucleic acid encoding FcγRIIA into a host cell. In one embodiment, the FcγRIIA binding molecule can inhibit FcγRIIA-mediated cell activation or signal transduction in an FcγRIIA-expressing cell by at least 10%, or at least 20%, or at least 30%, or at least 40%, or at least 50%, or at least 60%, or at least 70%, or at least 80%, or at least 90% or about 100%, as determined, for example, by flow cytometry, Western blotting, ELISA, or other assays known to those of skill in the art.

An "isolated" polypeptide, antibody, binding molecule, polynucleotide, vector, or cell is in a form not found in nature. Isolated polypeptides, antibodies, binding molecules, polynucleotides, vectors, or cells include those which have been purified to a degree that they are no longer in a form in which they are found in nature. In some embodiments, a polypeptide, antibody, binding molecule, polynucleotide, vector, or cell that is isolated is substantially pure. When used herein, the term "substantially pure" refers to purity of greater than 75%, preferably greater than 80% or 90%, and most preferably greater than 95%.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

The term "pharmaceutical composition" refers to a preparation that is in such form as to permit the biological activity of the active ingredient to be effective and which contains no additional components that are unacceptably toxic to a subject to which the composition would be administered. Such composition can be sterile and can comprise a pharmaceutically acceptable carrier, such as physiological saline. Suitable pharmaceutical compositions can comprise one or more of a buffer, a surfactant, a stabilizing agent, a preservative, an absorption promoter to enhance bioavailability and/or other conventional solubilizing or dispersing agents.

An "effective amount" of a binding molecule as disclosed herein is an amount sufficient to carry out a specifically stated purpose. An "effective amount" can be determined empirically and in a routine manner, in relation to the stated purpose.

The term "label" when used herein refers to a detectable compound or composition that is conjugated directly or indirectly to a binding molecule, so as to generate a "labeled" binding molecule. The label can be detectable by itself (e.g., radioisotope labels or fluorescent labels) or, as in the case of, e.g., an enzymatic label, can catalyze chemical alteration of a substrate compound or composition that is detectable.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already with the disorder. In certain embodiments, a subject is successfully "treated" for an inflammatory, immune-mediated, or autoimmune disease or disorder according to the methods provided herein if the patient shows, e.g., total, partial, or transient alleviation or elimination of symptoms associated with the disease or disorder.

"Prevent" or "prevention" refer to prophylactic or preventative measures that prevent and/or slow the development of a targeted pathologic condition or disorder. Thus, those in need of prevention include those prone to have or susceptible to the disorder. In certain embodiments, an inflammatory, immune-mediated, or autoimmune disease or disorder is successfully prevented according to the methods provided herein if the patient develops, transiently or permanently, e.g., fewer or less severe symptoms associated with the disease or disorder, or a later onset of symptoms associated with the disease or disorder, than a patient who has not been subject to the methods of the invention.

The terms "polypeptide," "peptide," and "protein" are used interchangeably herein to refer to polymers of amino acids of any length. The polymer can be linear or branched, it can comprise modified amino acids and non-amino acids can interrupt it. The terms also encompass an amino acid polymer that has been modified naturally or by intervention; for example, disulfide bond formation, glycosylation, lipidation, acetylation, phosphorylation or any other manipulation or modification such as conjugation with a labeling component. Also included within the definition are, for example, polypeptides containing one or more analogs of an amino acid (including, for example, unnatural amino acids, etc.), as well as other modifications known in the art. In certain embodiments, the polypeptides can occur as single chains or associated chains.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the amino acid sequences of the binding molecules of the invention do not abrogate the binding of the binding molecule to the antigen(s), i.e., FcγRIIA, to which the binding molecule binds. Methods of identifying conservative nucleotide and amino acid substitutions which do not eliminate antigen-binding are well-known in the art (see, e.g., Brummell et al., *Biochem.* 32: 1180-1187 (1993); Kobayashi et al., *Protein Eng.* 12(10): 879-884 (1999); and Burks et al., *Proc. Natl. Acad. Sci. U.S.A.* 94:412-417 (1997)).

A "polynucleotide," as used herein can include one or more "nucleic acids," "nucleic acid molecules," or "nucleic acid sequences," and refers to a polymer of nucleotides of any length, and includes DNA and RNA. The polynucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering and, in some embodiments expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

One such non-limiting example of a sequence alignment algorithm is the algorithm described in Karlin et al., *Proc. Natl. Acad. Sci.,* 87:2264-2268 (1990), as modified in Karlin et al., *Proc. Natl. Acad. Sci.,* 90:5873-5877 (1993), and incorporated into the NBLAST and) (BLAST programs (Altschul et al., *Nucleic Acids Res.,* 25:3389-3402 (1991)). In certain embodiments, Gapped BLAST can be used as described in Altschul et al., *Nucleic Acids Res.* 25:3389-

3402 (1997). BLAST-2, WU-BLAST-2 (Altschul et al., *Methods in Enzymology,* 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol*. (48):444-453 (1970)), can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS* 4:11-17 (1989)). For example, the percent identity can be determined using the ALIGN program (version 2.0) and using a PAM120 with residue table, a gap length penalty of 12 and a gap penalty of 4. One skilled in the art can determine appropriate parameters for maximal alignment by particular alignment software. In certain embodiments, the default parameters of the alignment software are used.

In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

II. FcγRIIA-Binding Molecules

The present invention provides FcγRIIA binding molecules, i.e., anti-FcγRIIA antibodies and antigen-binding fragments thereof, which specifically bind FcγRIIA. The term "FcγRIIA binding molecule" or "binding molecule that binds to FcγRIIA" or "anti-FcγRIIA" refers to a binding molecule that is capable of binding FcγRIIA with sufficient affinity such that the binding molecule is useful as a therapeutic agent or diagnostic reagent in targeting FcγRIIA. A binding molecule that "specifically binds to FcγRIIA" binds to an unrelated, non-FcγRIIA protein to an extent of less than about 10% of the binding of the binding molecule to FcγRIIA, as measured, e.g., by a radioimmunoassay (MA), BIACORE® (using recombinant FcγRIIA as the analyte and binding molecule as the ligand, or vice versa), KINEXA®, or other binding assays known in the art. In certain embodiments, binding molecule that binds to FcγRIIA has a dissociation constant ($K_D$) of <1 μM, <100 nM, <10 nM, <1 nM, <0.1 nM, <10 pM, <1 pM, or <0.1 pM.

Exemplary binding molecules of the present disclosure include variants of the mouse monoclonal antibody IV.3 (Looney R J. et al., *J. Immunol.* 136(5):1641 (1986)), including humanized, optimized, germlined, and/or other versions of these antibodies, anti-FcγRIIA™ antibodies, and serum half-life-optimized anti-FcγRIIA YTE antibodies (e.g., K44VHa-N56Q, K44VHa6-N56Q, or K2Ha-N56Q). Exemplary antibodies of the present disclosure include clones 32LO0350, 32LO0351, 32LO0352, 32LO0354, 32LO0355, and 32LO0356. "Clone 32LO0352" and "MEDI9600" refer to the same molecule and the terms are used interchangeably herein. The invention also embraces variants and equivalents that are substantially homologous to the FcγRIIA-binding molecules set forth herein. These can contain, for example, conservative amino acid substitutions.

In certain aspects, this disclosure provides an FcγRIIA binding molecule that can specifically bind to the same FcγRIIA epitope as a binding molecule comprising the heavy chain variable region (VH) and light chain variable region (VL) of any one of clones 32LO0350, 32LO0351, 32LO0352, 32LO0354, 32LO0355, or 32LO0356. The term "epitope" refers to a target protein determinant capable of binding to a binding molecule of the invention. Epitopes usually consist of chemically active surface groupings of molecules such as amino acids or sugar side chains, and usually have specific three-dimensional structural characteristics, as well as specific charge characteristics. Conformational and non-conformational epitopes are distinguished in that the binding to the former but not the latter is lost in the presence of denaturing solvents. Such binding molecules can be identified based on their ability to cross-compete (e.g., to competitively inhibit the binding of, in a statistically significant manner) with binding molecules such as clones 32LO0350, 32LO0351, 32LO0352, 32LO0354, 32LO0355, or 32LO0356, in standard FcγRIIA binding or activity assays.

Accordingly, in one embodiment, the invention provides FcγRIIA binding molecules that compete for binding to FcγRIIA with another FcγRIIA binding molecule of the invention, such as one of clones 32LO0350, 32LO0351, 32LO0352, 32LO0354, 32LO0355, or 32LO0356. The ability of a binding molecule to inhibit the binding of, e.g., clones 32LO0350, 32LO0351, 32LO0352, 32LO0354, 32LO0355, or 32LO0356, demonstrates that the test binding molecule can compete with clones 32LO0350, 32LO0351, 32LO0352, 32LO0354, 32LO0355, or 32LO0356 for binding to FcγRIIA; such a binding molecule can, according to non-limiting theory, bind to the same or a related (e.g., a structurally similar or spatially proximal) epitope on FcγRIIA as the FcγRIIA binding molecule with which it competes. In one embodiment, the anti-FcγRIIA antibody or antigen-binding fragment thereof that binds to the same epitope on FcγRIIA as any of clones 32LO0350, 32LO0351, 32LO0352, 32LO0354, 32LO0355, or 32LO0356. The term "competes" indicates that a binding molecule competes unidirectionally for binding to FcγRIIA with any one of 32LO0350, 32LO0351, 32LO0352, 32LO0354, 32LO0355, or 32LO0356. The term "cross-competes" indicates that a binding molecule competes bidirectionally for binding to FcγRIIA with any one of 32LO0350, 32LO0351, 32LO0352, 32LO0354, 32LO0355, or 32LO0356.

In some embodiments, the FcγRIIA binding molecule is a murine antibody, a human antibody, a humanized antibody, a chimeric antibody, a monoclonal antibody, a polyclonal antibody, a recombinant antibody, a bi-specific antibody, a multispecific antibody, or any combination thereof. In some embodiments, FcγRIIA binding molecules comprise a Fab, a Fab', a $F(ab')_2$, a Fd, a Fv, a scFv, a disulfide linked Fv, a V-NAR domain, an IgNar, an intrabody, an IgGΔCH2, a minibody, a $F(ab')_3$, a tetrabody, a triabody, a diabody, a single-domain antibody, DVD-Ig, Fcab, $mAb^2$, a $(scFv)_2$, or a scFv-Fc.

An FcγRIIA binding molecule provided herein can include, in addition to a VH and a VL, a heavy chain constant region or fragment thereof. In certain aspects the heavy chain constant region is a human heavy chain constant region, e.g., a human IgG constant region, e.g., a human IgG1 constant region.

In certain embodiments, binding molecules of the invention are produced to comprise an altered Fc region, in which one or more alterations have been made in the Fc region in order to change functional and/or pharmacokinetic properties of the binding molecule. Such alterations may result in altered effector function, reduced immunogenicity, and/or an increased serum half-life. The Fc region interacts with a number of ligands, including Fc receptors, the complement protein Clq, and other molecules, such as proteins A and G. These interactions are essential for a variety of effector functions and downstream signaling events including antibody dependent cell-mediated cytotoxicity (ADCC) and complement dependent cytotoxicity (CDC). Accordingly, in certain embodiments the FcγRIIA binding molecules of the invention have reduced or ablated affinity for an Fc ligand responsible for facilitating effector function, compared to an FcγRIIA binding molecule not comprising the modification in the Fc region. In particular embodiments, the FcγRIIA binding molecule has no ADCC activity and/or no CDC activity. In certain aspects, the FcγRIIA binding molecule does not bind to an Fc receptor and/or complement factors. In certain aspects, the FcγRIIA binding molecule has no effector function. Selecting particular constant domains to optimize desired effector functions is within the ordinary skill in the art. In some embodiments, the binding molecule is of the IgG1 subtype, and optionally comprises the TM format (L234F/L235E/P331S), as disclosed supra in the Definitions section.

In certain aspects, a heavy chain constant region or fragment thereof can include one or more amino acid substitutions relative to a wild-type IgG constant domain, wherein the modified IgG has an increased half-life compared to the half-life of an IgG having the wild-type IgG constant domain. For example, the IgG constant domain can contain one or more amino acid substitutions of amino acid residues at positions 251-257, 285-290, 308-314, 385-389, and 428-436, wherein the amino acid position numbering is according to the EU index as set forth in Kabat. In certain aspects the IgG constant domain can contain one or more of a substitution of the amino acid at Kabat position 252 with Tyrosine (Y), Phenylalanine (F), Tryptophan (W), or Threonine (T), a substitution of the amino acid at Kabat position 254 with Threonine (T), a substitution of the amino acid at Kabat position 256 with Serine (S), Arginine (R), Glutamine (Q), Glutamic acid (E), Aspartic acid (D), or Threonine (T), a substitution of the amino acid at Kabat position 257 with Leucine (L), a substitution of the amino acid at Kabat position 309 with Proline (P), a substitution of the amino acid at Kabat position 311 with Serine (S), a substitution of the amino acid at Kabat position 428 with Threonine (T), Leucine (L), Phenylalanine (F), or Serine (S), a substitution of the amino acid at Kabat position 433 with Arginine (R), Serine (S), Isoleucine (I), Proline (P), or Glutamine (Q), or a substitution of the amino acid at Kabat position 434 with Tryptophan (W), Methionine (M), Serine (S), Histidine (H), Phenylalanine (F), or Tyrosine. More specifically, the IgG constant domain can contain amino acid substitutions relative to a wild-type human IgG constant domain including as substitution of the amino acid at Kabat position 252 with Tyrosine (Y), a substitution of the amino acid at Kabat position 254 with Threonine (T), and a substitution of the amino acid at Kabat position 256 with Glutamic acid (E). In some embodiments, the binding molecule is of the IgG1 subtype, and optionally comprises the triple mutant YTE, as disclosed supra in the Definitions section.

An FcγRIIA binding molecule provided herein can include a light chain constant region or fragment thereof. In certain aspects the light chain constant region is a kappa constant region or a lambda constant region, e.g., a human kappa constant region or a human lambda constant region.

FcγRIIA binding molecules provided herein can have beneficial properties. For example, the binding molecule can inhibit, suppress, or block various FcγRIIA-mediated activities, e.g., immune-complex-induced type I interferon expression in plasmacytoid dendritic cells (DCs), immune-complex-induced cytokines/chemokines expression in DCs, immune-complex-induced platelet activation, immune-complex-induced antigen presentation, immune-complex-induced neutrophil extracellular traps (NETs) formation, and degranulation in neutrophil activation.

In certain aspects, the binding molecules provided herein can bind to FcγRIIA with a binding affinity characterized by a dissociation constant ($K_D$) of about 100 nM to about 0.1 nM as measured by a Biacore™ assay or on a Kinetic Exclusion Assay (KinExA) 3000 platform.

In certain aspects, an anti-FcγRIIA antibody or antigen-binding fragment thereof can specifically bind to FcγRIIA, e.g., human FcγRIIA or cynomolgus monkey FcγRIIA, or an antigenic fragment thereof, with a dissociation constant or $K_D$ of less than $10^{-6}$ M, of less than $10^{-7}$M, of less than $10^{-8}$ M, of less than $10^{-9}$M, of less than $10^{-10}$ M, of less than $10^{-11}$ M, of less than $10^{-12}$ M, of less than $10^{-13}$ M, of less than $10^{-14}$ M, or of less than $10^{-15}$ M as measured, e.g., by Biacore™ or KinExA®. In a particular aspect, the humanized anti-FcγRIIA antibody MEDI9600 can bind to human FcγRIIA (131R) with a $K_D$ of about 0.15 nM, to human FcγRIIA (131H) with a $K_D$ of about 0.13 nM, and to cynomolgus monkey FcγRIIA with a $K_D$ of about 31.3 nM, as measured by a BIAcore assay.

In another embodiment, an FcγRIIA binding molecule of the invention binds to FcγRIIA or an antigenic fragment thereof with a $K_{off}$ of less than $1\times10^{-3}$ $s^{-1}$, or less than $2\times10^{-3}$ $s^{-1}$. In other embodiments, an FcγRIIA binding molecule binds to FcγRIIA or an antigenic fragment thereof with a $K_{off}$ of less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$ as measured, e.g., by Biacore™ or KinExA®. In a particular aspect, the humanized anti-FcγRIIA antibody MEDI9600 can bind to human FcγRIIA (131R) with a $K_{off}$ of about $7.35\times10^{-4}$ $s^{-1}$, to human FcγRIIA (131H) with a $K_{off}$ of about $3.37\times10^{-4}$ $s^{-1}$, and to cynomolgus monkey FcγRIIA with a $K_{off}$ of about $9.04\times10^{-2}$ $s^{-1}$, as measured by a BIAcore assay.

In another embodiment, an FcγRIIA binding molecule of the invention binds to FcγRIIA or an antigenic fragment thereof with an association rate constant or $K_{on}$ rate of at least $10^5M^{-1}s^{-1}$, at least $5\times10^{-5}M^{-1}$ $s^{-1}$ at least $10^{-6}M^{-1}$ $s^{-1}$ at least $5\times10^{-6}M^{-1}$ $s^{-1}$ at least $10^{-7}M^{-1}$ $s^{-1}$, at least $5\times10^{-7}$ $M^{-1}$ $s^{-1}$, at least $10^{-8}M^{-1}$ $s^{-1}$, or at least $10^{-9}M^{-1}$ $s^{-1}$ as measured, e.g., by Biacore™ or KinExA®. In a particular aspect, the humanized anti-FcγRIIA antibody MEDI9600 can bind to human FcγRIIA (131R) with a $K_{on}$ of about $4.98\times10^6$ $M^{-1}$ $s^{-1}$, to human FcγRIIA (131H) with a $K_{on}$ of about $2.60\times10^6M^{-1}$ $s^{-1}$, and to cynomolgus monkey FcγRIIA with a $K_{on}$ of about $2.88\times10^6$ $M^{-1}$ $s^{-1}$, as measured by a BIAcore assay.

A VH and/or VL amino acid sequence or portion thereof, including a CDR sequence, can be, e.g., 85%, 90%, 95%, 96%, 97%, 98%, 99% or 100% similar to a sequence set forth herein, and/or comprise 0, 1, 2, 3, 4, 5 or more substitutions, e.g., conservative substitutions, relative to a sequence set forth herein, such as a sequence from any of clones 32LO0350, 32LO0351, 32LO0352, 32LO0354, 32LO0355, or 32LO0356. An FcγRIIA-binding molecule having VH and VL regions with a certain percent similarity to a VH region or VL region, or having one or more substitutions, e.g., conservative substitutions, can be obtained by mutagenesis (e.g., site-directed or PCR-mediated mutagenesis) of nucleic acid molecules encoding VH and/or VL regions described herein, followed by testing of the encoded altered binding molecule for binding to FcγRIIA, and optionally testing for retained function using the functional assays described herein.

The disclosure further provides an FcγRIIA binding molecule that is conjugated to a heterologous agent. In certain aspects, the agent can be an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a polyethylene glycol (PEG), or a combination of two or more of any said agents. Heteroconjugate anti-FcγRIIA antibodies are discussed in more detail elsewhere herein.

The term "binding molecule" includes antibodies and antigen-binding fragments thereof. In certain embodiments, the FcγRIIA-binding molecule is a polypeptide that is not an antibody. A variety of methods for identifying and producing non-antibody polypeptides that bind with high affinity to a protein target are known in the art. See, e.g., Skerra, *Curr. Opin. Biotechnol.* 18:295-304 (2007), Hosse et al., *Protein Science* 15:14-27 (2006), Gill et al., *Curr. Opin. Biotechnol.* 17:653-658 (2006), Nygren, *FEBS* 275:2668-76 (2008), and Skerra, *FEBS J.* 275:2677-83 (2008). In certain embodiments, phage display technology can been used to identify and/or produce an FcγRIIA-binding polypeptide. In certain embodiments, the polypeptide comprises a protein scaffold of a type selected from the group consisting of protein A, a lipocalin, a fibronectin domain, an ankyrin consensus repeat domain, and thioredoxin.

III. Preparation of FcγRIIA-Binding Molecules

Monoclonal anti-FcγRIIA antibodies can be prepared using hybridoma methods, such as those described by Kohler and Milstein *Nature* 256:495 (1975). Using the hybridoma method, a mouse, hamster, or other appropriate host animal, is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol (PEG), to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. RIA or ELISA) can then be propagated either in in vitro culture using standard methods (Goding, *Monoclonal Antibodies: Principles and Practice*, Academic Press, 1986) or in vivo as ascites tumors in an animal. The monoclonal antibodies can then be purified from the culture medium or ascites fluid.

FcγRIIA-binding molecules can also be made using recombinant DNA methods, for example, as described in U.S. Pat. No. 4,816,567. In some instances, the polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains or antigen-binding fragments thereof are then cloned into suitable expression vectors, which when transfected into host cells such as *E. coli* cells, simian COS cells, Chinese hamster ovary (CHO) cells, or myeloma cells that do not otherwise produce immunoglobulin protein, binding molecules are generated by the host cells. Also, recombinant FcγRIIA-binding molecules can be isolated from phage display libraries expressing CDRs of the desired species, as described by McCafferty et al. (*Nature,* 348:552-554 (1990)); Clackson et al. (*Nature,* 352:624-628 (1991)); and Marks et al. (*J. Mol. Biol.,* 222:581-597 (1991)). Production and expression of nucleic acids comprising nucleotide sequences encoding FcγRIIA-binding molecules are discussed in more detail in the next section.

The polynucleotide(s) encoding a binding molecule can further be modified in a number of different manners using recombinant DNA technology to generate alternative binding molecules. In some embodiments, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In certain embodiments, the FcγRIIA-binding molecule is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated (See, e.g., Cole et al., *Monoclonal Antibodies and Cancer Therapy*, Alan R. Liss, p. 77 (1985); Boemer et al., *J. Immunol.* 147 (1):86-95 (1991); and U.S. Pat. No. 5,750,373).

The FcγRIIA-binding molecule can be selected from a phage library, where the phage library expresses human antibodies, as described, for example, by Vaughan et al. (*Nat. Biotechnol.,* 14:309-314 (1996)), Sheets et al. (*Proc. Nat'l. Acad. Sci. U.S.A.* 95:6157-6162 (1998)), Hoogenboom et al. (*J. Mol. Biol.* 227:381 (1991)), and Marks et al. (*J. Mol. Biol.* 222:581 (1991)). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and in Rothe et al., *J. Mol. Biol.* 375:1182-1200 (2007).

Affinity maturation strategies and chain shuffling strategies are known in the art and can be employed to generate high affinity human antibodies or antigen-binding fragments thereof. (See Marks et al., *Bio/Technology* 10:779-783 (1992)).

In some embodiments, the FcγRIIA-binding molecule can be a humanized antibody or antigen-binding fragment thereof. Methods for engineering, humanizing, or resurfacing non-human or human antibodies can also be used and are well known in the art. A humanized, resurfaced, or similarly engineered antibody can have one or more amino acid residues from a source that is non-human, e.g., mouse, rat, rabbit, non-human primate, or other mammal. These non-human amino acid residues are replaced by residues that are often referred to as "import" residues, which are typically taken from an "import" variable, constant, or other domain of a known human sequence. Such imported sequences can be used to reduce immunogenicity or reduce, enhance, or modify binding, affinity, on-rate, off-rate, avidity, specificity, half-life, or any other suitable characteristic, as known in the art. In general, the CDR residues are directly and most substantially involved in influencing FcγRIIA binding. Accordingly, part or all of the non-human or human CDR sequences are maintained while the non-human sequences of the variable and constant regions can be replaced with human or other amino acids.

Antibodies can also optionally be humanized, resurfaced, engineered, or human antibodies engineered with retention of high affinity for FcγRIIA and other favorable biological properties. To achieve this goal, humanized (or human) or engineered anti-FcγRIIA antibodies and resurfaced antibodies can be optionally prepared by a process of analyzing the parental sequences and various conceptual humanized and engineered products, using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate binding molecule sequence, i.e., the analysis of residues that influence the ability of the candidate binding molecule to bind its target, such as FcγRIIA. In this way, framework (FW) residues can be selected and combined from the consensus and import sequences so that the desired binding molecule characteristic, such as increased affinity for the target, is achieved.

Humanization, resurfacing, or engineering of anti-FcγRIIA antibodies or antigen-binding fragments thereof can be performed using any known method, such as, but not limited to, those described in, Jones et al., *Nature* 321:522 (1986); Riechmann et al., *Nature* 332:323 (1988); Verhoeyen et al., *Science* 239:1534 (1988)), Sims et al., *J. Immunol.* 151: 2296 (1993); Chothia and Lesk, *J. Mol. Biol.* 196:901 (1987), Carter et al., *Proc. Natl. Acad. Sci. U.S.A.* 89:4285 (1992); Presta et al., *J. Immunol.* 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; International Application Nos. PCT/US98/16280; PCT/US96/18978; PCT/US91/09630; PCT/US91/05939; PCT/US94/01234; PCT/GB89/01334; PCT/GB91/01134; PCT/GB92/01755; International Patent Application Publication Nos. WO90/14443; WO90/14424; WO90/14430; and European Patent Publication No. EP 229246.

Anti-FcγRIIA humanized antibodies and antigen-binding fragments thereof can also be made in transgenic mice containing human immunoglobulin loci that are capable, upon immunization, of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments an anti-FcγRIIA antibody fragment is provided. Various techniques are known for the production of antibody fragments. Traditionally, these fragments are derived via proteolytic digestion of intact antibodies. See, e.g., Morimoto et al., *J. Biochem. Biophys. Meth.* 24:107-117 (1993); Brennan et al., *Science,* 229:81-83 (1985). In certain embodiments, anti-FcγRIIA antibody fragments are produced recombinantly. Fab, Fv, and scFv antibody fragments can all be expressed in and secreted from *E. coli* or other host cells, thus allowing the production of large amounts of these fragments. Such anti-FcγRIIA antibody fragments can also be isolated from the antibody phage libraries discussed above. Anti-FcγRIIA antibody fragments can also be linear antibodies, as described in U.S. Pat. No. 5,641,870. Other techniques for the production of antibody fragments will be apparent to the skilled practitioner.

According to the present invention, techniques can be adapted for the production of single-chain antibodies specific to FcγRIIA (see, e.g., U.S. Pat. No. 4,946,778). In addition, methods can be adapted for the construction of Fab expression libraries (see, e.g., Huse et al., *Science* 246:1275-1281 (1989)) to allow rapid and effective identification of monoclonal Fab fragments with the desired specificity for FcγRIIA. Antibody fragments can also be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

In some aspects, FcγRIIA-binding molecule can be modified in order to reduce or eliminate effector function. This can be achieved, for example, by the Triple Mutation™ L234F/L235E/P331S in the Fc domain of IgGl. Other mutations that reduce effector function are known in the art. See, e.g., Armour et al., *Eur. J. Immunol.* 29:2613-2624, 1999; Shields et al., *J. Biol. Chem.* 276:6591-6604, 2001.

In certain aspects, an FcγRIIA-binding molecule can be modified in order to increase its serum half-life. This can be achieved, for example, by incorporation of a salvage receptor binding epitope into the binding molecule by mutation of the appropriate region, or by incorporating the epitope into a peptide tag that is then fused to the binding molecule at either end or in the middle (e.g., by DNA or peptide synthesis), or by YTE mutation. Other methods to increase the serum half-life of an antibody or antigen-binding fragment thereof, e.g., conjugation to a heterologous molecule such as PEG, are known in the art.

Heteroconjugate FcγRIIA antibodies and antigen-binding fragments thereof are also within the scope of the present invention. Heteroconjugate antibodies are composed of two covalently joined antibodies. Such antibodies have, for example, been proposed to target immune cells to unwanted cells (see, e.g., U.S. Pat. No. 4,676,980). It is contemplated that heteroconjugate anti-FcγRIIA antibodies and antigen-binding fragments thereof can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

An FcγRIIA-binding molecule can be modified to contain additional chemical moieties not normally part of the protein. Such moieties can improve the characteristics of the binding molecule, for example, solubility, biological half-life, or absorption. The moieties can also reduce or eliminate any undesirable side effects of the binding molecule. An overview of those moieties can be found in *Remington's Pharmaceutical Sciences,* 20th ed., Mack Publishing Co., Easton, Pa. (2000).

In certain aspects, the disclosure provides a composition, e.g., a pharmaceutical composition, comprising an FcγRIIA-binding molecule of the invention, optionally further comprising one or more carriers, diluents, excipients, or other additives.

IV. Polynucleotides Encoding FcγRIIA-Binding Molecules, Preparation and Expression Thereof This disclosure provides polynucleotides comprising nucleic acid sequences that encode an FcγRIIA-binding molecule, e.g., a polypeptide that specifically binds FcγRIIA. For example, the invention provides a polynucleotide comprising a nucleic acid sequence that encodes an anti-FcγRIIA antibody or encodes an antigen-binding fragment of such an antibody. The polynucleotides of the invention can be in the form of RNA or in the form of DNA. DNA includes cDNA, genomic DNA, and synthetic DNA; and can be double-stranded or single-stranded, and, if single stranded, can be the coding strand or non-coding (anti-sense) strand.

In certain embodiments, the polynucleotide can be isolated. In certain embodiments, the polynucleotide can be substantially pure. In certain embodiments, the polynucleotide can be cDNA or are derived from cDNA. In certain embodiments, the polynucleotide can be recombinantly produced. In certain embodiments, the polynucleotide can comprise the coding sequence for a mature polypeptide, fused in the same reading frame to a polynucleotide which aids, for example, in expression and optionally, secretion, of a polypeptide from a host cell (e.g., a promoter or other regulatory sequence, a leader sequence that functions as a secretory sequence for controlling transport of a polypeptide from the cell). The polypeptide having a leader sequence is a preprotein and can have the leader sequence cleaved by the host cell to form the mature form of the polypeptide. The polynucleotide can also encode an FcγRIIA-binding proprotein which is the mature protein plus additional 5' amino acid residues.

The disclosure provides an isolated polynucleotide comprising a nucleic acid encoding an FcγRIIA-binding molecule comprising an amino acid sequence from a VH and/or VL domain having 85%, 90%, 95%, 96%, 97%, 98%, 99%, or 100% similarity to an amino acid sequence set forth herein, and/or comprising 0, 1, 2, 3, 4, 5 or more amino acid substitutions, e.g., conservative substitutions, relative to an amino acid sequence set forth herein, such as a sequence from any of clones 32LO0350, 32LO0351, 32LO0352, 32LO0354, 32LO0355, or 32LO0356.

In certain embodiments the polynucleotide that comprises the coding sequence for the FcγRIIA-binding molecule is fused in the same reading frame as a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

Polynucleotide variants are also provided. Polynucleotide variants can contain alterations in the coding regions, non-coding regions, or both. In some embodiments, polynucleotide variants contain alterations that produce silent substitutions, additions, or deletions, but do not alter the properties or activities of the encoded polypeptide. In some embodiments, polynucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

The invention includes vectors comprising the polynucleotides described above. Suitable vectors are described elsewhere herein, and are known to those of ordinary skill in the art. In some embodiments, a polynucleotide comprising a nucleic acid encoding a VH domain or portion thereof and the polynucleotide comprising a nucleic acid encoding a VL domain or portion thereof can reside in a single vector, or can be on separate vectors. Accordingly, the disclosure provides one or more vectors comprising the polynucleotides described above.

In certain aspects, the disclosure provides a composition, e.g., a pharmaceutical composition, comprising a polynucleotide or vector as described above, optionally further comprising one or more carriers, diluents, excipients, or other additives.

The disclosure further provides a host cell comprising a polynucleotide or vector of the invention, wherein the host cell can, in some instances, express a binding molecule that specifically binds to FcγRIIA. Such a host cell can be utilized in a method of making an FcγRIIA-binding molecule, where the method includes (a) culturing the host cell and (b) isolating the binding molecule from the host cell or from the culture medium, if the binding molecule is secreted by the host cell.

In some embodiments a nucleotide sequence encoding an FcγRIIA-binding molecule, can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a nucleotide oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding the binding molecule can be inserted into an expression vector and operatively linked to an expression control sequence appropriate for expression of the binding molecule in a desired host. Proper assembly can be confirmed, e.g., by nucleotide sequencing, restriction mapping, and/or expression of a biologically active polypeptide in a suitable host. In order to obtain high expression levels of a transfected gene in a host, the gene can be operatively linked to or associated with transcriptional and translational expression control sequences that are functional in the chosen expression host.

In certain embodiments, recombinant expression vectors are used to amplify and express DNA encoding FcγRIIA-binding molecules. Recombinant expression vectors are replicable DNA constructs that have synthetic or cDNA-derived DNA fragments encoding a polypeptide chain of an FcγRIIA-binding molecule, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR 1, pBR322, pMB9 and their derivatives, wider host range plasmids, such as M13, and filamentous single-stranded DNA phages.

Suitable host cells for expression of an FcγRIIA-binding molecule include prokaryotes, yeast, insect, or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Additional information regarding methods of protein production, including antibody production, can be found in, e.g., U.S. Patent Publication No. 2008/0187954, U.S. Pat. Nos. 6,413,746 and 6,660,501, and International Patent Publication No. WO 04009823.

Various mammalian or insect cell culture systems can be advantageously employed to express recombinant FcγRIIA-binding molecules. Expression of recombinant proteins in mammalian cells can be performed because such proteins are generally correctly folded, appropriately modified, and completely functional. Examples of suitable mammalian host cell lines include HEK-293 and HEK-293T, the COS-7 lines of monkey kidney cells, described by Gluzman (Cell 23:175, (1981)), and other cell lines including, for example, L cells, C127, 3T3, Chinese hamster ovary (CHO), HeLa, and BHK cell lines. Mammalian expression vectors can comprise non-transcribed elements, such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are reviewed by Luckow and Summers (*BioTechnology* 6:47 (1988)).

FcγRIIA-binding molecules produced by a transformed host can be purified according to any suitable method. Such standard methods include chromatography (e.g., ion exchange, affinity, and sizing column chromatography), centrifugation, differential solubility, or by any other standard technique for protein purification. Affinity tags such as hexahistidine, maltose binding domain, influenza coat sequence, and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose, or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an FcγRIIA-binding molecule. Some or all of the foregoing purification steps, in various combinations, can also be employed to provide a homogeneous recombinant protein.

A recombinant FcγRIIA-binding molecule produced in bacterial culture can be isolated, for example, by initial extraction from cell pellets, followed by one or more concentration, salting-out, aqueous ion exchange, or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005.

V. Treatment Methods Using FcγRIIA-Binding Molecules

Methods are provided for the use of FcγRIIA binding molecules to treat patients having a disease or disorder associated with inappropriate FcγRIIA activation, such as disease or disorders characterized by immune-complex deposition, immune-complex mediated NETosis, ANCA-induced FcγRIIA activation, and anti-platelet antibody-triggered FcγRIIA activation. The following discussion refers to diagnostic methods and methods of treatment of various diseases and disorders with an FcγRIIA-binding molecule that is capable of specifically binding FcγRIIA and antagonizing FcγRIIA activity.

In one embodiment, treatment or prevention includes the application or administration of an FcγRIIA binding molecule or a composition comprising FcγRIIA binding molecule to a subject or patient, or application or administration of the FcγRIIA binding molecule to an isolated tissue or cell line from a subject or patient, where the subject or patient has a disease, a symptom of a disease, or a predisposition toward a disease. The composition is preferably a pharmaceutical composition.

FcγRIIA binding molecules provided herein are useful for the treatment or prevention of certain inflammatory, immune-mediated, or autoimmune diseases or disorders. Examples of inflammatory, immune-mediated, or autoimmune disease or disorders include, but are not limited to vasculitis, e.g., Anti-neutrophil cytoplasm antibodies (ANCA), ANCA-associated vasculitis (AAV) or giant cell arteritis (GCA) vasculitis, Sjögren's syndrome, inflammatory bowel disease (IBD), pemphigus vulgaris, lupus nephritis, psoriasis, thyroiditis, Type I Diabetes, immune thrombocytopenia (ITP), ankylosing spondylitis, multiple sclerosis, systemic lupus erythematosus (SLE), rheumatoid arthritis, Crohn's disease, Myasthenia Gravis, neuromyelitis optica (NMO), systemic sclerosis, insulin-dependent diabetes mellitus (IDDM), akylosing spondylitis, atopic dermatitis, uveitis, Graft-versus-host disease (GVHD), polymyositis, dermatomyositis, membranous nephropathy, hemolytic anemia, mixed connective tissue disease, sclerodema, sepsis, thrombosis, acute kidney injury, acute lung injury, chronic obstructive pulmonary disease, glomerulonephritis, toxic liver injury, stroke, atherogenesis, IgG mediated hypersensitive reaction, anti-drug immune complex mediated adverse effects, and other autoantibody or immune-complex-mediated disorders.

Clinical response to administration of an FcγRIIA-binding molecule can be assessed using screening techniques such as magnetic resonance imaging (MRI), x-radiographic imaging, computed tomographic (CT) scan, flow cytometry or fluorescence-activated cell sorter (FACS) analysis, histology, gross pathology, and blood chemistry, including but not limited to changes detectable by ELISA, ELISPOT, RIA, chromatography, and the like. Further, the subject undergoing therapy with the FcγRIIA-binding molecule can experience improvement in the symptoms associated with the disease or disorder.

Methods of preparing and administering FcγRIIA-binding molecules to a subject in need thereof are well-known to or can be readily determined by those skilled in the art. The route of administration of the FcγRIIA binding molecule can be, for example, oral, parenteral, by inhalation, or topical. The term "parenteral" as used herein includes, e.g., intravenous, intraarterial, intraperitoneal, intramuscular, subcutaneous, rectal, and vaginal administration. Oral dosage forms include, e.g., capsules, tablets, aqueous suspensions, and solutions. Nasal aerosol or inhalation dosage forms can be prepared, for example, as solutions in saline, employing benzyl alcohol or other suitable preservatives, absorption promoters to enhance bioavailability, and/or other conventional solubilizing or dispersing agents.

Usually, a suitable pharmaceutical composition can comprise a buffer, optionally a surfactant, optionally a stabilizer agent, etc. The form and character of the pharmaceutically acceptable carrier or diluent can be dictated by the amount of active ingredient with which it is to be combined, the route of administration and other well-known variables. A cocktail comprising one or more species of FcγRIIA binding molecules, e.g., anti-FcγRIIA antibodies, or antigen-binding fragments, variants, or derivatives thereof, of the invention can also be used. In other methods, FcγRIIA-binding molecules can be delivered directly to the site of the adverse cellular population, thereby increasing the exposure of the diseased tissue to the therapeutic agent. In one embodiment, the administration is directly to the airway, e.g., by inhalation or intranasal administration.

As discussed herein, FcγRIIA binding molecules can be administered in a therapeutically effective amount for the in vivo treatment of FcγRIIA-mediated diseases such as inflammatory, immune-mediated, or autoimmune diseases or disorders. In this regard, it will be appreciated that the disclosed binding molecules can be formulated so as to facilitate administration and promote stability of the active agent. Pharmaceutical compositions in accordance with the present invention can comprise a pharmaceutically acceptable, non-toxic, sterile carrier such as physiological saline, non-toxic buffers, preservatives and the like. For the purposes of the instant application, a "therapeutically effective amount" of an FcγRIIA-binding molecule means an amount sufficient to achieve a benefit, e.g., to ameliorate symptoms of a disease or condition or to detect a substance or a cell. Suitable formulations for use in the therapeutic methods disclosed herein are described in *Remington's Pharmaceutical Sciences,* 20th ed., Mack Publishing Co., Easton, Pa. (2000).

The composition can be administered as a single dose, multiple doses, or over an established period of time in an infusion. Dosage regimens also can be adjusted to provide the optimum desired response (e.g., a therapeutic or prophylactic response). The amount of an FcγRIIA-binding molecule that can be combined with carrier materials to produce a dosage form will vary depending upon many different factors, including means of administration, target site, physiological state of the patient (i.e., the severity of the disease, the history of the disease, and the age, height, weight, health, and physical condition of the individual undergoing therapy), whether treatment is prophylactic or therapeutic, other medications administered, and whether the patient is human or an animal. Usually, the patient is a human, but non-human mammals, including transgenic mammals can also be treated. The amount of FcγRIIA-binding molecule to be administered is can be determined by one of ordinary skill in the art. Treatment dosages can be titrated using routine methods known to those of skill in the art to optimize safety and efficacy.

This disclosure also provides for the use of an FcγRIIA-binding molecule as described herein to treat or prevent an inflammatory, immune-mediated, or autoimmune disease or disorder, e.g., vasculitis, such as ANCA or GCA vasculitis, immune thrombocytopenia, systemic lupus erythematosus, lupus nephritis, Sjögren's syndrome, rheumatoid arthritis, Crohn's disease, Myasthenia Gravis, GVHD, ADA-mediated adverse effects, NETosis, and NETosis-associated disorders, including sepsis, thrombosis, acute kidney injury, acute lung injury, chronic obstructive pulmonary disease, glomerulonephritis, toxic liver injury, stroke, atherogenesis, Type I diabetes, and IgG mediated hypersensitive reaction.

This disclosure also provides for the use of an FcγRIIA-binding molecule as described herein in the manufacture of a medicament for treating or preventing an inflammatory, immune-mediated, or autoimmune disease or disorder, e.g., vasculitis, such as ANCA or GCA vasculitis, immune thrombocytopenia, systemic lupus erythematosus, lupus nephritis, Sjögren's syndrome, rheumatoid arthritis, Crohn's disease, Myasthenia Gravis, GVHD, ADA-mediated adverse effects, NETosis, and NETosis-associated disorders, including sepsis, thrombosis, acute kidney injury, acute lung injury, chronic obstructive pulmonary disease, glomerulonephritis, toxic liver injury, stroke, atherogenesis, Type I diabetes, and IgG mediated hypersensitive reaction.

VI. Assays and Diagnostics

FcγRIIA-binding molecules of the invention can be used for diagnosis of FcγRIIA-mediated diseases such as certain inflammatory, immune-mediated, or autoimmune diseases or disorders, and/or for diagnostic monitoring of protein levels as part of a clinical testing procedure, e.g., to determine the efficacy of a given treatment regimen. Such methods typically involve using the FcγRIIA-binding molecules described herein to assay the expression level FcγRIIA. By "assay the expression level of FcγRIIA" is intended to mean qualitatively or quantitatively measuring or estimating the level of FcγRIIA in a first biological sample either directly (e.g., by determining or estimating absolute protein level) or relatively (e.g., by comparing to the disease associated polypeptide level in a second biological sample). The FcγRIIA expression level in the first biological sample can be measured or estimated and compared to a standard FcγRIIA level, the standard being taken from a second biological sample obtained from an individual not having the disorder, or being determined by averaging levels from a population of individuals not having the disorder. In some aspects, an increase in the protein level of the test sample compared to the standard sample is indicative of a disease or disorder treatable by an FcγRIIA-binding molecule of the invention. As will be appreciated in the art, once the "standard" FcγRIIA level is known, it can be used repeatedly as a standard for comparison.

By "biological sample" is intended any biological sample obtained from an individual, cell line, tissue culture, or other source of cells potentially expressing FcγRIIA. Methods for obtaining tissue biopsies and body fluids from mammals are known in the art.

The FcγRIIA-binding molecules of the invention can be used to assay FcγRIIA protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)) Immunoassays that can be used include but are not limited to competitive and non-competitive assay systems using techniques such as Western blots, radioimmunoassays, ELISA (enzyme linked immunosorbent assay), ELISPOT, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and immunoelectron microscopy, to name some examples. Such assays are routine and well known in the art. Those skilled in the art will be able to determine operative and optimal assay conditions for each determination by employing routine experimentation.

Detection of FcγRIIA can be facilitated by coupling the binding molecule to a detectable substance or label. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin. An example of a luminescent material is luminol. Examples of bioluminescent materials include luciferase, luciferin, and aequorin. Examples of suitable radioactive material include $^{125}I$, $^{131}I$, $^{35}S$, or $^{3}H$.

In situ detection can be accomplished by removing a histological specimen, for example a blood sample, from a patient, and applying thereto a labeled FcγRIIA-binding molecule, applied by overlaying the labeled FcγRIIA-binding molecule onto a biological sample. Through the use of such a procedure, it is possible to determine not only the presence of FcγRIIA, but also its distribution in the examined tissue. Using the present invention, those of ordinary skill will readily perceive that any of a wide variety of histological methods (such as staining procedures) can be modified in order to achieve such in situ detection.

Methods and reagents suitable for determination of binding characteristics of an isolated FcγRIIA-binding molecule are known in the art and/or are commercially available. Equipment and software designed for such kinetic analyses are commercially available (e.g., BIAcore®, BIAevaluation® software, GE Healthcare; KINEXA® Software, Sapidyne Instruments).

VII. Kits Comprising FcγRIIA-Binding Molecules

This disclosure further provides kits that comprise an FcγRIIA-binding molecule, which can be used to perform the methods described herein. In certain embodiments, a kit comprises at least one purified FcγRIIA-binding molecule in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed FcγRIIA-binding molecules can be readily incorporated into one of the established kit formats which are well known in the art.

All of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

The invention is further described in the following non-limiting Examples.

EXAMPLES

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

Example 1. Humanization and Optimization of Anti-FcγRIIA Murine Monoclonal Antibody Cloning, Expression, Purification of FcγRIIA and FcγRIIB from Human and Cynomolgus Monkey cDNA molecules encoding the extracellular domains of CD32A, CD32B from human were synthesized with primer extension PCR cloning using database sequences as references (see Table 2). Sequences were cloned into the pEBNA mammalian expression vector (Thermo Fisher, Cat. No. A10898) fused to a 6×His Flag tag at the C-terminus (HHHHHHDYKDDDDK) (SEQ ID NO: 18). Proteins were expressed in FreeStyle 293F cells (Thermo Fisher Cat. No. R790-07). Expressed protein in supernatant was purified using Ni-NTA affinity chromatography (Histrap HP column (GE Healthcare, Cat. No. 17-5248-02)) followed by Size Exclusion chromatography (Superdex 200 column (GE Healthcare, Cat. No. 17-1069-01)).

TABLE 2

| Protein | Amino Acids | Accession No. (Uniprot) |
|---|---|---|
| Human CD32A 131H | 34-217 | P12318 |
| Human CD32A 131R | 34-217 | P12318H131R |
| Human CD32B | 42-223 | P31994 |

FcγRIIA Consensus Sequence in Cynomolgus Monkey (*Macaca fascicularis*)

There are 36 amino acids in cynomolgus FcγRIIA that are non-homologous to human FcγRIIA (UniProt P12318) resulting in 88% sequence identity (aa 1-317). Table 3 shows non-homologous amino acids.

TABLE 3

| AA human | AA Cyno | AA position | |
|---|---|---|---|
| Arg | Gly | 14 | Amino acids polymorphisms observed in the majority of animals (non-homologous to human) |
| Ala | Thr | 35 | |
| Gln | Arg | 54 | |
| Gln | Gly | 63 | |
| Arg | His | 66 | |
| Glu | Asp | 69 | |
| Ile | Thr | 73 | |

TABLE 3-continued

| AA human | AA Cyno | AA position |
|---|---|---|
| Thr | Arg | 103 |
| Gln | Arg | 108 |
| Val | Ala | 125 |
| **Pro** | **Thr** | **129** |
| Gln | Arg | 134 |
| Val | Ile | 152 |
| **Thr** | **Ala** | **155** |
| **Lys** | **Ile** | **161** |
| Gln | Lys | 163 |
| Leu | Met | 168 |
| **Asp** | **Asn** | **169** |
| Thr | Asn | 171 |
| Leu | Pro | 195 |
| Phe | Tyr | 196 |
| Met | Val | 210 |
| He | Thr | 224 |
| Ala | Gly | 225 |
| Thr | Ile | 226 |
| **Ile** | **Val** | **231** |
| Gln | Arg | 258 |
| Phe | Asn | 259 |
| Pro | Leu | 262 |
| Met | Thr | 266 |
| Ile | Leu | 269 |
| Lys | Arg | 301 |
| **Leu** | **Met** | **305** |
| Pro | Ser | 308 |
| His | Tyr | 312 |
| Val | Asp | 313 |

Variations where the minor cynomolgus allele corresponds to human are shown in bold type.

An additional 7 coding polymorphisms were identified among cynomolgus populations with a minor allele frequency (MAF) of >20%. Table 4 shows single nucleotide polymorphism variation.

TABLE 4

| ID | Chr:bp | Alleles | AA | AA coord | MAF (ALL) | MAF (Chinese) | Variant Type |
|---|---|---|---|---|---|---|---|
| tmp_1_90182815_T_C | 1:90182815 | T/C | G/S | 14 | **0.4375** | **0.312** | Missense |
| tmp_1_90181550_T_C | 1:90181550 | T/C | N/S | 78 | 0.0104167 | 0.03125 | Missense |
| tmp_1_90181541_A_C | 1:90181541 | A/C | L/R | 81 | 0.114583 | 0.03125 | Missense |
| tmp_1_90181480_C_A | 1:90181480 | C/A | E/D | 101 | 0.0520833 | | Missense |
| tmp_1_90181440_C_T | 1:90181440 | C/T | V/I | 115 | 0.0104167 | 0.03125 | Missense |
| tmp_1_90177600_G_T | 1:90177600 | G/T | *T/P* | 129 | **0.416667** | **0.31375** | Missense |
| tmp_1_90177522_C_T | 1:90177522 | C/T | *A/T* | 155 | **0.40625** | **0.40625** | Missense |
| tmp_1_90177503_A_T | 1:90177503 | A/T | *I/K* | 161 | **0.416667** | **0.375** | Missense |
| tmp_1_90177501_A_C | 1:90177501 | A/C | S/A | 162 | 0.15625 | 0.1875 | Missense |
| tmp_1_90177493_T_G | 1:90177493 | T/G | K/N | 164 | 0.16667 | **0.25** | Missense |
| tmp_1_90177485_G_T | 1:90177485 | G/T | H/P | 167 | **0.21875** | **0.3125** | Missense |
| tmp_1_90177480_T_C | 1:90177480 | T/C | *N/D* | 169 | **0.28125** | **0.25** | Missense |
| tmp_1_90177458_T_C | 1:90177458 | T/C | Q/R | 176 | **0.25** | **0.40625** | Missense |
| tmp_1_90176570_C_T | 1:90176570 | C/T | M/I | 216 | 0.041667 | | Missense |
| tmp_1_9017657_1_A_G | 1:90176571 | A/G | M/T | 216 | **0.239683** | 0.03125 | Missense |
| tmp_1_90176532_G_A | 1:90176532 | G/A | A/V | 229 | 0.0416667 | | Missense |

TABLE 4-continued

| ID | Chr:bp | Alleles | AA | AA coord | MAF (ALL) | MAF (Chinese) | Variant Type |
|---|---|---|---|---|---|---|---|
| tmp_1_90176527_C_T | 1:90176527 | C/T | *V/I* | 231 | **0.354167** | **0.40625** | Missense |
| tmp_1_90173580_G_C | 1:90173580 | G/C | R/G | 258 | 0.03125 | | Missense |
| tmp_1_90173576_T_A | 1:90173576 | T/A | N/I | 259 | **0.270833** | 0.0625 | Missense |
| tmp_1_90173577_T_A | 1:90173577 | T/A | N/Y | 259 | **0.270833** | 0.0625 | Missense |
| tmp_1_90173574_C_G | 1:90173574 | C/G | E/Q | 260 | **0.260417** | 0.03125 | Missense Splice region |
| tmp_1_90169431_C_T | 1:90169431 | C/T | M/I | 305 | 0.0520833 | | Missense |
| tmp_1_90169433_T_G | 1:90169433 | T/G | IWL | 305 | 0.34375 | 0.09375 | Missense |
| tmp_1_90169423_G_A | 1:90169423 | G/A | S/F | 308 | 0.0104167 | | Missense |

MAF>20% shown in bold type; minor alleles corresponding to the major human allele shown in italics.

Consensus cynomolgus sequences and alignments to human FcγIIA are shown in FIGS. 1A-1C.

Cynomolgus CD32A Proteins

Three versions of cynomologus CD32A were made based on polymorphisms around the epitope of IV3 (Ramsland et. al., *J. Immunol.* 187:3208-3217 (2011)). These proteins were expressed in HEK cells by GeneArt and purified by Ni-NTA affinity chromatography utilizing a c-terminal 6×his tag.

```
>Human_CD32A_131H
                                        SEQ ID NO: 11
QAAAPPKAVLKLEPPWINVLQEDSVTLTCQGARSPESDSIQWFHNGN

LIPTHTQPSYRFKANNNDSGEYTCQTGQTSLSDPVHLTVLSEWLVLQ

TPHLEFQEGETIMLRCHSWKDKPLVKVTFFQNGKSQKFSHLDPTFSI

PQANHSHSGDYHCTGNIGYTLFSSKPVTITVQVPSMGSSSPMGAHHH

HHHDYKDDDDK

>Human_CD32A_131R
                                        SEQ ID NO: 12
QAAAPPKAVLKLEPPWINVLQEDSVTLTCQGARSPESDSIQWFHNGN

LIPTHTQPSYRFKANNNDSGEYTCQTGQTSLSDPVHLTVLSEWLVLQ

TPHLEFQEGETIMLRCHSWKDKPLVKVTFFQNGKSQKFSRLDPTFSI

PQANHSHSGDYHCTGNIGYTLFSSKPVTITVQVPSMGSSSPMGAHHH

HHHDYKDDDDK

>Human_CD32B
                                        SEQ ID NO: 13
TPAAPPKAVLKLEPQWINVLQEDSVTLTCRGTHSPESDSIQWFHNGN

LIPTHTQPSYRFKANNNDSGEYTCQTGQTSLSDPVHLTVLSEWLVLQ

TPHLEFQEGETIVLRCHSWKDKPLVKVTFFQNGKSKKFSRSDPNFSI

PQANHSHSGDYHCTGNIGYTLYSSKPVTITVQAPSSSPMGGAHHHHH

HDYKDDDDK

>cynomolgus_CD32A_v1
                                        SEQ ID NO: 14
QTAPPKAVLKLEPPWINVLREDSVTLTCGGAHSPDSDSTQWFHNGNR

IPTHTQPSYRFKANNNDSGEYRCQTGRTSLSDPVHLTVLSEWLALQT

PHLEFREGETIMLRCHSWKDKPLIKVTFFQNGIAKKFSHMNPNFSIP
```

-continued

```
QANHSHSGDYHCTGNIGYTPYSSKPVTITVQVPSVGSSSPMGHHHHH

H

>cynomolgus_CD32A_v2
                                        SEQ ID NO: 15
QTAPPKAVLKLEPPWINVLREDSVTLTCGGAHSPDSDSTQWFHNGNR

IPTHTQPSYRFKANNNDSGEYRCQTGRTSLSDPVHLTVLSEWLALQT

PHLEFREGETIMLRCHSWKDKPLIKVTFFQNGIAKKFSPMNPNFSTP

QANHSHSGDYHCTGNIGYTPYSSKPVTITVQVPSVGSSSPMGHHHHH

H

>cynomolgus_CD32A_v3
                                        SEQ ID NO: 16
QTAPPKAVLKLEPPWINVLREDSVTLTCGGAHSPDSDSTQWFHNGNR

IPTHTQPSYRFKANNNDSGEYRCQTGRTSLSDPVHLTVLSEWLALQT

PHLEFREGETIMLRCHSWKDKPLIKVTFFQNGIAKKFSHMDPNFSIP

QANHSHSGDYHCTGNIGYTPYSSKPVTITVQVPSVGSSSPMGHHHHH

H

>cynomolgus_CD32B
                                        SEQ ID NO: 17
TPAAPPKAVLKLEPPWINVLREDSVTLTCGGAHSPDSDSTQWFHNGN

LIPTHTQPSYRFKANNNDSGEYRCQTGRTSLSDPVHLTVLSEWLALQ

TPHLEFREGETIMLRCHSWKDKPLIKVTFFQNGISKKFSHMNPNFSI

PQANHSHSGDYHCTGNIGYTPYSSKPVTITVQVPSMGSSSPHHHHHH
```

Protein Modifications

IgGs and modified proteins used herein were biotinylated via free amines using EZ link Sulfo-NHS-LC-Biotin (Thermo/Pierce, Cat. No. 21335). The biotin reagent was dissolved in anhydrous dimethylformamide and PBS based protein solutions were adjusted to pH ~8 with 1 M $NaHCO_3$ in D-PBS (Dulbecco's phosphate buffered saline). CD32 proteins used herein were biotinylated via free cysteines using EZ link Biotin-BMCC (Perbio/Pierce, Product No. 21900). The biotin reagent was dissolved in anhydrous dimethylformamide and mixed 3:1 with D-PBS protein solutions. Label incorporations were assessed by MALDI-TOF mass spectrometry in all cases and unreacted reagents were cleared by buffer exchange using D-PBS equilibrated disposable Sephadex G25 columns. For biotinylation, the final protein concentrations were determined by 280 nm absorbance using extinction coefficients calculated from amino acid sequences.

Cloning and Expression of IgG Molecules

Variable domains were converted to whole immunoglobulin G1 ($IgG_1$) antibody format essentially as described by Persic et al. (*Gene* 187(1):9-18 (1997)) with the following modifications. An OriP fragment was included in the expression vectors to facilitate use with CHO-transient cells and to allow episomal replication. The variable heavy (VH) domain was cloned into a vector containing the human heavy chain constant domains and regulatory elements to express whole $IgG_1$ heavy chain in mammalian cells. The heavy chain constant domains contained three mutations shown to significantly reduce Fc effector function (Oganesyan et al., *Acta Crystallographica Section D: Biological Crystallography* 64(6): 700 (2008)), to avoid engagement of CD32A via the Fc portion of full-length antibody. Similarly, the variable light (VL) domain was cloned into a vector for the expression of the human light chain (kappa) constant domains and regulatory elements to express whole IgG light chain in mammalian cells. To obtain IgGs, the heavy and light chain IgG-expressing vectors were transfected into CHO-transient mammalian cells (Daramola et al., *Biotechnol Prog.* 30(1):132-41 (2014)). IgGs were expressed and secreted into the medium. Harvests were filtered prior to purification, then IgG was purified using Protein A chromatography. Culture supernatants were loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralized by the addition of Tris-HCl (pH 9.0). The eluted material was buffer exchanged into PBS using Nap10 columns (Amersham Cat. No. 17-0854-02) and the concentration of IgG was determined spectrophotometrically using an extinction coefficient based on the amino acid sequence of the IgG (Mach et al., *Anal. Biochem.* 200(1): 74-80 (1992)). The purified IgGs were analyzed for aggregation and degradation purity using SEC-HPLC and by SDS-PAGE.

Humanization of IV.3 Ab

Mouse monoclonal antibody IV.3 was first described in 1986 (Looney R J. et al., *J. Immunol.* 136(5):1641). The hybridoma cell line was obtained from ATCC and the heavy chain variable (VH) and light chain variable (VL) segments of IV.3 were sequenced (SEQ ID NO: 5 and SEQ ID NO: 8).

Humanization of the variable domains of mouse mAb IV.3 was performed by grafting the heavy and light chain complementarity determining regions (CDRs) of IV.3 onto selected human germline frameworks (FWs). The amino acid sequences of the VH and VL domains of IV.3 were aligned to the known human germline sequences in the IMGT database (Lefranc, M. P. et al., *Nucl. Acids Res.* 37 (Database issue): D1006-D1012 (2009)), and appropriate human germlines were identified by sequence similarity, including matching of critical residues (Vernier zone, canonical class residues, and VH/VL interface residues), immunogenicity (germline frequency), stability, and expression. For the VH domain of the IV.3 antibody, the chosen human germline was IGHV1-3*01/IGHJ4. For the VL domain, it was IGKV2-28*01/IGKJ2.

Figure 3:
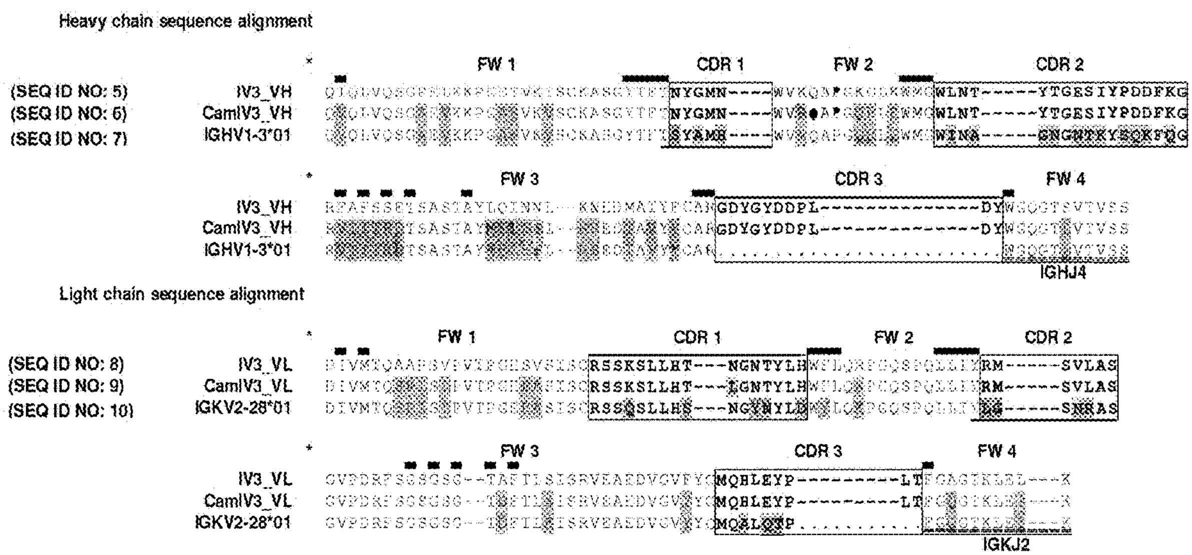
FIG. 3 shows alignment of mouse IV.3 VH (SEQ ID NO: 5) and VL (SEQ ID NO: 8) with humanized IV.3 (CamIV3 VH (SEQ ID NO: 6) and VL (SEQ ID NO: 9)) and selected human germline sequences (SEQ ID NO: 7, SEQ ID NO: 10).

A series of chimeric variable heavy and light chains were designed with one or more mouse FW regions replaced with the equivalent selected human FW. All CDR and FW regions were as defined by Kabat. Fully mouse and chimeric IV.3 variable regions were codon optimized for CHO expression and synthesized by GeneArt® Gene Synthesis (Life Technologies). These were subsequently expressed as whole immunoglobulin G1 ($IgG_1$) antibodies as described above to generate a panel of partially and wholly humanized IV.3 variants. Antibodies were characterized in an epitope competition assay as described in Example 11. Briefly, homogenous time-resolved fluorescence (HTRF®, Cisbio International) was used to detect binding of IV.3 IgG (Stemcell Technologies, Cat. No. 01470) to biotinylated human CD32A 131H. Fluorescence resonance energy transfer (FRET) between IV.3 and CD32A was detected using DyLight 649 conjugated anti-mouse antibody and streptavidin Terbium cryptate (Cisbio International, Product No. 610SATLB), respectively. The signal is disrupted by the addition of sample IgGs that compete with IV.3 for CD32A binding. Full humanization of both VH and VL chains of IV.3 was associated with a 10-fold loss of potency in this assay. A mouse residue was introduced back into the human light chain germline framework, using standard molecular biology techniques, which restored potency to within 5-fold of the mouse IgG (mutation Y36F). Data obtained is exemplified in FIG. 2. Subsequently, a potential deamination site was removed in VL CDR1 (N28L) to reduce the risk of chemical modification during manufacture. An alignment of the parental VH and VL chains (IV.3), the final humanized VH and VL chains (CamIV3) and the selected human germline sequences is shown in FIG. 3.

Optimization of CamIV3 Ab

Single amino acid substitutions were made at select positions of VH CDR2 and VL CDR1 of CamIV.3 using standard molecular biology techniques. Variants were expressed directly as IgG and supernatants quantified and screened in an IV.3 epitope competition assay as described in Example 11. Beneficial individual mutations in VH CDR2 and VL CDR1 were combined and IgGs expressed and screened. Six optimized CamIV.3 variants were chosen for further analysis, 32LO0350, 32LO0351, 32LO0352, 32LO0354, 32LO0355 and 32LO0356. NIP228 IgG1TM was used as a negative control. The activity of these variants in the IV.3 epitope competition assay is shown in FIG. 4. The optimized variants differed from CamIV3 only in HCDR2 and LCDR2 sequence, as shown in Table 5.

TABLE 5

| IgG | HCDR2 | LCDR1 |
|---|---|---|
| 32LO0352 (MEDI9600) | WLNTYTGESWYPDDFKG (SEQ ID NO: 19) | RSSKSLLHTNQNTYLH (SEQ ID NO: 22) |
| 32LO0350 | WLNTYTGESWYPDDFKG (SEQ ID NO: 19) | RSSKSLLHTNRNTYLH (SEQ ID NO: 23) |
| 32LO0355 | WLNTYTGESWYPDDFKG (SEQ ID NO: 19) | RSSKSLLHTNKNTYLH (SEQ ID NO: 24) |
| 32LO0351 | WLNTYTGESYYPDDFKG (SEQ ID NO: 20) | RSSKSLLHTYGNTYLH (SEQ ID NO: 25) |
| 32LO0354 | WLNTYTGESYYPDDFKG (SEQ ID NO: 20) | RSSKSLLHTNRNTYLH (SEQ ID NO: 23) |
| 32LO0356 | WLNTYTGESYYPDDFKG (SEQ ID NO: 20) | RSSKSLLHTNFNTYLH (SEQ ID NO: 26) |
| CamIV3 | WLNTYTGESIYPDDFKG (SEQ ID NO: 21) | RSSKSLLHTLGNTYLH (SEQ ID NO: 27) |
| IV.3 | WLNTYTGESIYPDDFKG (SEQ ID NO: 21) | RSSKSLLHTNGNTYLH (SEQ ID NO: 28) |

Amino acid differences from IV.3 are in bold type.

The CDR sequences common to IV.3, CamIV3, 32LO0350, 32LO0351, 32LO0352 (MEDI9600), 32LO0354, 32LO0355, and 32LO0356 are shown in Table 6. (See also FIG. 3.)

TABLE 6

| CDR | Sequence | Identifier |
|---|---|---|
| HCDR1 | NYGMN | SEQ ID NO: 29 |
| HCDR3 | DYGYDDPLDY | SEQ ID NO: 30 |
| HCDR3 | GDYGYDDPLDY | SEQ ID NO: 45 |
| LCDR2 | RMSVLAS | SEQ ID NO: 31 |
| LCDR3 | MQHLEYPLT | SEQ ID NO: 32 |

The amino acid sequences of the VH and VL domains of the clones 32LO0350, 32LO0351, 32LO0352, 32LO0354, 32LO0355, and 32LO0356 are shown in Table 7.

TABLE 7

| Clone | Domain | Sequence | Identifier |
|---|---|---|---|
| 32LO0352 (MEDI9600) | VH | QVQLVQSGAE VKKPGASVKV SCKASGYTFT NYGMNWVRQA PGQRLEWMGW LNTYTGESWY PDDPKGRVTI TRDTSASTAY MELSSLRSED TAVYYCARGD YGYDDPLDYW GQGTLVTVSS | SEQ ID NO: 33 |
| | VL | DIVMTQSPLS LPVTPGEPAS ISCRSSKSLL HTNGNTYLHW PLQKPGQSPQ LLIYRMSVLA SGVPDRFSGS GSGTDFTLKI SRVEAEDVGV YYCMQHLEYP LTFGQGTKLE IK | SEQ ID NO: 34 |
| 32LO0350 | VH | QVQLVQSGAE VKKPGASVKV SCKASGYTFT NYGMNWVRQA PGQRLEWMGW LNTYTGESWY PDDFKGRVTI TRDTSASTAY MELSSLRSED TAVYYCARGD YGYDDPLDYW GQGTLVTVSS | SEQ ID NO: 35 |
| | VL | DIVMTQSPLS LPVTPGEPAS ISCRSSKSLL STNRNTYLHW FLQKPGQSPQ LLIYRMSVLA SGVPDRFSGS GSGTDFTLKI SRVEAEDVGV YYCMQHLPYP LTFGQGIKLE IK | SEQ ID NO: 36 |
| 32LO0355 | VH | QVQLVQSGAE VKKPGASVKV SCKASGYTFT NYGMNWVRQA PGQRLEWMGW LNTYTGESWY PDDFKGRVTI TRDTSASTAY MELSSLRSED TAVYYCARGD YGYDDPLQYW GQGTLVTVSS | SEQ ID NO: 37 |
| | VL | DIVMTQSPLS LPVTPGEPAS ISCRSSKSLL HTNKNTYLHW FLQKPGQSPQ LLIYRMSVLA SGVPDRFSGS GSGTDFTLKI SRVEAEDVGV YYCMQHLEYF LTFGQGTKLE IK | SEQ ID NO: 38 |
| 32LO0351 | VH | QVQLVQSGAE VKKPGASVKV SCKASGYTFT NYGMNWVRQA PGQRLEWMGW LNTYTGESYY PDDFKGRVIT TRDTSASTAY MELSSLRSED TAVYYCARGD YGYDDPLDYW GQGTLVTVSS | SEQ ID NO: 39 |
| | VL | DIVMTQSPLS LPVTPGEPAS ISCRSSKSLL HTYGNTYLHW PLQKPGQSPQ LLIYRMSVLA SGVPDRFSGS GSGTDFTLKI SRVEAEDVGV YYCMQHLEYP LTFGQQTKLE IF | SEQ ID NO: 40 |
| 32LO0354 | VH | QVQLVQSGAE VKKPGASVKV SCKASGYTFT NYGMNWVRQA PGQRLEWMGW LNTYTGESYY PDDFKGRVTI TRDTSASTAY MELSSLRSED TAVYYCARGD YGYDDPLDYW GQGTLVTVSS | SEQ ID NO: 41 |
| | VL | DIVMTQSPLS LPVTPGEPAS ISCRSSKSLL HTNRNTYLHW FLQKPGQSPQ LLIYRMSVLA SGVPDRFSGS GSGTDFTLKI SRVEAEDVGV YYCMQHLEYP LTFGQGTKLE IK | SEQ ID NO: 42 |
| 32LO0356 | VH | QVQLVQSGAE VKKPGASVKV SCKASGYTFT NYGMNWVRQA PGQRLEWMGW LNTYTGESYY PDDFKGRVTI TRDTSASTAY MELSSLRSED TAVYYCARGQ YGYDDPLDYW GQGTLVTVSS | SEQ ID NO: 43 |
| | VL | DIVMTQSPLS LPVTPGEPAS ISCRSSKELL HTNFNTYLHW FLQKPGQSPQ LLIYRMSVLA SGVPDRFSGS GSGTDFTLKI SRVEAEDVGV YYCMQRLEYP LTFGQGTKLE IK | SEQ ID NO: 44 |

Affinity of IV.3 and 32LO0352 for Human and Cynomolgus CD32A

The affinity for IV.3 and 32LO0352 was measured by Biacore™ analysis. In brief, human IgG1-TM (chimeric IV.3 or 32LO0352) was captured on a Cl-Protein G chip. Serial dilutions (25 nM to 0.3906 nM in log 2 steps) of human CD32A 131 Arg, human CD32A_131H or cyno CD32A (version 3) were used as the analyte. The data were fitted to a 1:1 *Langmuir* dissociation model and shown in Table 8 (average data from two independent experiments).

TABLE 8

| IgG | Antigen | ka ($M^{-1}$ $s^{-1}$) | $k_d$ ($s^{-1}$) | $K_D$ (nM) |
|---|---|---|---|---|
| IV.3 | Hu CD32A_131Arg | 5.95 E+6 | 1.29 E−3 | 0.22 |
| 32LO0352 | | 4.98 E+6 | 7.35 E−4 | 0.15 |
| IV.3 | Hu CD32A_131His | 3.03 E+6 | 6.81 E−4 | 0.22 |
| 32LO0352 | | 2.60 E+6 | 3.37 E−4 | 0.13 |
| IV.3 | Cyno CD32A | 4.63 E+6 | 0.204 | 44.1 |
| CD32LO0352 | | 2.88 E+6 | 9.04 E−2 | 31.3 |

Example 2. Optimized IV.3 Abs Specific for Human FcγRIIA (CD32A) Binding

Figure 5A:
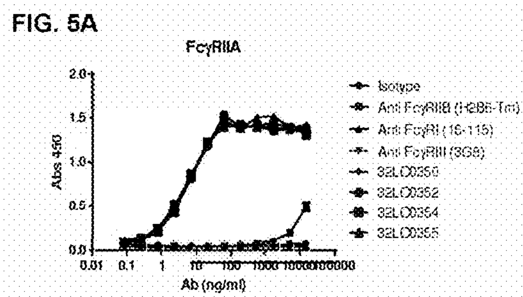
FIGS. 5A-5E show that optimized IV.3 Abs are specific for human FcγRIIA binding, but not for other FcγRs.
Figure 5B:
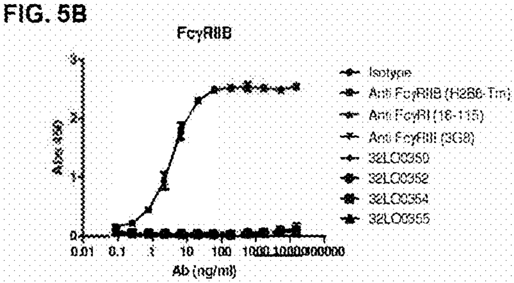
Figure 5C:
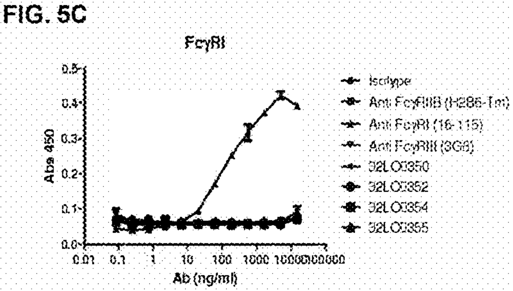
Figure 5D:
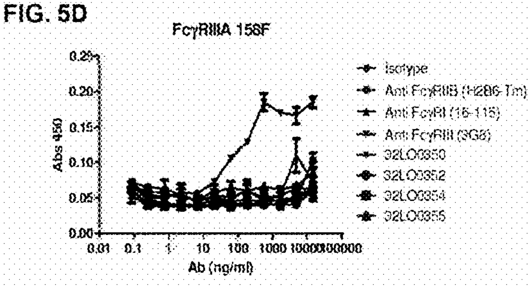
Figure 5E:
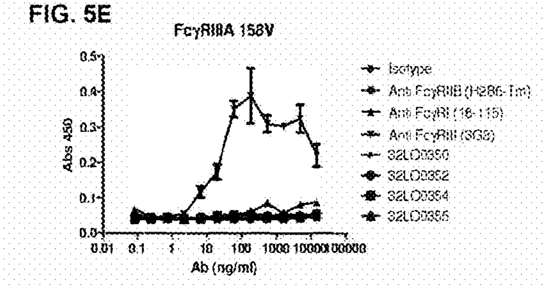

To examine the specificity of the humanized, optimized IV.3 Abs, the binding of antibodies to recombinant FcγRI, FcγRIIA-131H/H allotype, FcγRIIB, FcγRIII-158F allotype, or FcγRIII-158V allotype was assessed by ELISA. R347 Tm Ab was used as human IgG1 isotype control, and the antibodies H2B6-Tm, 3G8, 16-115 were used as positive controls for FcγRIIB, FcγRIII, FcγRIIA, and FcγRI, respectively. These four humanized, optimized IV.3 clones, 32LO0350, 32LO0352, 32LO0354, and 32LO0355, exhibited high binding specificity for human FcγRIIA (FIG. 5A) but not for other FcγRs (FIG. 5B-5E). These data demonstrate that the humanized, optimized antibody variants retain their specificity for FcγRIIA. Importantly, despite the similarity in the extracellular domains of FcγRIIA and FcγRIIB, these antibodies bind FcγRIIA but not FcγRIIB in this assay.

Figure 6:
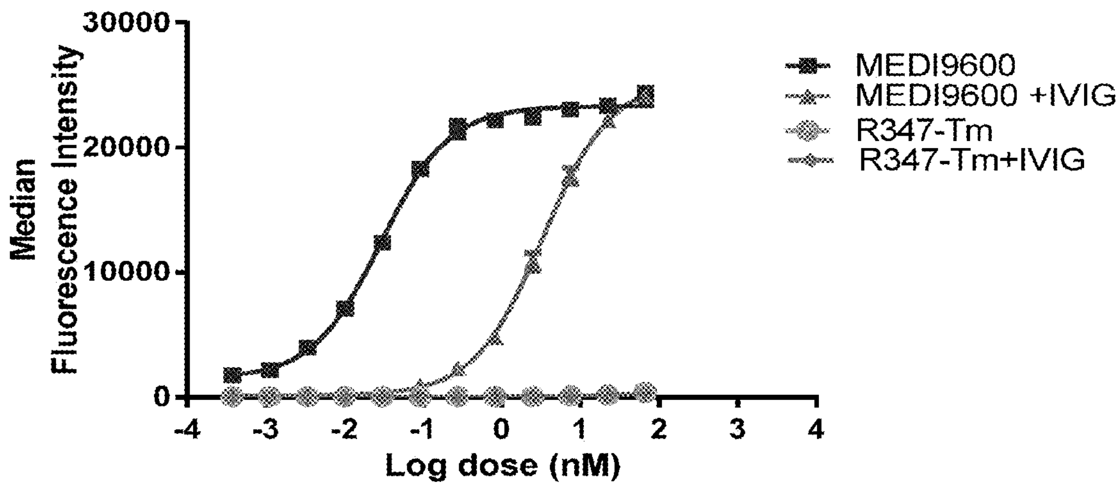
FIG. 6 shows that MEDI9600 competes with intravenous immunoglobulin (IVIG) for binding to FcγRIIA.

Example 3. MEDI9600 (32LO0352) Binding Competition with Intravenous Immunoglobulin To determine whether MEDI9600 has a competitive or non-competitive mode of action, a binding competition assay was conducted with IgG. The binding of MEDI9600 to human neutrophils expressing FcγRIIA in the presence and absence of intravenous immunoglobulin (IVIG), which mimics the physiological concentration of circulating immunoglobulin in whole blood, was assessed by flow cytometry. As shown in FIG. 6, MEDI9600 bound to human FcγRIIA-expressing neutrophils in a dose-dependent manner. The $EC_{50}$ value of MEDI9600 binding to human FcγRIIA at the neutrophil surface was 0.03 nM (FIG. 6). In the presence of 10 mg/mL IVIG, the $EC_{50}$ value of MEDI9600 binding to human FcγRIIA at the neutrophil surface was increased to 3.34 nM (FIG. 6), suggesting that MEDI9600 competes with immunoglobulin for binding to FcγRIIA. No binding was observed with the human IgG1 isotype R347-TM control (FIG. 6). These data indicate that MEDI9600 is a ligand-blocking antibody.

Example 4. Optimized IV.3 Abs Internalize Human and Cynomolgus Monkey FcγRIIA in Whole Blood Assay The murine IV.3 Ab has been shown to internalize FcγRIIA and subsequently degrade the receptor in the lysosome[13]. Consequently, removal of FcγRIIA from the surface of the cell upon antibody binding can be used as a measure of receptor internalization. We verified this mode of action and assessed the potency of the anti-FcγRIIA antibody variants in a whole blood internalization assay. This assay format was used to mimic the cellular composition and the levels of competing immunoglobulin found under physiological conditions. It has previously been shown that two common human polymorphic variants of FcγRIIA, 131H and 131R, differentially bind IgG subclasses[14]. Consequently, the capacity of the antibodies to internalize FcγRIIA from donors homozygous for 131H and 131R was also assessed. To facilitate pharmacology and toxicology assessment, the capacity of the antibodies to internalize FcγRII from monocytes was also assessed in whole blood from cynomolgus monkey.

Figure 7A:
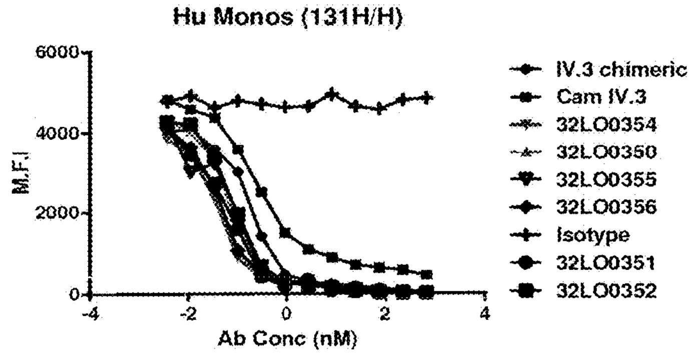
FIGS. 7A-7C show that optimized IV.3 Abs internalize FcγRIIA from the surface of monocytes from human 131H/H donors (FIG. 7A), human 131R/R donors (FIG. 7B), and cynomolgous monkeys (FIG. 7C).
Figure 7B:
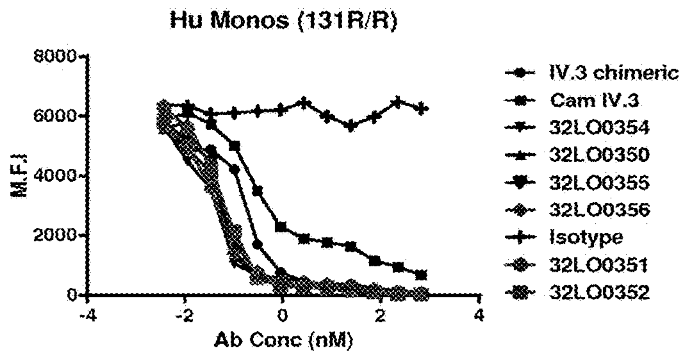
Figure 7C:
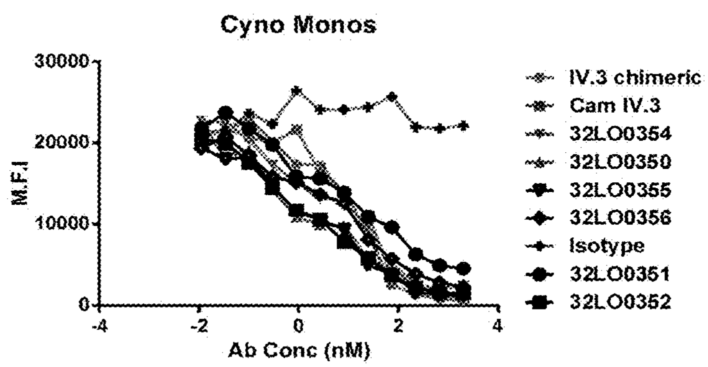

The chimeric and optimized antibodies internalized FcγRIIA from the surface of monocytes from human 131H/H donors (FIG. 7A) and human 131R/R donors (FIG. 7B). The optimized IV.3 Abs exhibited improved potency from two- to five-fold compared to the parent IV.3 chimeric Ab for both the 131H/H and 131R/R donors. The $EC_{50}$ for the optimized antibodies ranged from 0.04 nM to 0.09 nM compared to 0.19 nM for the chimeric IV.3 antibody for the 131H/H donor, and 0.04 nM to 0.06 nM compared to 0.20 nM for the chimeric IV.3 antibody for the 131 R/R donors (FIG. 7A, 7B). The optimized antibodies also internalized FcγRIIA on the surface of monocytes from cynomolgous monkeys (FIG. 7C). The potency of the optimized antibodies was up to seven-fold greater than the chimeric IV.3 Ab. Taken together, these data demonstrate that the changes introduced into the Fab regions of the heavy and light chains in the optimized variants of the IV.3 antibody are beneficial. The FcγRIIA binding specificity has been retained, murine residues have been removed, and key changes have enhanced the potency of the antibody above and beyond the parental version of the antibody in a physiologically relevant assay.

Figure 7D:
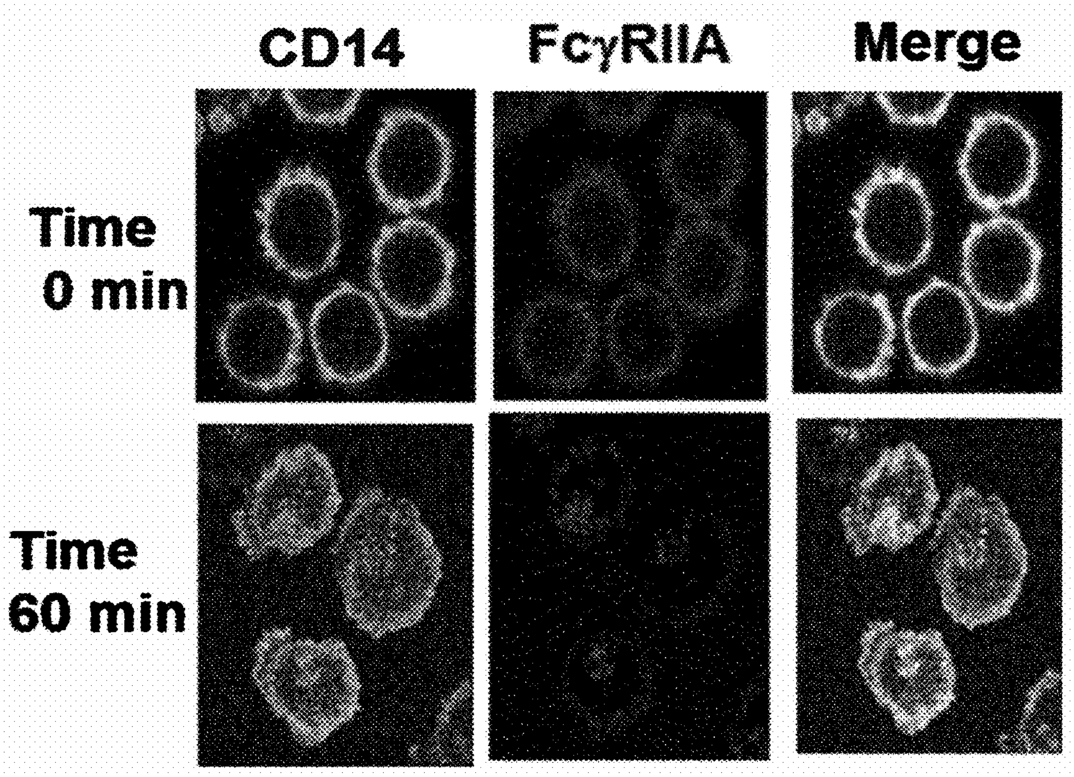
FIG. 7D shows internalization of FcγRIIA by MEDI9600 using confocal microscopy.

In an additional experiment, MEDI9600-mediated receptor internalization was confirmed by confocal microscopy. At time 0, both CD14 (as a negative control) and FcγRIIA showed cell surface staining. However, after a 1 hour incubation at 37° C., almost complete FcγRIIA internalization was stimulated by binding of MEDI9600, while CD14 remained on the cell surface (FIG. 7D).

Figure 8A:
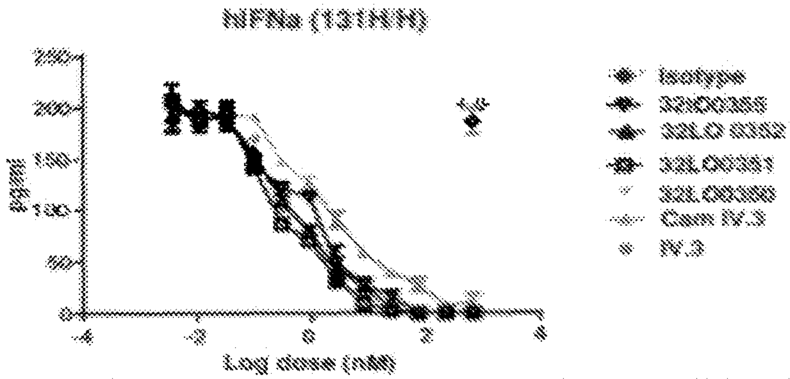
FIGS. 8A-8C show that optimized IV.3 Abs block RNP-IC-induced IFN-α expression from human and cyno PBMC, using cells from human 131 H/H donors (FIG. 8A), human 131R/R donors (FIG. 8B), and cynomologus monkeys (FIG. 8C).
Figure 8B:
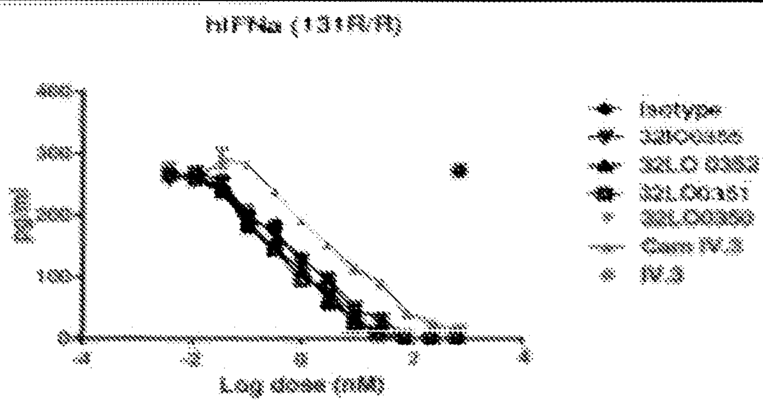
Figure 8C:
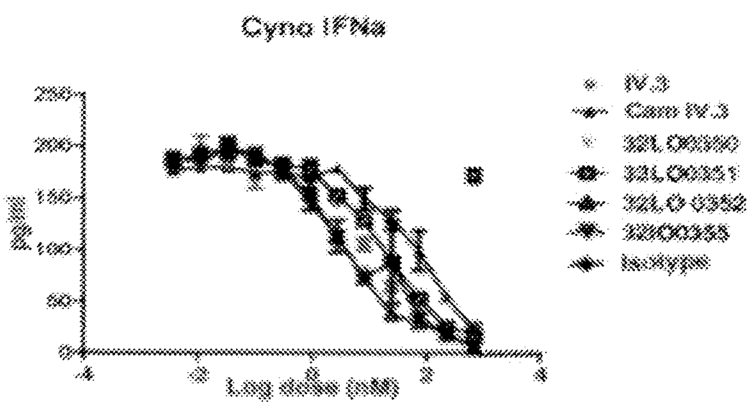

Example 5. Optimized IV.3 Abs Block RNP-IC-Induced IFNα Expression from Human and Cynomolgus Monkey PBMC We assessed the capacity of the anti-FcγRIIA antibodies to inhibit Ribonucleoprotein-Immune complex (RNP-IC)-mediated type I interferon alpha (IFNα) production. The activity of the antibodies was examined with cells from healthy donors with either a 131H/H or 131R/R haplotype, and with cells from cynomolgus monkeys. The optimized IV.3 Abs exhibited up to a 2 fold increase in potency in the RNP-IC-induced type I IFNα assay compared to the parental IV.3 antibody using cells from 131 H/H and 131R/R donors (FIG. 8A, 8B). The potency of the optimized antibodies were ~3-8 fold greater than the humanized CamIV.3 antibody with the 131 H/H donor (FIG. 8A), and ~5-12 fold greater than CamIV.3 for the 131 R/R donor (FIG. 8B). Three of the four optimized antibodies also exhibited greater potency than the parental and humanized versions of IV.3 in the RNP-IC-induced IFNα assay using cynomolgus monkey cells (FIG. 8C).

The increased potency of these optimized human anti-FcγRIIA antibodies to block immune-complex mediated induction of type I IFN is consistent with improvements in the antibody-mediated FcγRIIA uptake in the whole blood internalization assay. Since IFNα appears to play an important role in the pathogenesis of SLE, these data support the use of these humanized, optimized anti-FcγRIIA antibodies for the treatment of SLE.

Example 6. Optimized IV.3 Ab, Clone 32LO0352 (MEDI9600), Specifically Blocks Anti-Neutrophil Cytoplasmic Antibody (ANCA) Induced Neutrophil Activation A marker of neutrophil activation is the release of reactive oxygen species, which can measured in a ferri-cytochrome C reduction assay, or by flow cytometry based DH123 assay[15]. The ability of optimized IV.3 Ab clone 32LO0352 (MEDI9600) to inhibit ANCA induced neutrophil activation was first examined in ferri-cytochrome C reduction assay.

Figure 9A:
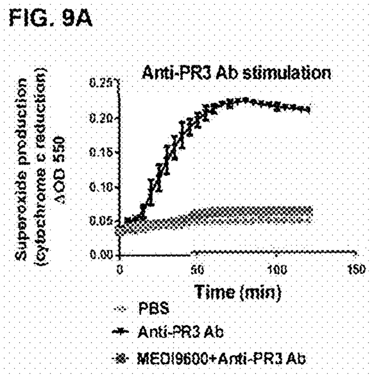
FIGS. 9A-9G show that MEDI9600 (clone 32LO0352) specifically blocks anti-neutrophil cytoplasmic antibody (ANCA) induced neutrophil activation.
Figure 9B:
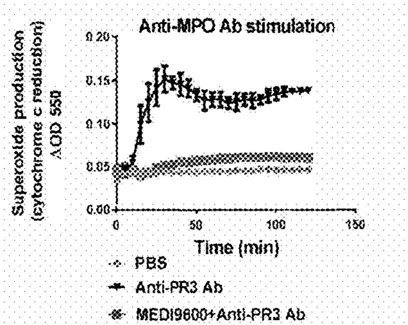
Figure 9C:
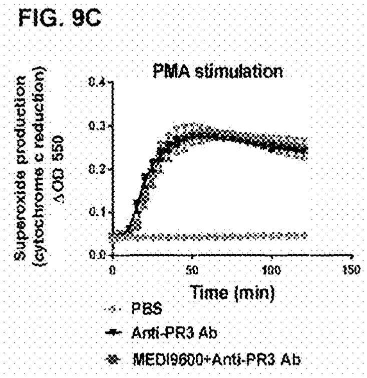

MEDI9600 specially blocked ANCA-(both Anti-PR3 Ab and anti-MPO Ab) induced neutrophil production of reactive oxygen species (FIG. 9A, 9B). To determine if MEDI9600 could non-specifically impact neutrophil activation, neutrophils were treated with PMA in the presence and absence of the FcγRIIA antibody. PMA induced reactive oxygen species, but inhibition of FcγRIIA with MEDI9600 had no effect on PMA-induced neutrophil activation (FIG. 9C). These data demonstrate that MEDI9600 specifically blocks antibody-mediated induction of neutrophil activation, whereas other mechanisms of neutrophil activation may not be impeded by this treatment.

Figure 9D:
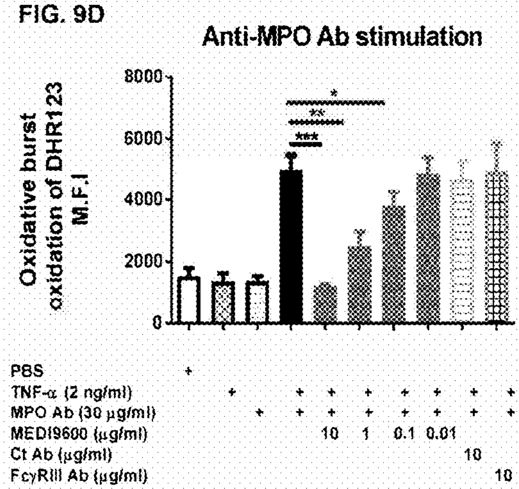
Figure 9E:
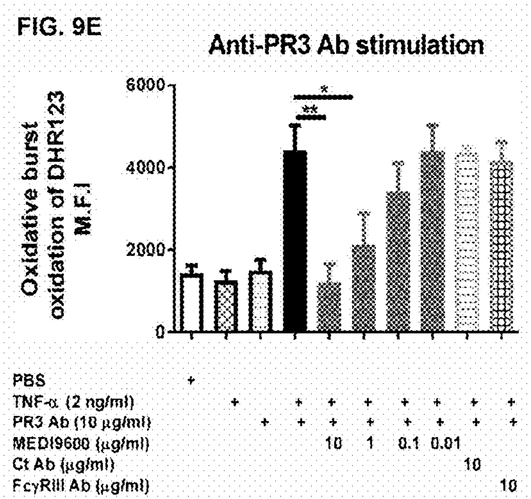
Figure 9F:
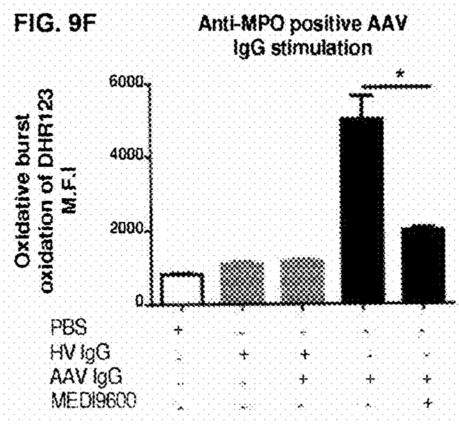
Figure 9G:
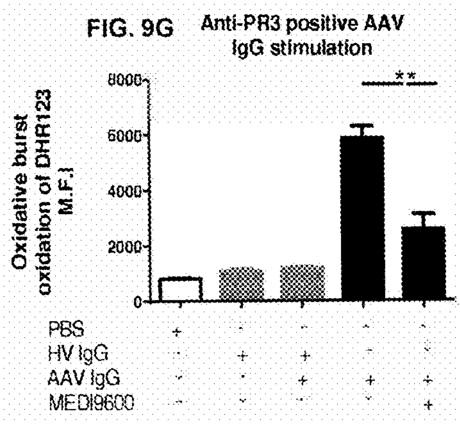

The ability of MEDI9600 to block ANCA-induced neutrophil activation was also assessed by a more sensitive flow cytometry based DHR123 assay. Using this assay format, MEDI9600 again inhibited anti-MPO and anti-PR3 Ab-induced neutrophil activation in a dose dependent manner, whereas the isotype control antibody had no effect (FIG. 9D, 9E). Both of the previous experiments used commercially available anti-MPO and anti-PR3 Abs as stimuli. To verify the ability of optimized IV.3 Ab to inhibit ANCA-induced neutrophil activation, IgG was purified from AAV patients' sera with autoantibodies against either PR3 or MPO, and used as stimuli for neutrophils. Using the flow cytometry-based DHR123 assay, MEDI9600 significantly blocked neutrophil activation triggered by AAV patient IgG (FIG. 9F, 9G).

Taken together, these data indicate that MEDI9600 anti-FcγRIIA Ab is able to specifically block anti-neutrophil cytoplasmic antibody (ANCA) induced neutrophil activation, and supports the use of the humanized, optimized MEDI9600 anti-FcγRIIA antibody for the treatment of ANCA-associated vasculitis.

Figure 10A:
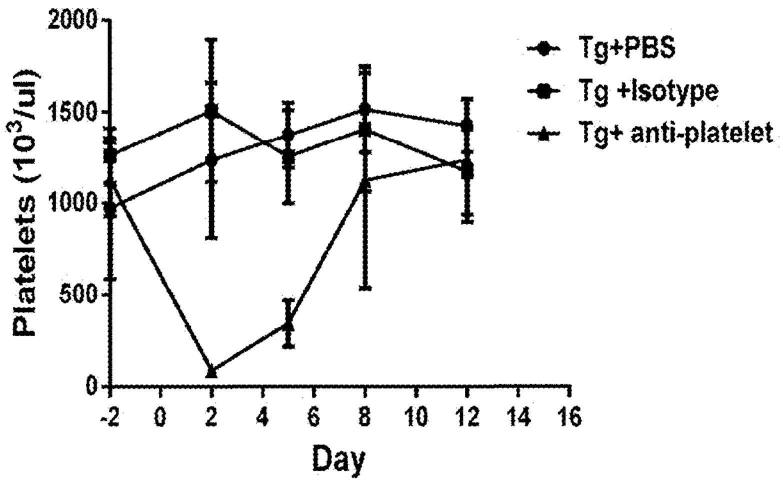
FIGS. 10A-10C show that MEDI9600 protects mice from anti-platelets antibody-induced thrombocytopenia.
Figure 10B:
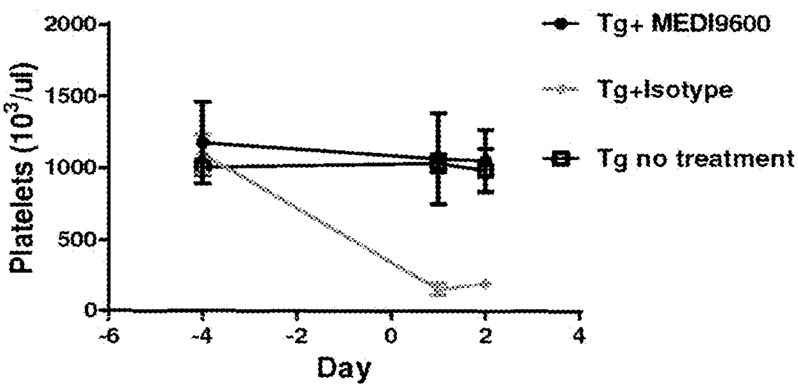
Figure 10C:
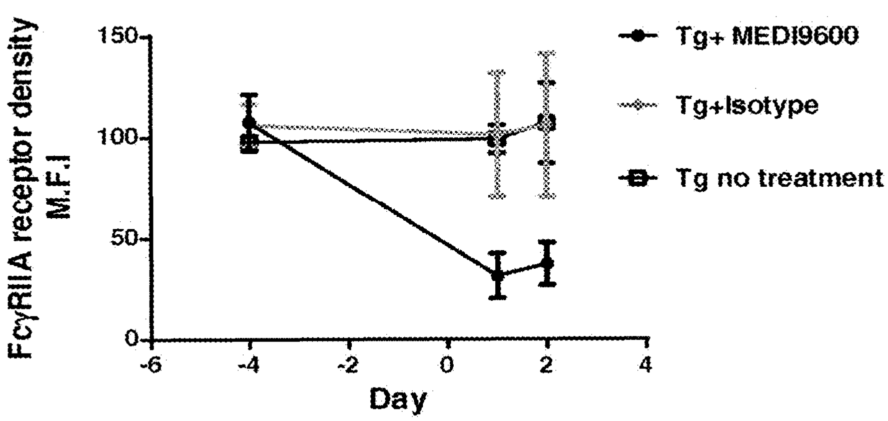

Example 7. Optimized IV.3 Ab (MEDI9600) Protects Mice from Anti-Platelet Antibody-Induced Thrombocytopenia Using the transgenic human FcγRIIA murine-activating FcγR-deficient mice, the efficacy of the optimized IV.3 Ab (MEDI9600) to block anti-platelet antibody induced thrombocytopenia was examined Treatment of the FcγRIIA transgenic mice with anti-platelet antibody caused a rapid depletion of platelets (FIG. 10A). Prophylactic dosing with the optimized IV.3 Ab (MEDI9600) significantly blocked platelet clearance in this model (FIG. 10B, 10C). Importantly, the inhibition of platelet depletion with MEDI9600 was associated with the internalization of FcγRIIA on the platelets.

Taken together, these data indicate that humanized anti-FcγRIIA antibody, MEDI9600, inhibits anti-platelet antibody-induced thrombocytopenia in vivo, and support the use of this antibody for the treatment of immune thrombocytopenia.

Example 8. Blockade of FcγRIIA by MEDI9600 has No Adverse Effects on Neutrophil Function Neutrophils play a critical role in host defense by sensing infection and tissue injury, and initiating an acute inflammatory response, which serves to recruit leukocytes, clear infections, engage the adaptive immune system, and promote repair. Upon exposure to an insult, neutrophils rapidly migrate through the blood vessels to the site of the tissue injury, following chemical signals derived from pathogens and damaged host cells. Neutrophils directly engage pathogens through interactions with pattern recognition receptors, complement receptors, and immunoglobulin receptors, which results in the release of toxic substances that kill pathogens and/or the clearance of the pathogens by phagocytosis. Since neutrophil functions are important in host defense, we assessed the impact of FcγRIIA blockade with MEDI9600 on different neutrophil functions.

Figure 11A:
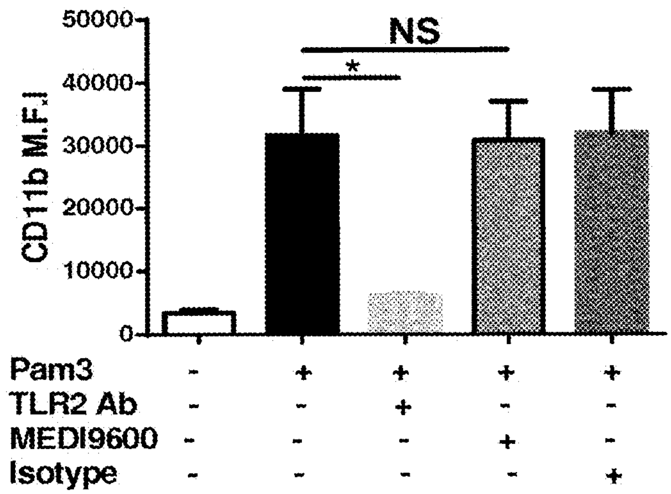
FIGS. 11A-11C show that blockade of FcγRIIA by MEDI9600 has no adverse effects on neutrophil function.

First, we examined if blockade of FcγRIIA would affect neutrophil activation in the presence of the synthetic triacylated lipoprotein Pam3Sk4, which is a toll-like receptor 2 (TLR2) agonist and mimic of the acylated amino terminus of bacterial lipoproteins. An anti-TLR2 Ab inhibited the Pam3 Sk4-induced neutrophil activation, whereas the MEDI9600 anti-FcγRIIA antibody and the isotype control IgG antibody had no effect on TLR2-mediated neutrophil activation (FIG. 11A).

Figure 11B:
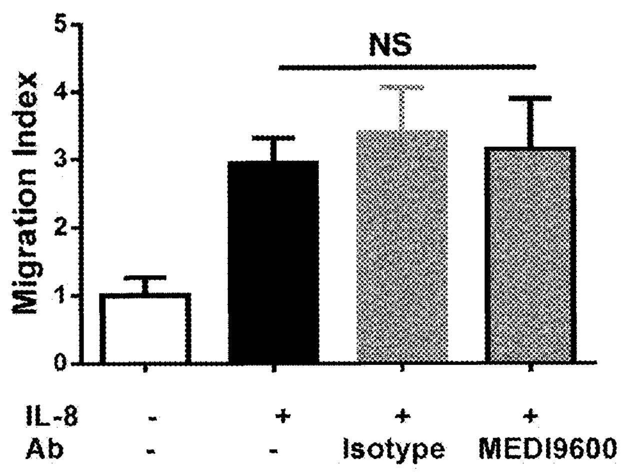

Next, we examined if blockade of FcγRIIA would affect IL-8-induced neutrophil migration. IL-8-induced neutrophil migration was not impacted by MEDI9600 or the control antibody (FIG. 11B).

Figure 11C:
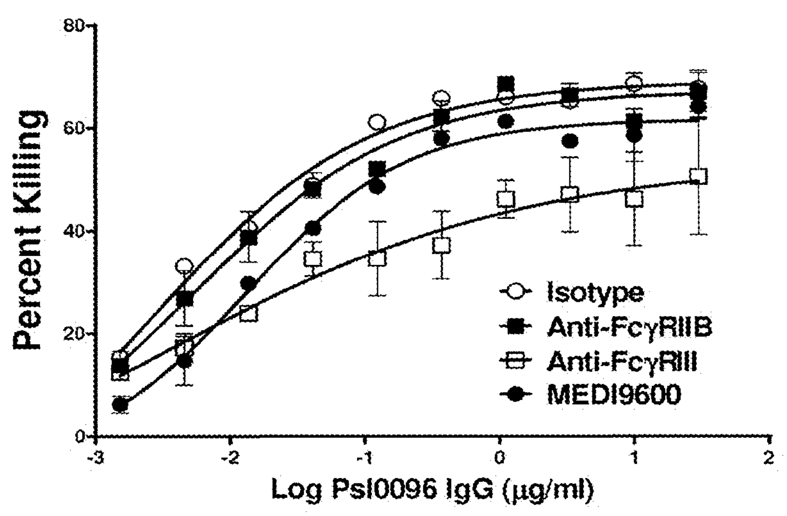

Finally, we examined if MEDI9600 affects anti-Psl mAb-mediated opsonophagocytic killing (OPK) of *Pseudomonas aeruginosa*. Anti-Psl mAbs were previously shown to mediate potent complement dependent killing of *P. aeruginosa* in the presence of neutrophils[16]. A luminescent *P. aeruginosa* strain was used in this assay to assess bacterial killing. The level of luminescence correlates with the frequency of live bacteria. Neutrophils were pre-incubated with MEDI9600, anti-FcγRIIB Ab, or anti-FcγRIII Ab, and then they were incubated with luminescent bacteria for 2 hours. MEDI9600 had a minimal effect on the ability of neutrophils to kill *P. aeruginosa* in the presence of anti-Psl mAb Ps10096, whereas blockade of FcγRIII clearly inhibited OPK activity (FIG. 11C). These data indicate that antibody-mediated phagocytosis of a clinically resistant strain of bacteria is largely independent of FcγIIA, and blockade of this receptor is not predicted to adversely impact phagocytosis of bacteria by neutrophils.

Taken together, these data indicate that FcγRIIA blockade will not adversely impact normal neutrophil functions such as chemotaxis, activation induced by pathogen associated molecular patterns, and phagocytosis.

Figure 12:
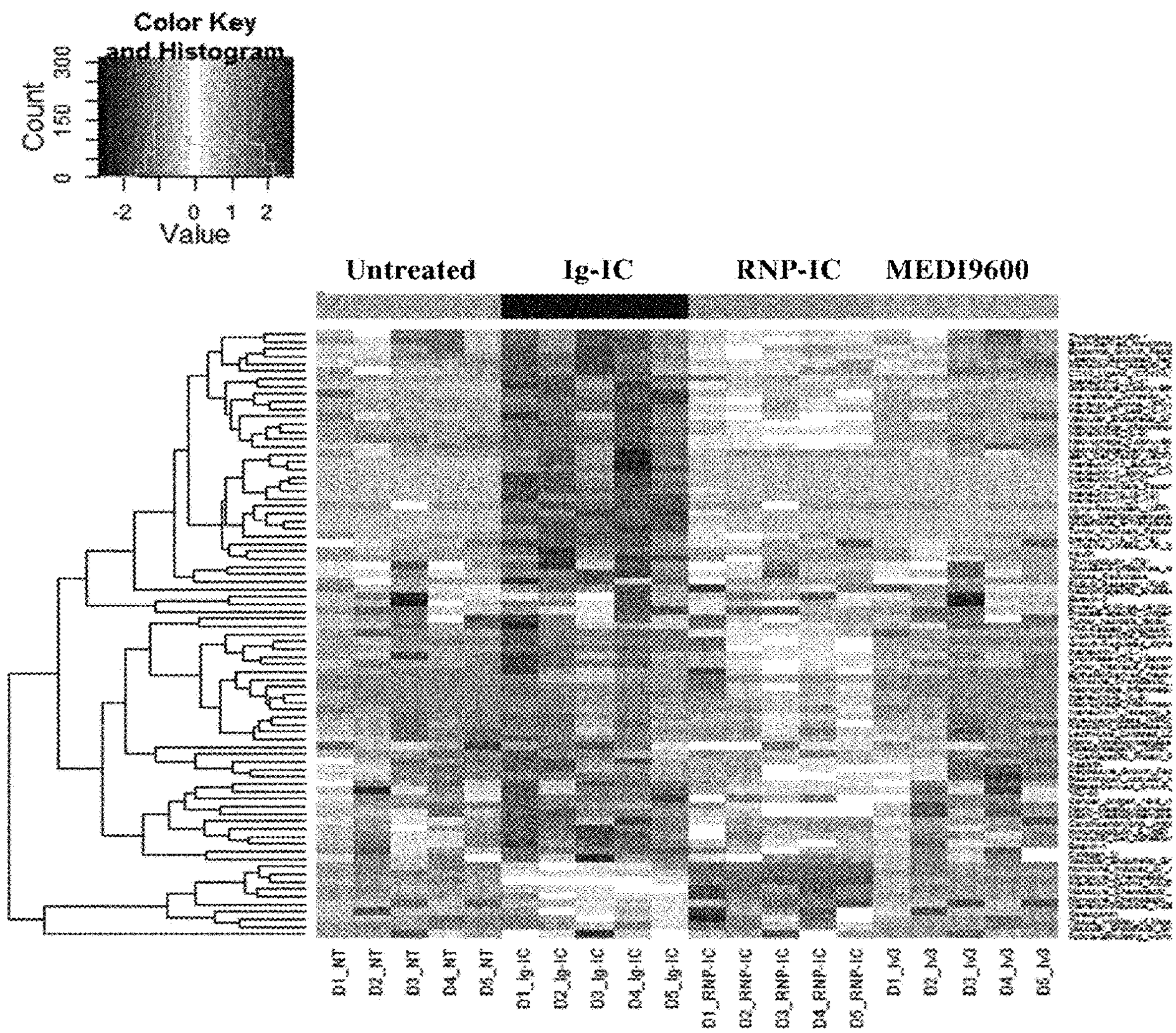
FIG. 12 shows that ex vivo treatment of human whole blood with MEDI9600 alone has no effect on the protein expression profile.

Example 9. MEDI9600 has No Impact on Protein Induction from Cells in Whole Blood Adverse effects of antibody treatments, such as cytokine storms, can be detected by examining the protein profile of whole blood. To assess the impact of MEDI9600, the gene expression profiles of unstimulated whole blood, and whole blood stimulated by MEDI9600, Ig-IC, or RNP-IC were assessed in five normal health donors. The Ig-IC or RNP-IC had a profound impact on the protein expression profile, and as expected, there were no differences in the expression profile between the untreated and MEDI9600-stimulated conditions (FIG. 12). These data indicate that MEDI9600 does not activate cells in whole blood, and are indicative of a good safety profile.

Example 10. MEDI9600: A Single-Dose Pharmacokinetic and Exploratory Pharmaco-Dynamic Study in Cynomolgus Monkeys The purpose of this study was to characterize the pharmacokinetic/pharmacodynamic relationship of MEDI9600 in cynomolgus monkeys when given as a single dose by intravenous injection. Results of this study were used to inform pharmacokinetic/pharmacodynamic modeling, which supported administration of MEDI9600 to humans.

Figure 13A:
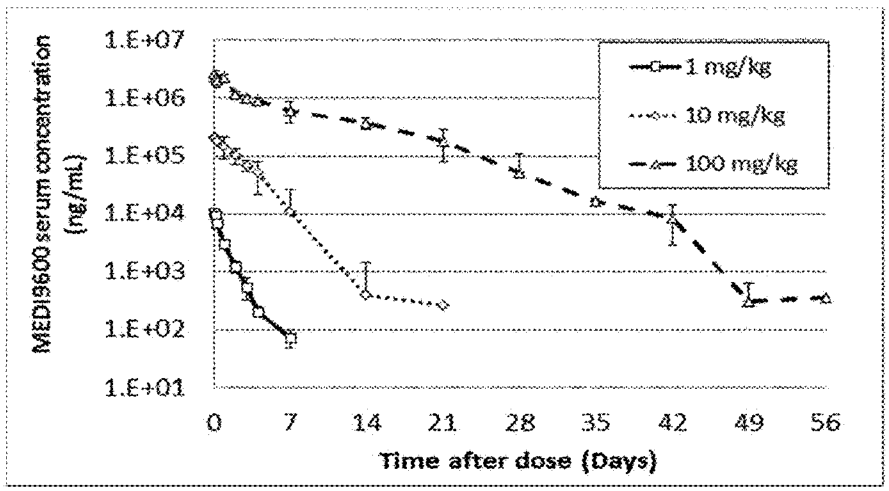
FIGS. 13A-13C show the results of a single-dose pharmacokinetic and exploratory pharmaco-dynamic study of MEDI9600.

The pharmacokinetics were nonlinear; an inspection of Cmax/Dose, AUC (0-∞)/Dose, and half-life show a clear trend for these to increase with dose (FIG. 13A). The terminal half-lives obtained from the non-compartmental analysis were shorter than expected for a human IgG1 antibody in the cynomolgus monkey, with those for the group given 1 mg/kg only 1.08-1.2 days, increasing to 2.84-4.3 days for the group given 100 mg/kg. However, the tendency for the half-life to increase with dose, along with an inspection of the pharmacokinetic curves, reveals a pharmacokinetic profile consistent with target-mediated elimination of the antibody. For the highest dose of 100 mg/kg, which had less interference from target-mediated elimination, initial volumes of distribution of 0.024-0.052 L/kg were similar to plasma volume, as would be expected for a human IgG1 antibody. Pharmacokinetic variability appears low, with coefficient of variation values around 20% or less for the earlier samples. Pharmacokinetics became markedly more variable approaching the terminal phase.

Figure 13B:
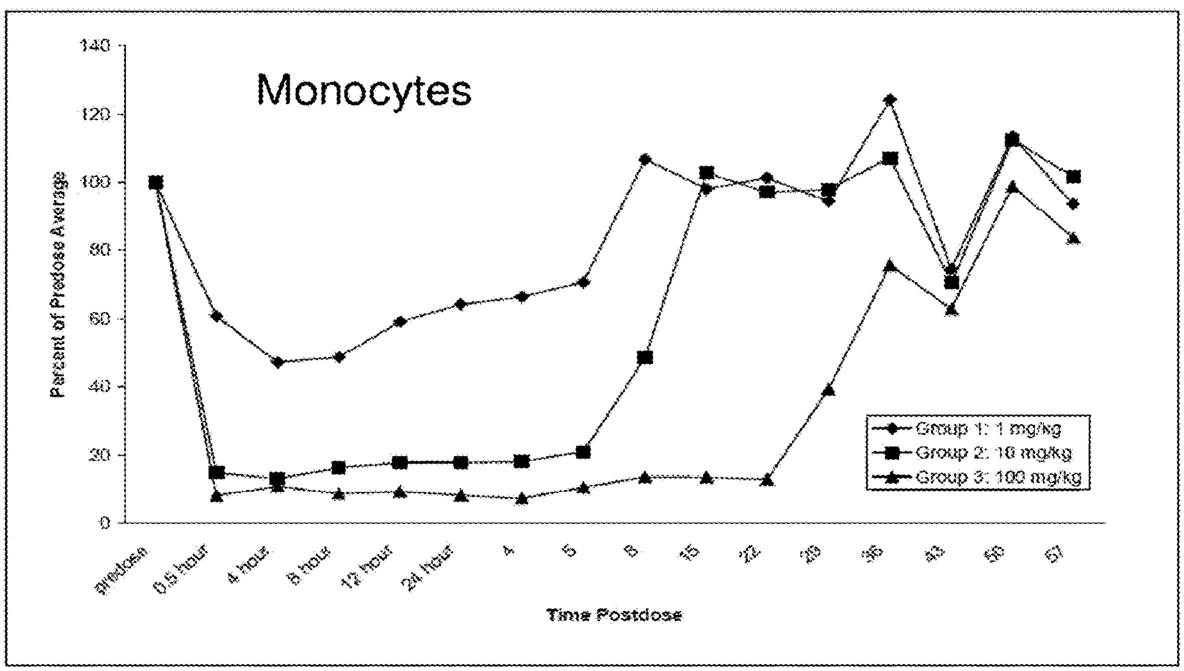
Figure 13C:
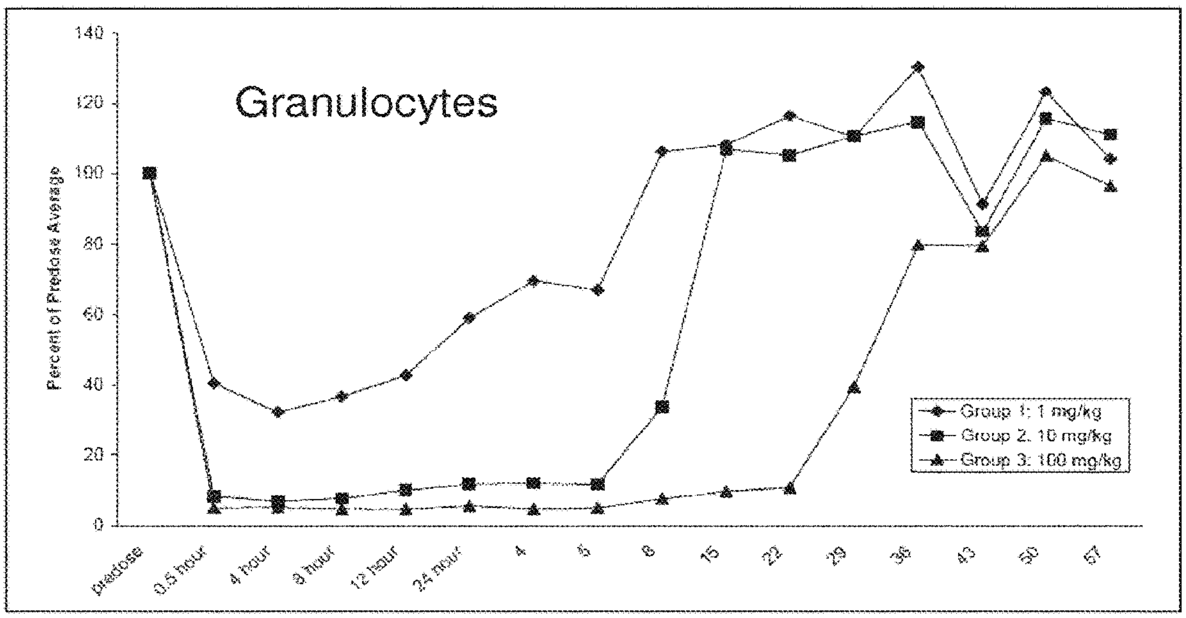

A single dose of MEDI9600 administered at 1, 10, or 100 mg/kg induced a dose-response reduction of FcγRIIA fluorescence intensity on monocytes and granulocytes (FIG. 13B, 13C). This reduction was completely reversible, with a full recovery achieved first in animals given 1 mg/kg, followed by animals given 10 mg/kg, and animals given 100 mg/kg. FcγRIIA expression on monocytes and granulocytes showed a dose-dependent suppression on dosing with MEDI9600, and was similar for monocytes and granulocytes. Suppression was observed by the 30-minute time point, indicating a rapid suppression in dosing. This suppression was only partial for Group 1 (1 mg/kg) but appeared to cause maximum suppression for Groups 2 and 3, judging by the similar suppression achieved by these dose levels at their nadir. FcγRIIA expression levels returned to baseline over a dose-dependent period of days to weeks. It was notable that this rapid suppression and slower recovery mirrored the pharmacokinetic profile of MEDI9600. In particular, the recovery to baseline of FcγRIIA expression matched the reduction of pharmacokinetic exposure to concentrations of below 1,000 ng/ml; this occurred at around 7 days post-dose for Group 1, around 14 days post-dose for Group 2, and around 49 days post-dose for Group 3, indicating a strong and direct relationship between pharmacokinetic exposure and pharmacodynamic response in the form of FcγRIIA expression.

To summarize, male monkeys were given MEDI9600 once at a dose level of 1, 10 or 100 mg/kg with a dose volume of 2 mL/kg via intravenous injection. Administration of MEDI9600 resulted in dose-dependent suppression of FcγRIIA expression on monocytes and granulocytes, followed by a slow recovery to baseline levels consistent with the duration of the MEDI9600 pharmacokinetic exposure, indicating a strong relationship between pharmacokinetic exposure and pharmacodynamic response.

In addition, safety end points were also evaluated during the study; administration of MEDI9600 had no effect on D-dimer concentrations or on clinical observations, including qualitative food consumption, body weights, hematology, coagulation, and clinical chemistry tests. MEDI9600-related transient erythema and edema at the injection site was considered non-adverse.

Example 11. Materials and Methods

Cynomolgus Monkey FcγRIIA Sequencing

Primers were designed using the available cynomolgus monkey draft genome sequence derived from a single animal of Vietnamese origin (Beijing Genome Institute, 2011). The Protein Science cynomolgus genomic DNA bank, comprised of 60 individuals (20 Chinese, 20 Vietnamese, 20 Mauritian), was utilized to sequence FcγIIA. PCR amplification was performed using Qiagen HotStar Taq Master Mix followed by in-house sequencing of the PCR products. Raw sequence alignments, consensus transcript builds, SNP variant identification, and comparison to human FcγIIA (CCDS 44264/UniProt P12318) were completed using SeqMan (Lasergene) and CloneManager software.

Sequence variation was confirmed using an internal cynomolgus genome browser, which contains whole exome sequence data from 48 individuals (16 Chinese, 16 Vietnamese, 16 Mauritian). Minor allele frequencies derived from this internal database are shown in Table 4. FcγIIA exon arrangement was confirmed using blood-derived cDNA from 6 individuals.

Fcγ Receptor Binding Assay

Recombinant FcγRI, FcγRIIA-131H/H allotype, FcγRIIB, FcγRIII-158F allotype, and FcγRIII-158V allotype, were generated at MedImmune. Anti-FcγRIII antibody (3G8) was purchased from Abcam (Cambridge, Mass.). Anti-FcγRI Ab (16-115) was purchased from Antibodies-online (Atlanta, Ga.). Anti-FcγRIIB Ab and isotype control R347-Tm were generated at MedImmune.

Costar 96-well microplates (Fisher Scientific, PA) were coated with 2 μg/ml of Fcγ Receptor (FcγRI, FcγRIIA-131H/H allotype, FcγRIIB, FcγRIII-158F allotype, or FcγRIII-158V allotype) overnight at 4° C. Plates were washed five times with 200 μl of wash buffer (PBS containing 0.1% Tween 20), blocked with blocking buffer containing 5% milk in PBS for 1 hour at room temperature, and washed five additional times with wash buffer. Three-fold serial dilutions of the test antibody or control antibody (R347-Tm) were added to wells in duplicate. Plates were incubated for 2 hours at room temperature, and washed five times with wash buffer. Binding of the antibodies to the FcγRs was detected by adding 50 μl of goat anti-human Fc-HRP (Jackson ImmunoResearch Laboratories, PA) to the wells and incubating for 1 hour at room temperature, washing 10 times, and adding 50 μl TMB substrate (Pierce Biotechnology, MA). The color reaction was stopped with 50 μl 0.2M $H_{2S}SO_4$ and the absorbance was measured using a spectrophotometer (Molecular Devices, CA) at $A_{405\ nm}$.

Epitope Competition Assay

To identify IgG improvements during Lead Optimisation, antibody samples were assessed using an epitope competition assay using homogenous time-resolved fluorescence (HTRF®, Cisbio International) in which the binding of IV.3 IgG (Stemcell Technologies, 01470) to biotinylated human CD32a 131H was measured.

The binding of IV.3 IgG to biotinylated human CD32a 131H was assessed by measuring the FRET signal between a IV.3 and biotinylated human CD32a 131H using DyLight 649 conjugated anti-mouse detection antibody streptavidin Terbium cryptate (Cisbio International, 610SATLB) detection. The assay was used to identify improvements in crude IgG samples by measuring inhibition of the interaction between IV.3 IgG and biotinylated human CD32a 131H.

An 8.0 nM solution of IV.3 IgG is prepared in assay buffer consisting of PBS (Invitrogen 14190-185), 0.2% BSA (Sigma A9576) and 0.4 M KF (BDH 103444T). 5 μl is added to the assay plate (384 black, shallow well, Costar, 3676), to give a final concentration of 2.0 nM. A 40 nM solution of DyLight 649 conjugated anti-mouse detection antibody is prepared in assay buffer and 5 μl is added to the assay plate to give a final concentration of 10 nM. 5 μl of each IgG sample is transferred to the assay plate using a MiniTrak™ (Perkin Elmer). A pre-mixed solution containing 4 nM biotinylated human CD32a 131H and 2.67 nM streptavidin Terbium cryptate is prepared as a 4× stock. 5 μl is added to the assay plate to give a final concentration of 1 nM biotinylated human CD32a 131H and 0.67 nM streptavidin Terbium cryptate. Non-specific binding wells (negative controls) were defined for each plate by omitting biotinylated human CD32a 131H. Assay plates were incubated for 3 hours at room temperature prior to reading time resolved fluorescence at 620 nm and 665 nm emission wavelengths using an EnVision plate reader (Perkin Elmer).

Data was analysed by calculating the 665/620 nm ratio followed by the % Delta F values for each sample.

The 665/620 nm ratio was used to correct for sample interference using Equation 1.

$$665/620 \text{ nm ratio} = \left(\frac{665 \text{ nm signal}}{620 \text{ nm signal}}\right) \times 10{,}000 \qquad \text{Equation 1}$$

The % Delta F for each sample was then calculated using Equation 2.

$$\text{Delta } F(\%) = \left(\frac{\text{sample } 665/620 \text{ nm ratio} - \text{negative control } 665/620 \text{ nm ratio}}{\text{negative control } 665/620 \text{ nm ratio}}\right) \times 100 \qquad \text{Equation 2}$$

% A Specific binding was calculated using Equation 3.

% specific binding=% Delta $F$ of sample×100% Delta $F$ of total binding control     Equation 3:

To confirm improvements, crude or purified IgG samples were assessed in the same assay by serially diluting samples in assay buffer using a Greiner 384 well V bottom plate (Greiner 781280). 5 μl of each dilution of scFv was transferred in duplicate to the assay plate (384 black, shallow well, Costar, 3676) using a Bravo™ (Agilent). Assay reagents were then added as described above.

Data was analysed by calculating the 665/620 nm ratio followed by the % Delta F values as described previously. The 665/620 nm ratio was used to correct for sample interference as described in Equation 1. % Delta F was calculated using Equation 2. % Specific binding was calculated for each condition using Equation 3.

$IC_{50}$ values were determined using GraphPad Prism software by curve fitting using a four-parameter logistic equation (Equation 4).

$Y$=Bottom+(Top−Bottom)/(1+10^((Log EC50−$X$)*Hill Slope))     Equation 4:

X is the logarithm of concentration. Y is specific binding Y starts at Bottom and goes to Top with a sigmoid shape.

HTRF Binding Assay for Selectivity and Cross-Reactivity

The selectivity of lead antibodies was assessed using a homogenous time-resolved fluorescence assay (HTRF®, Cisbio International) in which the binding of the IgG to biotinylated human CD32b was measured. Cross-reactivity was assessed using a homogenous time-resolved fluorescence assay in which the binding of the IgG to cyno CD32a and CD32b was measured.

The binding of purified IgG to biotinylated CD32 was assessed by measuring the FRET signal between the IgG and the biotinylated CD32 using streptavidin terbium cryptate (Cisbio International, 610SATLB) and anti-human Fc antibody conjugated with XL665 (Cisbio International, 61HFCXLB) detection reagents.

Assay buffer consisting of PBS (Invitrogen 14190-185), 0.2% BSA (Sigma A9576) and 0.4 M KF (BDH103444T) is prepared and 5 μl added to the assay plate (384 black, shallow well, Costar, 3676). CD32 is diluted as a 4× working stock solution in assay buffer. Human CD32b, cyno CD32a and cyno CD32b are prepared at 20 nM and 5 μl added to the assay plate to give a final concentration of 5 nM. Serial dilutions of IgGs are prepared in duplicate in assay buffer using a Greiner 384 well V bottom plate (Greiner 781280) and 5 μl of each dilution of peptide transferred to the assay plate using a Bravo™ (Agilent). Streptavidin terbium cryptate and anti-human Fc IgG XL665 were diluted to 0.67 nM and 15 nM respectively (final concentrations) in assay buffer and 5 μl of this premixed solution was added to the assay plate. A negative control was defined for each plate by replacing sample IgG with 5 μl assay buffer. Assay plates were incubated for 3 hours at room temperature prior to reading time resolved fluorescence at 620 nm and 665 nm emission wavelengths using an EnVision plate reader (Perkin Elmer).

Data was analysed by calculating the 665/620 nm ratio followed by the % Delta F values as described previously (see epitope competition protocol for equations). The 665/620 nm ratio was used to correct for sample interference as described in Equation 1. % Delta F was calculated using Equation 2. % Specific binding was calculated for each condition using Equation 3.

Octet IgG Quantification

IgG samples were quantified using Protein A Biosensors (ForteBio) in conjunction with the OctetRED384 system (ForteBio).

25 μl of sample is mixed with 25 μl assay buffer consisting of PBS, 0.02% Tween20, 1 mg/ml BSA (0.1%). The rate of binding of IgG in the sample to the protein A biosensor is measured by Bio-Layer Interferometry (BLI). An IgG standard curve is generated using a control IgG of known concentration and preparing a 12-point 1 in 2 dilution series from a top final concentration of 500 μg/ml. The Octet system software calculates the binding rates from standards with known concentrations to generate a standard curve. The binding rate is proportional to the standard concentration.

Data is analysed using Data Analysis software package provided with the OctetRED384 system. Data is uploaded into the software and analysis performed using initial slope and the Dose Response—4PL (Default; Unweighted) equations. Unknown concentrations are calculated from comparison with the standard curve.

Binding Competition Assay with IVIG

Human neutrophils were re-suspended in blocking buffer [phosphate-buffered saline (PBS) supplemented with 10% fetal bovine serum] and transferred to round-bottom 96-well culture plates (0.5×106 cells/well). Cells were incubated with increasing concentrations of fluorescently labeled MEDI9600 or the R347-Tm control antibody (ranging from 0.0003 to 66.67 nM) for 30 minutes at 4° C. in the presence or absence of 10 mg/mL of Intravenous Immunoglobulin (IVIG). After incubation, cells were washed with cold PBS and the mean fluorescence intensity (MFI) of cell-bound antibodies was assessed by flow cytometry using an LSRII (BD; Franklin Lakes, N.J.). The $EC_{50}$ for binding was calculated using a non-linear fit equation in GraphPad Prism 6 software.

Whole Blood Internalization Assay

To demonstrate MEDI9600-mediated FcγRIIA internalization in human monocytes by confocal microscopy, human peripheral blood mononuclear cells (PBMCs) were isolated from whole blood that was collected into CPT tubes. The PBMCs were first stained with CD14-Alexa 488, and CD14-positive monocytes were sorted. The cells were then stained with MEDI9600-Alexa 647 on ice for 30 min, washed once and incubated at room temperature for confocal microscopy. Cell imaging was performed using a Leica TCS SP5 confocal system consisting of a Leica DMI6000 B inverted microscope (Leica Microsystems). Images were acquired at time-points noted in the figure legends and were analyzed using the LAS AF version 2.2.1 Leica Application Suite software (Leica Microsystems).

Anti-FcγRIIA-Tm Ab-mediated receptor internalization was examined by a FACS-based assay. Human or cynomolgus monkey blood was collected into heparin tubes. A three-fold dilution series of unlabeled anti-FcγRIIA antibody or control antibody was added to 50 μl whole blood for 2 hours at 37° C. The whole blood was washed with FACS buffer (5% fetal bovine serum in PBS), and stained with Ab cocktail (CD14-PE, CD20-Pacific Blue, and IV.3-Alexa 647) on ice for 1 hour. After washing, the cells were incubated with 1 ml RBC lysis buffer (Biolegend, CA) at room temperature for 3 minutes, washed and re-suspended in 150 μl FACS buffer. FcγRIIA surface expression on human or cynomolgus monkey monocytes was measured on a FACS LSRII flow cytometer (BD Bioscience, CA) and analysis was performed using Flowjo software.

Ribonucleoprotein-Immune Complex (RNP-IC)-Induced Type I IFNα Assay

The impact of FcγRIIA blockade on RNP-IC-induced IFNα expression was examined by ELISA. Briefly, 100 μl human or cynomolgous monkey PBMC ($5\times10^6$ cell/ml) were incubated in a tissue culture flask for 1 hour. Non-adherent cells were collected, and this monocyte-depleted fraction was incubated with anti-FcγRIIA Abs or its isotype control (R347-Tm Ab) from 300 μg/ml to 0.001 μg/ml with 3-fold dilution at 37° C. incubator for 2 hours. Cells were then treated with 100 μl RNP-IC (1 μg/ml RNP (Biomeda)/2% anti-RNP antibody seropositive SLE serum) for 16 hours. Concentrations of IFNα in the cell culture supernatants were determined using a human IFNα ELISA kit (PBL Assay Science, NJ).

Isolation of Human Neutrophils

Peripheral blood from normal volunteers was drawn into vacutainer tubes containing heparin, and the blood was diluted 1:1 in HBSS. Neutrophils were separated by centrifugation on a lymphoprep density gradient. Erythrocytes were removed by RBC lysis buffer (Biolegend, CA). Neutrophils were further enriched using the Human Neutrophil Enrichment Kit (StemCell Technologies, CA).

Detection of Superoxide Production Using the Ferri-Cytochrome C Reduction Assay

Neutrophil superoxide production induced by anti-neutrophil cytoplasmic antibody (ANCA) or phorbol myristate acetate (PMA) was measured by the ferri-cytochrome C reduction assay. Briefly, isolated human neutrophils were suspended at $4\times10^6$ cells/ml in HBSS/20 mM Hepes/$Ca^{2+}$, $Mg^{2+}$ free buffer, and primed with recombinant 2 ng/ml TNF-α (R&D Systems, MN) for 15 minutes. To assess the effects of FcγRIIA blockade, neutrophils were pre-incubated with 10 μg/ml MED19600 for 30 min at room temperature before they were added to the 96 well tissue culture plates. The 96-well tissue culture plates were pre-treated with 100 μl of 0.5% milk in HBSS/20 mM Hepes for 1 hour at room temperature. Plates were washed three times with wash buffer (HBSS/20 mM Hepes/$Ca^{2+}$, $Mg^{2+}$ free buffer). Fifty microliters of 2×Cytochrome C buffer (0.2 mM Cytochrome C, 1 mM $MgCl_2$, 2 mM $CaCl_2$)) were added to each well, followed by 10 μl of stimulus (10 μg/ml of anti-PR3 Ab, 30 μg/ml of anti-MPO Ab, at or 20 nM PMA) and 50 μl of neutrophils. The plate was immediately put into a pre-warmed plate reader (37° C.), and OD (550 nm and 490 nm) was measured continuously for 2 hours at 37° C.

Detection of Superoxide Production Using the Flow Cytometry (DHR 123 Assay)

Neutrophil superoxide production induced by ANCA was measured by flow cytometry. Neutrophils ($1\times10^5$/ml) were resuspended in RPMI 1640 buffer with 1 μg/ml dihydrohodamine 123 (DHR) (Life Technologies, CA). Some cells were pre-incubated with 10 μg/ml MED19600, anti-FcγRIII Ab (Biolegend, CA), or isotype control Ab at room temperature for 30 minutes. The cells were then incubated for 30 minutes at 37° C. with 30 μg/ml anti-MPO Ab (Abcam, MA), 10 μg/ml anti-PR3 Ab (Abcam, MA), or 80 μg/ml IgG purified from sera of healthy volunteers or AAV patients (Tissue Solutions, UK), pelleted at 200 g, and resuspended in ice-cold HBSS at a density of $5\times10^6$ cells/ml. Mean fluorescence intensity (M.F.I) was measured by LSRII flow cytometer (BD Bioscience, CA) and analysis was performed using Flowjo software.

Neutrophil Migration Assay

Neutrophil migration was assessed using a 96-well Chemo TX system with 5 μm filter (Neuro Probe, MD). Human IL-8 (R&D Systems, MN) was diluted in RPMI 1640 containing 1% BSA to a final concentration of 20 nM and placed in the lower chamber. Cells were washed and suspended in the same medium. Human neutrophils were incubated with 10 μg/ml MED19600 or isotype control antibody for 30 minutes at 37° C. before the cells were added to the upper chamber. Neutrophils were allowed to migrate for 1 hour. Cells that migrated to the lower chamber were enumerated by flow cytometry. The migration index is the ratio of the number of cells that migrate in response to the chemotactic agent versus the number of cells that migrate in its absence.

Neutrophil Activation Assay

Human blood was collected in EDTA tubes, and 50 μl aliquots of blood were incubated with Anti-TLR2 Ab, MEDI9600, or isotype control Ab at 10 μg/ml for 2 hours at 37° C. Fifty microliters of Pam3CSK4 (Invivogen, CA) were added to the whole blood to a final concentration of 100 ng/ml and incubated for 45 minutes. The cells were washed two times in FACS buffer (3% FBS in PBS), stained with CD11b-PE (Biolegend, CA) on ice for 30 minutes, and washed once with FACS buffer. Red blood cells were lysed with lysis/Fix buffer (BD Bioscience, CA). CDllb expression in the neutrophils was measured by flow cytometry.

Opsonophagocytic Killing (OPK) Assay

Luminescent *P. aeruginosa* were constructed using vector mini-CTX-lac-lux as previously described (DiGiandomenico et al., *J. Exp. Med.* 209:1273-1287 (2012)). *P. aeruginosa* strains were grown to single colony on overnight plates of trypticase soy agar (TSA) at 37° C., followed by inoculation of a single colony into 10 mL Luria Bertani (LB)

broth, and grown to an optical density at 650 nm of 0.4 (approximately $5\times10^8$ colony forming units [CFU]/mL). One milliliter of cells was pelleted by centrifugation at 14,000×g, followed by suspension in OPK assay buffer, and further diluted 1:200 (approximately $2.5\times10^6$ CFU/mL). Bacteria were kept on ice until preparation of all OPK components was completed.

Baby rabbit serum (BRS) (CedarLane, Hornby, Ontario, Canada) was used as the complement source for OPK assays. One milliliter of lyophilized BRS was reconstituted with ice-cold distilled water, followed by preparation of a 1:10 dilution in OPK assay buffer. Diluted BRS was kept on ice until preparation of all OPK components was completed.

MEDI9600 (anti-FcγRIIA), H2B (anti-FcγRIIB), or 3G8 (anti-FcγRIII) Ab was added to white flat-bottom 96-well plates (12.5 μl per well), followed by the addition of 12.5 μl of the primary neutrophil preparation. The final concentration of FcγR mAbs and primary neutrophils was 2 μg/ml and $2\times10^7$ cells/ml, respectively. After 20-minute incubation at room temperature, dilutions of the anti-Psl antibody, diluted complement, and bacteria were added to each well, and the plate was covered with a breathable sealing film. Wells lacking anti-Psl mAb antibody served as assay controls. Plates were incubated for 120 minutes at 37° C. with shaking at 250 revolutions per minute (rpm). Following the incubation, relative luciferase units (RLU) were measured using the Perkin Elmer Envision Multi-Label Reader. The amount of luminescence correlates directly with the frequency of viable bacteria remaining in culture. All samples were run in duplicate. Percent killing of *P. aeruginosa* was calculated using the following formula:

% Killing=100−([RLU experimental wells/RLU control wells]×100)

$EC_{50}$ values were calculated with GraphPad Prism (version 5) using a 4-parameter logistic, nonlinear regression model for curve fitting analysis.

Whole Blood Proteomic Assessment

Human blood was collected in heparin tubes. Five milliliters of blood was incubated with anti-FcγRIIA Ab (30 μg/ml), RNP-IC (1 μg/ml RNP/2% anti-RNP antibody seropositive SLE serum), or Ig-IC (100 μg/ml biotinylated-NMGC Ab-Streptavidin, 2:1 mol:mol ratio) for 16 hours at 37° C. The plasma fraction was collected after centrifugation for 10 minutes at 1300 g. Over 200 protein analytes were measured using Rules-Based-Medicine Discovery MAP (Austin, Tex.). Data was generated from five individual donors: two 131H/H donors, two 131 R/R donors, and one 131 H/R donor, which covered all the FcγRIIA polymorphic variants.

Passive Immune Thrombocytopenia Animal Model

The effect of anti-FcγRIIA Ab on anti-platelet antibody-induced thrombocytopenia was measured in a passive immune thrombocytopenia animal model. Wild-type and FcγRIIA transgenic mice were obtained from The Jackson Laboratory. Rat anti-mouse CD41 (GpIIa) IgG1 Ab and control rat IgG1 Ab were purchased from BD Bioscience. Wild-type and transgenic mice were injected intraperitoneally with 2 μg of anti-CD41 at day 0. Some mice were pretreated 24 hours prior with MEDI9600 at 10 mg/kg. Blood was collected at day 1, day 5, day 8, and day 12 by retro-orbital bleeding, and platelets were counted using the Sysmex hematology analyzer. Platelet FcγRIIA expression was determined by flow cytometry. MEDI9600: A Single-Dose Pharmacokinetic and Exploratory Pharmacodynamics Study in the Cynomolgus Monkey Male cynomolgus monkeys were assigned to groups and administered MEDI9600, as indicated in Table 9. Animals were dosed via intravenous injection.

TABLE 9

| Group | No. of Animals (Male) | Dose Level (mg/kg) | Dose Vol. (mL/kg) | Dose Conc. (mg/mL) |
|---|---|---|---|---|
| 1 (Low IV) | 3 | 1 | 2 | 0.5 |
| 2 (Mid IV) | 3 | 10 | 2 | 5.0 |
| 3 (High IV) | 3 | 100 | 2 | 49.3[a] |

IV = Intravenous

[a]Animals in Group 3 received the test article as supplied by the sponsor (nominal concentration of 50 mg/mL) with no further adjustment of dose volume.

Quantitative Determination of MEDI9600 in Cynomolgus Monkey Serum Using an Enzyme-Linked Immunosorbent Assay (ELISA) (Non-GLP)

This method utilized an indirect ELISA format to measure the concentration of MEDI9600 in cynomolgus monkey serum. Standards, controls, and test samples were incubated with sheep anti-human IgG (H+L) that had been immobilized on a microtiter plate. After incubation, unbound material was washed away and MEDI9600 was detected using goat anti-human IgG-(H+L)-HRP conjugate, and visualized with the addition of a tetramethylbenzidine (TMB) substrate solution. The color development was stopped, and the intensity of the color was measured at 450/650 nm.

Pharmacodynamics—Flow Cytometry

Blood (approximately 1 mL) was collected for flow cytometry via a femoral vein from all animals on Days 12 and 20 of the pre-dose phase; at approximately 0.5 hours, 4 hours, 8 hours, and 24 hours post-dose; once on Days 3, 4, 5, and 8 of the dosing phase; and weekly thereafter (based on Day 1 of the dosing phase). Animals were not fasted unless samples were collected in conjunction with clinical pathology sampling. The anticoagulant was acid-citrate-dextrose. Parameters were expressed as percentages (of total CD45+ white blood cells) and absolute values (cells/μL). FcγRIIA expression levels were described in fluorescence intensity and in calculated molecules of equivalent soluble fluorescence (MESF) values using median and/or geometric mean fluorescence intensity values. The lymphocyte subsets shown in Table 10 were quantitated using flow cytometry.

TABLE 10

| Lymphocyte Subset | Phenotype |
|---|---|
| CD14+ monocytes[a] | CD3− CD14+ |
| CD32+ monocytes[a] | CD3− CD14+ CD32a+[a] |
| Granulocytes[a] | SSC/CD45+ CD3− |
| CD32+ granulocytes[a] | SSC/CD45+ CD3− CD32a+[a] |
| Total White blood cells | CD45+ |

Note:

All populations were derived from FSC/SSC and/or SSC/CD45 gates.

Results were enumerated as percent relative (% of total CD45+ white blood cells) and absolute (cells/μL) values for each phenotype.

[a]Median and/or geometric fluorescence intensity values for C FcγRIIA were also used Statistical Analysis The statistical significance of the difference between two groups was analyzed using unpaired Student's t-test or non-parametric Mann Whitney test. Statistical significance was ascribed to the data when $p<0.05$.

REFERENCES

1. Nimmerjahn et al. Fc-gamma receptors as regulators of immune responses. Nat Rev Immunol. 2008 January; 8(1):34-47.

2. Hogarth et al. Fc receptor-targeted therapies for the treatment of inflammation, cancer and beyond. Nat Rev Drug Discov. 2012 Mar. 30; 11(4):311-31.
3. Bruhns et al. Properties of mouse and human IgG receptors and their contribution to disease models. Blood. 2012 Jun. 14; 119(24):5640-9.
4. Schiffenbauer et al. Biomarkers, surrogate markers, and design of clinical trials of new therapies for systemic lupus erythematosus. Arthritis Rheum. 2004 August; 50(8):2415-22.
5. Means et al. Human lupus autoantibody-DNA complexes activate DCs through cooperation of CD32 and TLR9. J Clin Invest. 2005 February; 115(2):407-17.
6. Bennett et al. Interferon and granulopoiesis signatures in systemic lupus erythematosus blood. J Exp Med. 2003 Mar. 17; 197(6):711-23.
7. Båve et al. Fc gamma RIIa is expressed on natural IFN-alpha-producing cells (plasmacytoid dendritic cells) and is required for the IFN-alpha production induced by apoptotic cells combined with lupus IgG. J Immunol. 2003 Sep. 15; 171(6):3296-302.
8. Kallenberg et al. Pathogenesis of ANCA-associated vasculitis: new possibilities for intervention. Am J Kidney Dis. 2013 December; 62(6):1176-87.
9. Porges et al. Anti-neutrophil cytoplasmic antibodies engage and activate human neutrophils via Fc gamma RIIa. J Immunol. 1994 Aug. 1; 153(3):1271-80.
10. Chen et al. Endocytosis of soluble immune complexes leads to their clearance by FcγRIIIB but induces neutrophil extracellular traps via FcγRIIA in vivo. Blood. 2012 Nov. 22; 120(22):4421-3.
11. Reilly et al. Heparin-induced thrombocytopenia/thrombosis in a transgenic mouse model requires human platelet factor 4 and platelet activation through FcgammaRIIA. Blood. 2001 Oct. 15; 98(8):2442-7.
12. Liu et al. High-dose dexamethasone shifts the balance of stimulatory and inhibitory Fcgamma receptors on monocytes in patients with primary immune thrombocytopenia. Blood. 2011 Feb. 10; 117(6):2061-9.
13. Zhang et al. Divergent intracellular sorting of Fc-gamma-RIIA and Fc-gamma-RIIB2 J Biol Chem. 2010 Oct. 29; 285(44):34250-8.
14. Warmerdam et al. A single amino acid in the second Ig-like domain of the human Fcγ receptor II is critical for human IgG2 binding. J. Immunol. 1991; 27:1338-1343
15. Mulder et al. Activation of granulocytes by anti-neutrophil cytoplasmic antibodies (ANCA): a Fc gamma RII-dependent process. Clin Exp Immunol. 1994 November; 98(2):270-8.
16. DiGiandomenico et al. Identification of broadly protective human antibodies to Pseudomonas aeruginosa exopolysaccharide Psl by phenotypic screening. J Exp Med. 2012 Jul. 2; 209(7):1273-87.
17. Brinkmann et al. A Neutrophil extracellular traps kill bacteria. Science 2004 Mar. 5; 303(5663):1532-5.
18. Fuchs et al. Neutrophil extracellular trap (NET) impact on deep vein thrombosis. Arterioscler. Thromb. Vasc. Biol. 2012; 201232(8):1777-1783.
19. Villanueva et al. Netting neutrophils induce endothelial damage, infiltrate tissues, and expose immune stimulatory molecules in systemic lupus erythematosus. J. Immunol. 2011; 187(1):538-552.
20. Carmona-Rivera et al. Neutrophil extracellular traps induce endothelial dysfunction in systemic lupus erythematosus through the activation of matrixmetalloproteinase-2. Ann. Rheum. Dis. 2015 July; 74(7):1417-24.
21. Allam et al. Extracellular histones in tissue injury and inflammation. J. Mol. Med. (Berl.) 2014 May; 92(5):465-72.
22. Wang et al. Increased neutrophil elastase and proteinase 3 and augmented NETosis are closely associated with (3-cell autoimmunity in patients with type 1 diabetes. Diabetes 2014 December; 63(12):4239-48.
23. Krishna et al. Immunogenicity to Biotherapeutics—The Role of Anti-drug Immune Complexes. Front. Immunol. 2016 Feb. 2; 7:21.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The present invention is further described by the following claims.

The invention claimed is:

1. An isolated nucleic acid molecule comprising a nucleotide sequence encoding a binding molecule that comprises:

(i) a heavy chain variable (VH) region comprising a VH-complementarity determining region (CDR)1 comprising SEQ ID NO: 29, VH-CDR2 comprising SEQ ID NO: 19, and VH-CDR3 comprising SEQ ID NO: 30; and (ii) a light chain variable (VL) region comprising a VL-CDR1 comprising SEQ ID NO: 22, VL-CDR2 comprising SEQ ID NO: 31, and VL-CDR3 comprising SEQ. ID NO: 32.

2. The nucleic acid molecule of claim 1, operably linked to a regulatory sequence.

3. A vector comprising the nucleic acid molecule of claim 1.

4. A host cell transformed with a nucleic acid molecule of claim 1, or the vector of claim 3.

5. The host cell of claim 4, which is a mammalian host cell.

6. A composition comprising the nucleic acid molecule of claim 1, the vector of claim 3, or the host cell of claim 4.

7. A method of making a binding molecule that specifically binds FcγRIIA, the method comprising culturing the host cell of claim 4 under suitable conditions for producing the binding molecule.

8. The method of claim 7, further comprising isolating the binding molecule.

9. A kit comprising the nucleic acid molecule of claim 1.

* * * * *